United States Patent
Kilroy et al.

(10) Patent No.: US 10,383,699 B2
(45) Date of Patent: Aug. 20, 2019

(54) HYPERDEXTEROUS SURGICAL SYSTEM

(71) Applicant: SRI INTERNATIONAL, Menlo Park, CA (US)

(72) Inventors: Pablo Eduardo Garcia Kilroy, Menlo Park, CA (US); Thomas D. Egan, Marblehead, MA (US); Karen Shakespear Koenig, San Francisco, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 436 days.

(21) Appl. No.: 14/388,180

(22) PCT Filed: Mar. 13, 2014

(86) PCT No.: PCT/US2014/026115
§ 371 (c)(1),
(2) Date: Sep. 25, 2014

(87) PCT Pub. No.: WO2014/151621
PCT Pub. Date: Sep. 25, 2014

(65) Prior Publication Data
US 2015/0038981 A1 Feb. 5, 2015

Related U.S. Application Data

(60) Provisional application No. 61/791,248, filed on Mar. 15, 2013, provisional application No. 61/906,802, (Continued)

(51) Int. Cl.
*A61B 19/00* (2006.01)
*A61B 90/50* (2016.01)
(Continued)

(52) U.S. Cl.
CPC .............. *A61B 90/50* (2016.02); *A61B 34/25* (2016.02); *A61B 34/30* (2016.02); *A61B 34/37* (2016.02);
(Continued)

(58) Field of Classification Search
CPC ... A61B 19/2203; A61B 90/361; A61B 90/37; A61B 34/37; A61B 34/25; A61B 90/11;
(Continued)

(56) References Cited

U.S. PATENT DOCUMENTS

| 4,843,921 A | 7/1989 | Kremer |
| 5,339,723 A | 8/1994 | Huitema |

(Continued)

FOREIGN PATENT DOCUMENTS

| CA | 2913943 A1 | 12/2014 |
| CN | 101031236 A | 9/2007 |

(Continued)

OTHER PUBLICATIONS

Supplemental European Search Report dated Mar. 10, 2016 in EP Application No. 14767688.

(Continued)

*Primary Examiner* — Mark Bockelman
(74) *Attorney, Agent, or Firm* — Womble Bond Dickinson (US) LLP

(57) ABSTRACT

A hyperdexterous surgical system is provided. The system can include one or more surgical arms coupleable to a fixture and configured to support one or more surgical tools. The system can include an electronic control system configured to communicate electronically with the one or more robotic surgical tools. The control system can electronically control the operation of the one or more surgical tools. The system can include one or more portable handheld controllers actuatable by a surgeon to communicate one or more control (Continued)

signals to the one or more surgical tools via the electronic control system to operate the one or more surgical tools. The one or more portable handheld controllers can provide said one or more control signals from a plurality of locations of an operating arena, allowing a surgeon to be mobile during a surgical procedure and to remotely operate the one or more surgical tools from different locations of the operating arena.

20 Claims, 51 Drawing Sheets

Related U.S. Application Data filed on Nov. 20, 2013, provisional application No. 61/908,888, filed on Nov. 26, 2013, provisional application No. 61/915,403, filed on Dec. 12, 2013, provisional application No. 61/935,966, filed on Feb. 5, 2014.

(51) Int. Cl.
| | |
|---|---|
| *A61B 90/10* | (2016.01) |
| *A61B 34/00* | (2016.01) |
| *A61B 90/00* | (2016.01) |
| *A61B 34/30* | (2016.01) |
| *A61B 90/11* | (2016.01) |
| *A61B 34/37* | (2016.01) |
| *A61B 90/60* | (2016.01) |
| *A61B 17/00* | (2006.01) |
| *A61B 90/57* | (2016.01) |

(52) U.S. Cl.
CPC .............. *A61B 34/74* (2016.02); *A61B 90/10* (2016.02); *A61B 90/11* (2016.02); *A61B 90/361* (2016.02); *A61B 90/37* (2016.02); *A61B 90/60* (2016.02); *A61B 2017/00207* (2013.01); *A61B 2017/00221* (2013.01); *A61B 2034/306* (2016.02); *A61B 2090/371* (2016.02); *A61B 2090/571* (2016.02)

(58) Field of Classification Search
CPC ......... A61B 34/30; A61B 90/50; A61B 90/60; A61B 34/74; A61B 90/10; A61B 2090/571; A61B 2090/371; A61B 2034/306

See application file for complete search history.

(56) References Cited

U.S. PATENT DOCUMENTS

| | | | |
|---|---|---|---|
| 5,720,742 | A | 2/1998 | Zacharias |
| 5,855,583 | A | 1/1999 | Wang et al. |
| 6,132,368 | A | 10/2000 | Cooper |
| 6,270,508 | B1 | 8/2001 | Klieman et al. |
| 6,331,181 | B1 | 12/2001 | Tierney et al. |
| 6,346,072 | B1 | 2/2002 | Cooper |
| 6,425,289 | B1 | 7/2002 | Igel et al. |
| 6,450,978 | B1 | 9/2002 | Brosseau et al. |
| 6,451,027 | B1 | 9/2002 | Cooper et al. |
| 6,459,926 | B1 | 10/2002 | Nowlin et al. |
| 6,471,642 | B1 | 10/2002 | Igarashi |
| 6,490,490 | B1 | 12/2002 | Uchikubo et al. |
| 6,491,701 | B2 | 12/2002 | Tierney et al. |
| 6,522,906 | B1 | 2/2003 | Salisbury, Jr. et al. |
| 6,535,756 | B1 | 3/2003 | Simon et al. |
| 6,582,358 | B2 | 6/2003 | Akui et al. |
| 6,587,750 | B2 | 7/2003 | Gerbi et al. |
| 6,608,628 | B1 | 8/2003 | Ross et al. |
| 6,659,939 | B2 | 12/2003 | Moll et al. |
| 6,669,635 | B2 | 12/2003 | Kessman et al. |
| 6,682,478 | B2 | 1/2004 | Nakamura |
| 6,700,391 | B2 | 3/2004 | Strack et al. |
| 6,768,496 | B2 | 7/2004 | Bieger et al. |
| 6,772,646 | B1 | 8/2004 | Madni et al. |
| 6,788,018 | B1 | 9/2004 | Blumenkranz |
| 6,793,625 | B2 | 9/2004 | Cavallaro et al. |
| 6,799,065 | B1 | 9/2004 | Niemeyer |
| 6,866,671 | B2 | 3/2005 | Tierney et al. |
| 6,892,090 | B2 | 5/2005 | Verard et al. |
| 6,920,347 | B2 | 7/2005 | Simon et al. |
| 6,951,535 | B2 | 10/2005 | Ghodoussi et al. |
| 6,955,097 | B1 | 10/2005 | Madni et al. |
| 6,962,581 | B2 | 11/2005 | Thoe |
| 6,995,744 | B1 | 2/2006 | Moore et al. |
| 7,008,362 | B2 | 3/2006 | Fitzgibbon |
| 7,012,203 | B2 | 3/2006 | Hanson et al. |
| 7,046,270 | B2 | 5/2006 | Murata et al. |
| 7,048,745 | B2 | 5/2006 | Tierney et al. |
| 7,076,286 | B2 | 7/2006 | Mizoguchi et al. |
| 7,101,334 | B2 | 9/2006 | Takahashi |
| 7,106,479 | B2 | 9/2006 | Roy et al. |
| 7,206,627 | B2 | 4/2007 | Abovitz et al. |
| 7,217,269 | B2 | 5/2007 | El-Galley et al. |
| 7,277,120 | B2 | 10/2007 | Gere et al. |
| 7,317,955 | B2 | 1/2008 | McGreevy |
| 7,319,466 | B1 | 1/2008 | Tarr et al. |
| 7,331,967 | B2 | 2/2008 | Lee et al. |
| 7,357,774 | B2 | 4/2008 | Cooper |
| 7,369,116 | B2 | 5/2008 | Logue |
| 7,379,790 | B2 | 5/2008 | Toth et al. |
| 7,417,665 | B2 | 8/2008 | Banju et al. |
| 7,498,532 | B2 | 3/2009 | Kuhner et al. |
| 7,524,320 | B2 | 4/2009 | Tierney et al. |
| 7,554,526 | B2 | 6/2009 | Logue |
| 7,594,912 | B2 | 9/2009 | Cooper et al. |
| 7,666,191 | B2 | 2/2010 | Orban, III et al. |
| 7,671,888 | B2 | 3/2010 | Nogami et al. |
| 7,683,926 | B2 | 3/2010 | Schechterman et al. |
| 7,699,855 | B2 | 4/2010 | Anderson et al. |
| 7,727,244 | B2 | 6/2010 | Orban, III et al. |
| 7,768,702 | B2 | 8/2010 | Hirose et al. |
| 7,781,941 | B2 | 8/2010 | Horvath et al. |
| 7,783,133 | B2 | 8/2010 | Dunki-Jacobs et al. |
| 7,789,874 | B2 | 9/2010 | Yu et al. |
| 7,789,875 | B2 | 9/2010 | Brock et al. |
| 7,806,891 | B2 | 10/2010 | Nowlin et al. |
| 7,819,885 | B2 | 10/2010 | Cooper |
| 7,840,042 | B2 | 11/2010 | Kriveshko et al. |
| 7,843,158 | B2 | 11/2010 | Prisco |
| 7,853,305 | B2 | 12/2010 | Simon et al. |
| 7,865,266 | B2 | 1/2011 | Moll et al. |
| 7,883,458 | B2 | 2/2011 | Hamel |
| 7,907,166 | B2 | 3/2011 | Lamprecht et al. |
| 7,922,439 | B2 | 4/2011 | Kato |
| 7,947,050 | B2 | 5/2011 | Lee et al. |
| 7,955,322 | B2 | 6/2011 | Devengenzo et al. |
| 7,979,157 | B2 | 7/2011 | Anvari |
| 7,983,793 | B2 | 7/2011 | Toth et al. |
| 7,997,132 | B2 | 8/2011 | Ross, Jr. et al. |
| 8,004,229 | B2 | 8/2011 | Nowlin et al. |
| 8,062,288 | B2 | 11/2011 | Cooper et al. |
| 8,079,950 | B2 | 12/2011 | Stern et al. |
| 8,086,008 | B2 | 12/2011 | Coste-Maniere et al. |
| 8,095,200 | B2 | 1/2012 | Quaid, III |
| 8,100,133 | B2 | 1/2012 | Mintz et al. |
| 8,105,338 | B2 | 1/2012 | Anderson et al. |
| 8,118,805 | B2 | 2/2012 | Jinno et al. |
| 8,120,301 | B2 | 2/2012 | Goldberg et al. |
| 8,121,283 | B2 | 2/2012 | Peng et al. |
| 8,126,114 | B2 | 2/2012 | Naylor et al. |
| 8,131,031 | B2 | 3/2012 | Lloyd |
| 8,142,447 | B2 | 3/2012 | Cooper et al. |
| 8,147,503 | B2 | 4/2012 | Zhao et al. |
| 8,155,479 | B2 | 4/2012 | Hoffman et al. |
| 8,190,238 | B2 | 5/2012 | Moll et al. |
| 8,202,278 | B2 | 6/2012 | Orban, III et al. |
| 8,206,406 | B2 | 6/2012 | Orban, III |
| 8,251,331 | B2 | 8/2012 | Fowler |
| 8,256,319 | B2 | 9/2012 | Cooper et al. |
| 8,284,234 | B2 | 10/2012 | Bjelkhagen et al. |

(56) References Cited

U.S. PATENT DOCUMENTS

| | | |
|---|---|---|
| 8,332,072 B1 | 12/2012 | Schaible et al. |
| 8,333,129 B2 | 12/2012 | Johnson et al. |
| 8,391,954 B2 | 3/2013 | Quaid, III |
| 8,395,342 B2 | 3/2013 | Prisco |
| 8,398,541 B2 | 3/2013 | DiMaio et al. |
| 8,418,073 B2 | 4/2013 | Mohr et al. |
| 8,469,947 B2 | 6/2013 | Devengenzo et al. |
| 8,473,031 B2 | 6/2013 | Nixon et al. |
| 8,504,136 B1 | 8/2013 | Sun et al. |
| 8,506,555 B2 | 8/2013 | Ruiz Morales |
| 8,508,173 B2 | 8/2013 | Goldberg et al. |
| 8,521,331 B2 | 8/2013 | Itkowitz |
| 8,527,094 B2 | 9/2013 | Kumar et al. |
| 8,541,970 B2 | 9/2013 | Nowlin et al. |
| 8,562,594 B2 | 10/2013 | Cooper et al. |
| 8,594,841 B2 | 11/2013 | Zhao et al. |
| 8,600,551 B2 | 12/2013 | Itkowitz et al. |
| 8,602,968 B2 | 12/2013 | Umemoto et al. |
| 8,620,473 B2 | 12/2013 | Diolaiti et al. |
| 8,624,537 B2 | 1/2014 | Nowlin et al. |
| 8,628,518 B2 | 1/2014 | Blumenkranz et al. |
| 8,634,957 B2 | 1/2014 | Toth et al. |
| 8,638,056 B2 | 1/2014 | Goldberg et al. |
| 8,648,896 B2 | 2/2014 | Takahashi |
| 8,672,922 B2 | 3/2014 | Loh et al. |
| 8,682,489 B2 | 3/2014 | Itkowitz et al. |
| 8,706,184 B2 | 4/2014 | Mohr et al. |
| 8,712,115 B2 | 4/2014 | Kirchberg et al. |
| 8,715,167 B2 | 5/2014 | Stern et al. |
| 8,747,288 B2 | 6/2014 | Strotzer et al. |
| 8,749,189 B2 | 6/2014 | Nowlin et al. |
| 8,749,190 B2 | 6/2014 | Nowlin et al. |
| 8,761,337 B2 | 6/2014 | Naylor et al. |
| 8,786,241 B2 | 7/2014 | Nowlin et al. |
| 8,806,359 B2 | 8/2014 | Garibaldi et al. |
| 8,816,628 B2 | 8/2014 | Nowlin et al. |
| 8,823,308 B2 | 9/2014 | Nowlin et al. |
| 8,828,023 B2 | 9/2014 | Neff et al. |
| 8,831,782 B2 | 9/2014 | Itkowitz |
| 8,870,861 B2 | 10/2014 | El-Galley et al. |
| 8,888,764 B2 | 11/2014 | Devengenzo et al. |
| 8,930,027 B2 | 1/2015 | Schaible et al. |
| 8,939,500 B2 | 1/2015 | Voigt et al. |
| 8,968,333 B2 | 3/2015 | Yu et al. |
| 8,989,903 B2 | 3/2015 | Weir et al. |
| 8,996,173 B2 | 3/2015 | Itkowitz et al. |
| 9,002,517 B2 | 4/2015 | Bosscher et al. |
| 9,026,247 B2 | 5/2015 | White et al. |
| 9,068,824 B2 | 6/2015 | Findeisen et al. |
| 9,078,686 B2 | 7/2015 | Schena |
| 9,101,267 B2 | 8/2015 | Umasuthan et al. |
| 9,108,318 B2 | 8/2015 | Diolaiti |
| 9,129,422 B2 | 9/2015 | Mountney et al. |
| 9,138,135 B2 | 9/2015 | Oderwald et al. |
| 9,161,681 B2 | 10/2015 | Galstian et al. |
| 9,179,980 B2 | 11/2015 | Yoon |
| 9,192,286 B2 | 11/2015 | Kazakevich et al. |
| 9,198,731 B2 | 12/2015 | Balaji et al. |
| 9,215,293 B2 | 12/2015 | Miller |
| 9,221,172 B2 | 12/2015 | Williamson et al. |
| 9,232,984 B2 | 1/2016 | Guthart et al. |
| 9,241,768 B2 | 1/2016 | Sandhu et al. |
| 9,254,078 B2 | 2/2016 | McDowall |
| 9,254,572 B2 | 2/2016 | Strotzer |
| 9,256,936 B2 | 2/2016 | Jacobs et al. |
| 9,259,276 B2 | 2/2016 | Mintz et al. |
| 9,259,282 B2 | 2/2016 | Azizian et al. |
| 9,272,425 B2 | 3/2016 | Garcia et al. |
| 9,295,524 B2 | 3/2016 | Schena et al. |
| 9,320,568 B2 | 4/2016 | Orban, III et al. |
| 9,333,042 B2 | 5/2016 | Diolaiti et al. |
| 9,345,544 B2 | 5/2016 | Hourtash et al. |
| 9,345,546 B2 | 5/2016 | Toth et al. |
| 9,360,934 B2 | 6/2016 | Ruiz Morales et al. |
| 9,433,288 B2 | 9/2016 | Voigt et al. |
| 9,486,159 B2 | 11/2016 | Coste-Maniere et al. |
| 9,554,866 B2 | 1/2017 | Cunningham et al. |
| 2002/0082612 A1 | 6/2002 | Moll et al. |
| 2004/0106916 A1 | 6/2004 | Quaid et al. |
| 2004/0199147 A1 | 10/2004 | Nishizawa et al. |
| 2004/0243147 A1 | 12/2004 | Lipow |
| 2007/0049435 A1 | 3/2007 | Jinno et al. |
| 2007/0089557 A1 | 4/2007 | Solomon et al. |
| 2008/0046122 A1 | 2/2008 | Manzo et al. |
| 2008/0154246 A1 | 6/2008 | Nowlin et al. |
| 2008/0177284 A1 | 7/2008 | Lee et al. |
| 2009/0171332 A1 | 7/2009 | Bonneau |
| 2009/0192519 A1 | 7/2009 | Omori |
| 2009/0234369 A1 | 9/2009 | Bax et al. |
| 2009/0326555 A1 | 12/2009 | Vohra et al. |
| 2010/0004663 A1 | 1/2010 | Murphy et al. |
| 2010/0016852 A1 | 1/2010 | Manzo et al. |
| 2010/0082041 A1 | 4/2010 | Prisco |
| 2010/0175701 A1 | 7/2010 | Reis et al. |
| 2010/0198253 A1 | 8/2010 | Jinno et al. |
| 2010/0279736 A1 | 11/2010 | Ruotolo et al. |
| 2010/0312291 A1 | 12/2010 | Mast et al. |
| 2011/0118748 A1 | 5/2011 | Itkowitz |
| 2011/0118752 A1 | 5/2011 | Itkowitz et al. |
| 2011/0277776 A1 | 11/2011 | McGrogan et al. |
| 2012/0130399 A1 | 5/2012 | Moll et al. |
| 2012/0154564 A1 | 6/2012 | Hoffman et al. |
| 2012/0277663 A1 | 11/2012 | Millman et al. |
| 2012/0316681 A1 | 12/2012 | Hagn et al. |
| 2013/0030448 A1 | 1/2013 | Cooper et al. |
| 2013/0063580 A1 | 3/2013 | Ogawa et al. |
| 2013/0085510 A1* | 4/2013 | Stefanchik .......... G06F 19/3481 606/130 |
| 2013/0325031 A1 | 12/2013 | Schena et al. |
| 2014/0005484 A1* | 1/2014 | Charles ................. A61B 17/02 600/201 |
| 2014/0100588 A1 | 4/2014 | Blumenkranz et al. |
| 2014/0107627 A1 | 4/2014 | Blumenkranz et al. |
| 2014/0130810 A1 | 5/2014 | Azizian et al. |
| 2014/0168073 A1 | 6/2014 | Chizeck et al. |
| 2014/0171965 A1 | 6/2014 | Loh et al. |
| 2014/0188131 A1 | 7/2014 | Toth et al. |
| 2014/0282196 A1 | 9/2014 | Zhao et al. |
| 2015/0025549 A1 | 1/2015 | Kilroy et al. |
| 2015/0032126 A1 | 1/2015 | Nowlin et al. |
| 2015/0038981 A1 | 2/2015 | Kilroy et al. |
| 2015/0038982 A1 | 2/2015 | Kilroy et al. |
| 2015/0045812 A1 | 2/2015 | Seo |
| 2015/0051733 A1 | 2/2015 | Nowlin et al. |
| 2015/0145814 A1 | 5/2015 | Burger |
| 2015/0150635 A1 | 6/2015 | Kilroy et al. |
| 2015/0157410 A1 | 6/2015 | Kilroy et al. |
| 2015/0209965 A1 | 7/2015 | Low et al. |
| 2015/0265356 A1 | 9/2015 | Schena |
| 2015/0289366 A1 | 10/2015 | Frey et al. |
| 2015/0321355 A1 | 11/2015 | Kishi |
| 2016/0140875 A1 | 5/2016 | Kumar et al. |
| 2016/0157943 A1 | 6/2016 | Mintz et al. |
| 2016/0166345 A1 | 6/2016 | Kumar et al. |
| 2016/0184037 A1 | 6/2016 | Cooper et al. |
| 2016/0242860 A1 | 8/2016 | Diolaiti et al. |
| 2017/0020615 A1 | 1/2017 | Koenig et al. |
| 2017/0079725 A1 | 3/2017 | Hoffman et al. |

FOREIGN PATENT DOCUMENTS

| | | |
|---|---|---|
| CN | 101222882 A | 7/2008 |
| CN | 101291635 | 10/2008 |
| CN | 101616636 A | 12/2009 |
| CN | 102143714 A | 8/2011 |
| CN | 102665589 | 9/2012 |
| CN | 102869310 A | 1/2013 |
| CN | 102958464 A | 3/2013 |
| EP | 2415418 | 2/2012 |
| EP | 2967521 A1 | 1/2016 |
| EP | 2967623 A1 | 1/2016 |
| GB | 2523224 | 8/2015 |
| JP | 2002-503976 | 2/2002 |
| JP | 2004-122286 A | 4/2004 |

(56) References Cited

FOREIGN PATENT DOCUMENTS

| | | |
|---|---|---|
| JP | 2004344180 | 12/2004 |
| JP | 2008079371 | 4/2008 |
| JP | 2010220786 | 10/2010 |
| JP | 2011-237987 A | 11/2011 |
| JP | 2012-504016 | 2/2012 |
| JP | 2013-009813 A | 1/2013 |
| SE | 525 399 C2 | 2/2005 |
| WO | WO-9743943 | 11/1997 |
| WO | WO-2006124388 | 11/2006 |
| WO | 2010/009223 A2 | 1/2010 |
| WO | WO 2011/060185 | 5/2011 |
| WO | WO-2011060185 | 5/2011 |
| WO | WO-2014084408 | 6/2014 |
| WO | WO 2014084408 | 6/2014 |
| WO | WO 2014/151621 | 9/2014 |
| WO | WO 2014/151952 | 9/2014 |
| WO | WO-2014/152694 A1 | 9/2014 |
| WO | WO-2014151621 | 9/2014 |
| WO | WO-2014151952 | 9/2014 |
| WO | WO-2014/201538 A1 | 12/2014 |
| WO | WO-2016/048738 A1 | 3/2016 |
| WO | WO-2017/015599 A1 | 1/2017 |

OTHER PUBLICATIONS

Final Office Action dated Jul. 15, 2016, for U.S. Appl. No. 14/510,465, filed Oct. 9, 2014, 13 pages.
Final Office Action dated Jul. 14, 2016, for U.S. Appl. No. 14/510,475, filed Oct. 9, 2014, 13 pages.
Final Office Action dated May 26, 2017, for U.S. Appl. No. 14/510,465, filed Oct. 9, 2014, 15 pages.
Final Office Action dated May 26, 2017, for U.S. Appl. No. 14/510,475, filed Oct. 9, 2014, 14 pages.
International Search Report dated Nov. 30, 2016, for PCT Application No. PCT/US2016/043666, filed on Jul. 22, 2016, 5 pages.
Non-Final Office Action dated Sep. 23, 2015, for U.S. Appl. No. 14/510,465, filed Oct. 9, 2014, 9 pages.
Non-Final Office Action dated Sep. 24, 2015, for U.S. Appl. No. 14/510,475, filed Oct. 9, 2014, 8 pages.
Non-Final Office Action dated Nov. 4, 2016, for U.S. Appl. No. 14/510,475, filed Oct. 9, 2014, 13 pages.
Non-Final Office Action dated Jul. 28, 2017, for U.S. Appl. No. 14/510,566, filed Oct. 9, 2014, 7 pages.
Written Opinion of the International Searching Authority dated Nov. 30, 2016, for PCT Application No. PCT/US2016/043666, filed on Jul. 22, 2016, 10 pages.
U.S. Appl. No. 15/706,536, filed Sep. 15, 2017, by Koenig et al.
U.S. Appl. No. 15/706,582, filed Sep. 15, 2017, by Devengenzo et al.
U.S. Appl. No. 15/706,585, filed Sep. 15, 2017, by Cordoba et al.
Australian Examination Report No. 1, dated Jan. 4, 2018, AU Application No. 2014233662.
Chinese Notification of Grant of Patent for Invention dated Apr. 12, 2018, CN Application No. 201480021279.X.
Final Office Action dated Jan. 11, 2018, U.S. Appl. No. 14/510,566.
Final Office Action dated May 26, 2017, U.S. Appl. No. 14/510,475.
Final Office Action dated Jul. 14, 2016, U.S. Appl. No. 14/510,475.
International Preliminary Report on Patentability dated Sep. 15, 2015 in PCT Application No. PCT/US2014/026115.
International Preliminary Report on Patentability dated Sep. 15, 2015 in PCT Application No. PCT/US2014/026721.
International Search Report and Written Opinion dated Aug. 18, 2014 in PCT Application No. PCT/US2014/026721.
International Search Report and Written Opinion dated Nov. 2, 2015 in PCT Application No. PCT/US2015/042991.
International Search Report and Written Opinion dated Aug. 21, 2014 in PCT Application No. PCT/US2014/026115.
International Search Report and Written Opinion dated Jan. 7, 2016 in PCT Application No. PCT/US2015/052354.
Japanese Notice of Reasons for Rejection dated Jan. 9, 2018, JP Application No. 2016-502224.
Japanese Notice of Reasons for Rejection dated Dec. 12, 2017, JP Application No. 2016-502057.
Non Final Office Action dated Nov. 4, 2016, U.S. Appl. No. 14/510,475.
Non Final Office Action dated Sep. 24, 2015, U.S. Appl. No. 14/510,475.
Non-Final Office Action dated Dec. 14, 2017, U.S. Appl. No. 14/510,465.
Supplemental European Search Report dated Jun. 29, 2016 in EP Application No. 14770569.
Supplemental European Search Report dated Mar. 9, 2016 in EP Application No. 14767688.
Supplemental Partial European Search Report dated Mar. 9, 2016 in EP Application No. 14770569.
Full Australian Examination Report No. 2 dated Aug. 9, 2018, for related Australian Patent Appln. No. 2014233662 6 Pages.
Notice of Acceptance for Australian Patent Application No. 2014233662, dated Jan. 3, 2019.
Notice of Allowance for U.S. Appl. No. 14/510,465, dated Dec. 31, 2018.
Notice of Allowance and Fees Due (PTOL-85) dated Oct. 13, 2017 for U.S. Appl. No. 14/388,208.
Notice of Allowance and Fees Due (PTOL-85) dated Oct. 12, 2017 for U.S. Appl. No. 14/677,509.
Non-Final Rejection dated Nov. 3, 2016 for U.S. Appl. No. 14/510,465.
Non-Final Office Action dated Mar. 22, 2017, for U.S. Appl. No. 14/677,509, filed Apr. 2, 2015, 11 pages.
Non-Final Office Action dated Mar. 21, 2017, for U.S. Appl. No. 14/388,208, filed Sep. 25, 2014, 11 pages.
English Translation of CN Office Action dated Dec. 30, 2016 for CN Application No. 201480021279.
Advisory Action (PTOL-303) dated Sep. 28, 2016 for U.S. Appl. No. 14/510,475.
Advisory Action (PTOL-303) dated Oct. 12, 2016 for U.S. Appl. No. 14/510,465.
Advisory Action (PTOL-303) dated Aug. 17, 2017 for U.S. Appl. No. 14/510,475.
Advisory Action (PTOL-303) dated Aug. 16, 2017 for U.S. Appl. No. 14/510,465.
Notice of Allowance for Related U.S. Appl. No. 14/510,566 dated Mar. 27, 2019.
Notice of Allowability for U.S. Appl. No. 14/510,465, dated Mar. 20, 2019 6 pages.

* cited by examiner

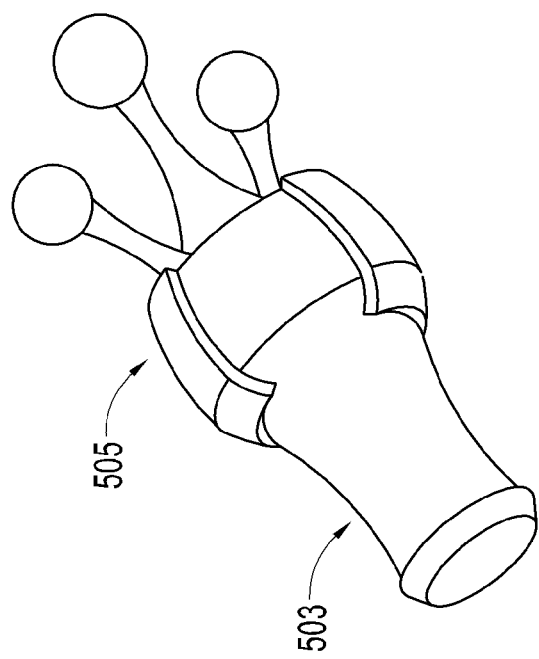
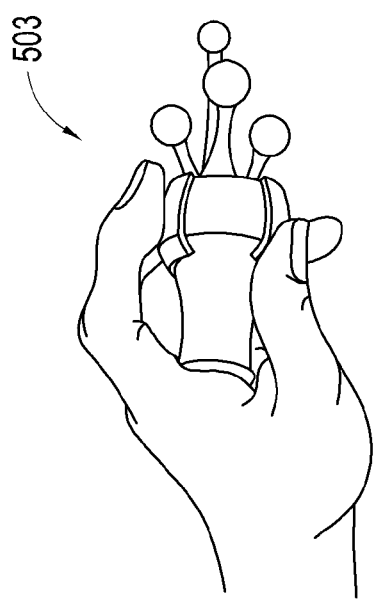
FIG. 32B

VIRTUAL GRIP

Table 1

| | | Tools Use | | | |
|---|---|---|---|---|---|
| | | Hyperdexterous Tool: Grasper 1 | Hyperdexterous Tool: Grasper 2 | Hyperdexterous Tool: Camera | Manual Tool: Stapler |
| Order of events. | 1. Acquire good visual of the operating space<br><br>10 | | | Use either of the two Wireless Controllers, map it to the tool holding the camera and position the camera | |
| | 2. Mobilize colon and position one end of the staple line<br><br>20 | Use the Wireless Controller controlled by the right hand to grasp the colon and to position it. Declutch this robotic tool and set the Wireless controller down in a sterile area | | | |
| | 3. Postion the manual stapler<br><br>30 | | | | Use the right hand to position the manual stapler |
| | 4. Position the colon on the other end of the staple line<br>40 | | Use the Wireless Controller controlled by the left hand to grasp the colon and to position it. | | |
| | 5. Position and staple (Simultaneos motion)<br><br><br>50 | | Continue to position the colon with the left hand while manipulating the stapler with the right hand to get the best staple position | | Continue to position the colon with the left hand while manipulating the stapler with the right hand to get the best staple position |
| | 6. Deliver staples<br><br><br><br>60 | | | | Use stapler to deliver staples. The left grasper may be declutched so that the tissue is held in place while stapling |

FIG. 39

A RIGHTWARD MOTION OF
THE LEFT HAND OF THE
SURGEON ON FIG.42A IN THE
DIRECTION OF ARROW A
WILL MOVE TOOL
RIGHTWARD ON THE SCREEN

Zoom Capabilty

Zoomed in

Zoomed section

Mid-zoom

Zoomed out

HYPERDEXTEROUS SURGICAL SYSTEM

INCORPORATION BY REFERENCE TO ANY PRIORITY APPLICATIONS

This application is a US National Phase of International Application No. PCT/US2014/026115 filed Mar. 13, 2014 designating the US and published in English on Sep. 25, 2014 as WO 2014/151621, which claims the priority benefit under 35 U.S.C. § 119(e) of U.S. Provisional Application No. 61/791,248 filed Mar. 15, 2013, U.S. Provisional Application No. 61/906,802 filed Nov. 20, 2013, U.S. Provisional Application No. 61/908,888 filed Nov. 26, 2013, U.S. Provisional Application No. 61/915,403 filed Dec. 12, 2013, and U.S. Provisional Application No. 61/935,966 filed Feb. 5, 2014, all of which are hereby incorporated by reference in their entirety and should be considered a part of this specification.

BACKGROUND

Field

Surgical robots allow surgeons to operate on patients in a minimally invasive manner. The present application relates to surgical systems and methods, and more particularly to a hyperdexterous surgical system with one or more hyperdexterous surgical arms and one or more hyperdexterous surgical tools, and methods of operating the same.

Description of the Related Art

Currently, surgeons must select between discrete modes of minimally invasive surgery utilizing many techniques. Laparoscopic surgery generally falls in two categories: laparoscopic surgery with manual tools and laparoscopic surgery with robotic tools. In laparoscopic surgery using manual tools, procedures are typically performed through small incisions. The manual tools can be translated, rotated, and/or moved about a fulcrum. For manual tools that rotate about a fulcrum, the surgeon holds the handle of the tool. As the surgeon moves the handle in one direction, the distal end of the tool moves in another direction. The resulting motion of the distal end of the tool relative to the motion of the proximal end of the tool may not be natural, requiring the surgeon to practice the technique.

The motions of the laparoscopic tool are captured by a laparoscopic camera. The laparoscopic camera has a long shaft that is inserted into the body through an incision just like a manual tool. The laparoscopic camera is positioned to view the distal tips of the manual tools and captures the motion of the distal end of the tools. The display typically shows the motion of the tools relative to the frame of reference of the camera. For manual tools that rotate about a fulcrum, the tool moves in a polar coordinate system which may not be readily apparent based on the images of the laparoscopic camera.

Another mode of laparoscopic surgery is robotic surgery. In on-market robotic surgical systems, a large robotic arm controls a robotic tool. The tool is inserted into a small incision. The distal end of the robotic tool typically includes an end effector (e.g., a grasper, stapler, etc.) for performing a procedure within the body of the patient. The end effector is translated in space, within the constraints of the capabilities of the robotic arm. The surgeon typically controls the robotic arm from an immersive console that is remote from the patient. The robotic tool is configured to do certain surgical tasks well, but is not well-suited for other surgical tasks.

In on-market surgical robotic systems, the motions of the robotic tool are generally captured by a robotic camera. The motions of the robotic camera are controlled by a robotic arm, also under control of the surgeon just like the robotic arms controlling the robotic tools. The surgeon can map the movements of his hand to the movement of the robotic tool in the frame of reference of the camera. The motions of the surgeon's hands are mapped to the distal end effectors of the robotic tools within the frame of reference of the robotic camera. The frame of reference is therefore limited to the view provided by the camera. The display typically shows the motion of the distal end of the robotic tools relative to the frame of reference of the camera. The surgeon must therefore create a mental model of the anatomy with the limited information provided by the camera to control the robotic tools as desired for a particular task. Due to his remote location, the surgeon cannot acquire additional views of the patient in order to augment his understanding of the surgical space. This mode of operation is limiting for large motions or motions where it is more natural to move with respect to a frame of reference outside the body of the patient. Therefore, controlling the distal tips of the robotic tools relative to the robotic camera frame of reference makes some aspects of the surgical procedure more natural as compared to laparoscopic surgery using manual tools. For example it may be easier to manipulate a needle holder tool in a suturing task. However, the limited frame of reference of the robotic camera makes some other aspects of the surgery less natural. For example, making large movements from one quadrant of the abdomen to another, especially motions that involve the camera sweeping through an arc that includes the midline of the patient, are very challenging. These same motions can be accomplished in a natural manner with manual tools from a frame of reference external to the patient's body.

The on-market systems have complex mechanisms controlling the tool, for instance controlling the rotation and translation of the tool. In some current robotic systems, translation of the tool is achieved using a complex and bulky series of nesting linear slides. In order to make the full length of the tool shaft available for surgery, the slides are attached to the extreme proximal end of the tool. As a result, in any condition except full extension of the tool into the body, the translation mechanism extends away from the patient's body. In this position, the translation mechanism is subject to interference with other components of the robotic arm or other robotic arms. The size of the rotation and translation mechanism does not allow close positioning of adjacent robotic arms, so in some cases, robotic tools are placed further apart. The translation mechanism imparts a high inertial load on the robotic arm when the tool moves through pitch and yaw, thereby necessitating a larger, more powerful arm. The rotation and translation mechanisms add weight to the distal end of the robotic arm. The linking segments and the motors to control the linking segments must therefore be larger in order to move the complex rotation and translation mechanisms controlling the robotic tool. Each additional segment and each additional motor add weight that compounds the problem. The distal end of the robotic arm is heavy and has to be supported by increasingly more powerful proximal joints to maintain adequate level of stiffness.

The robotic arms therefore are bulky and occupy the space surrounding the patient. In cases where multiple robotic arms used to perform a surgical procedure, the arms must be carefully coordinated to avoid collisions. Further, many additional steps are taken to reposition the robotic arm to avoid collisions between components of the robotic arm. Further, due to the angle of insertion, the size and design of the robotic arms and tools, and other factors, the robotic arm may be unable to reach certain locations, called dead zones. The large size of the robotic arm forces the surgical staff to plan the operation around the robotic arm. This leads to less flexibility and efficiency for surgical procedures. Additionally, on-market robotic arms are heavy. The design of the robotic systems requires specially designed operating arenas, already set up for the use of the robotic system. There is thus limited flexibility in the setup of the operating room.

The surgeon is located remotely from the patient when using on-market robotic surgical systems, often sitting or standing at a remote console. Typically, the surgeon views the surgery site and tools through a viewer which provides an immersive experience. In some cases, communication between the surgeon and the supporting staff is constrained or impeded due to the surgeon's position over the console. Teams that perform robotic surgery need to be highly trained and skilled since the surgeon is remote from the patient and unable to communicate with the staff directly. It takes months, in some cases years, of practice to achieve a high level of efficiency in situations where robotic surgery is performed. This makes it difficult for members of the team to be replaced. Additionally, from this remote location (at the console), the surgeon cannot simultaneously use manual tools while controlling the robot arm.

Some tasks such as executing large scale motion of the robotic tools from one surgical site to another surgical site in a patient's body become more difficult due to the interference of components of the robotic arms. Some tasks easily performed with manual tools are more complex or impossible to perform with robotic tools. For example, in some cases, the robot simply does not have an end effector capable of accomplishing the task. Some tasks requiring tactile feedback, such as palpation, cannot be done by the surgeon operating the robotic arm. Rather, the surgeon operating the robotic arm requires an assistant or a surgeon beside the operating table to assist in these types of tasks.

On-market robotic arms typically have two degrees of freedom. Typically, these two degrees of freedom come from a pitch mechanism and a roll mechanism. The robotic tool typically has four degrees of freedom. The robotic tool can typically translate and rotate. The robotic tool can typically pitch and yaw at the wrist. The on-market systems typically thus have six degrees of freedom including the degrees of freedom from the robotic arm and the robotic tool.

The translation mechanism used by some robotic arms cannot rotate about the shaft axis. To achieve rotation, these systems simply rotate just the tool shaft independently of the translation mechanism. The cables which articulate the end effector twist during rotation, thus causing friction and binding of the cables. This twisting causes a change of length in the cables which must be compensated for by elasticity or slack in the system. This twisting also causes a limitation on the range of rotation, typically limited to approximately +/−270° of rotation.

One drawback of the current modes of minimally invasive surgery discussed above is that they are discrete. In order for the surgeon to use manual tools at the operating table, he or she cannot be controlling the robotic arm at a remote console. In order for the surgeon to control the robotic arm at a remote console, he or she cannot be using manual tools at the operating table. The surgeon cannot simultaneously control both robotic tools and manual tools.

Another drawback of the current modes of minimally invasive surgery is that they provide limited information to the surgeon. Typically this information is limited to the view of a robotic camera. The surgeon is not provided with information about additional constraints, such as the location of the patient, surgeon, or tools relative to the image from the camera. The surgeon is not provided with information to understand the frame of reference of the camera without moving the tools and/or moving the robotic camera. By moving the tools and viewing the image, the surgeon can create a mental model of the work space inside the patient and the operating arena.

Another drawback with on-market robotic surgical systems is that they do not allow the surgeon the ability to reposition him or herself during surgery. The surgeon must remain at the immersive console to manipulate the robotic tools to perform a surgical task with the end effectors of the robotic tools.

Another drawback of on-market robotic surgical systems is that they are typically anchored to the ground and do not follow the orientation of the patient during the course of surgery. The position of the robotic arm and/or bed cannot be changed while the robotic arm is in use. Typically robotic arms are mounted to a horizontal level surface (e.g., anchored to the floor) and the patient is placed on a horizontal level surface (e.g., bed). In some surgeries, it may be advantageous to angle (e.g., tilt) the body of the patient relative to the horizontal surface (e.g., lowering the head of the patient to have internal organs shift toward the patient's head) based on the surgery to be performed.

Another drawback with on-market robotic arms is that accessing the workspace may require the robotic arms to move through a very large range of motion. The movement may be limited when multiple robotic arms are used for a single surgery. The chances of collision between the robotic arms or components of a single robotic arm increases. The challenge is to maximize the work space inside the body while maximizing the free space outside of the patient, while also keeping the robotic system small and compact.

SUMMARY OF THE INVENTION

There is a need for a surgical system that overcomes the deficiencies discussed above with on-market robotic surgical systems and provides flexibility to surgeons when performing surgical procedures.

The hyperdexterous surgical system discussed below overcomes many of the deficiencies discussed above and provides advantages over on-market robotic surgical systems. One advantage of the hyperdexterous surgical system is that the hyperdexterous surgical system is small and compact, and therefore can be mounted in a variety of ways to a variety of fixtures. One advantage of the hyperdexterous surgical system is that the hyperdexterous surgical arm can be mounted to follow an orientation of a patient during a surgical procedure, such as when the body of the patient is tilted to facilitate conducting a particular surgical procedure (e.g., to shift internal organs in a way that provides better access to the desired tissue or organ). One advantage of the hyperdexterous surgical system is the ability to use hyperdexterous surgical tools and manual tools simultaneously by a surgeon while operating on a patient. Another advantage of the hyperdexterous surgical system is that it is modular and thus provides flexibility in how the surgical arena is set up prior to or during a procedure, and allows the free space above the patient to be maximized. Still another advantage of the system is that it allows the surgeon to be mobile while performing a surgical procedure and to seamlessly move between using only manual tools, using manual and hyperdexterous surgical tools, and using only hyperdexterous surgical tools during the surgical procedure. Another advantage of the system is that it provides the surgeon with additional information that makes the operation of hyperdexterous surgical tools more natural. Still another advantage is that it provides the surgeon with the ability to reposition him or herself during surgery to perform a particular surgical task near the patient. For example, during the course of a surgical procedure, the surgeon may desire to manipulate tools from different positions based on the procedure to be done, or to reposition him or herself due to the manner in which a manual tool needs to be held. Still another advantage of the system is that the end effector of a hyperdexterous surgical tool can reach disparate locations inside the patient from a single entry point, such that the work space inside the patient's body is maximized. For example in abdominal surgery, there may be a need to access all four quadrants of the abdomen from a single entry point. Further advantages of the hyperdexterous surgical system will become apparent in the description provided herein.

In accordance with another aspect, the hyperdexterous surgical arm can couple to a fixture (e.g., operating table, hospital bed, examination table, wall, floor, ceiling, table, cart, or dolly). The hyperdexterous surgical arm can be supported by a support arm. The support arm can be moved to position the hyperdexterous surgical arm. The support arm can be moved to position the Remote Center. The hyperdexterous surgical arm can be supported by a horizontal position adjusting mechanism. The hyperdexterous surgical arm can be supported by a vertical position adjusting mechanism. The horizontal position adjusting mechanism and/or the vertical position adjusting mechanism can be moved to position the Remote Center.

In accordance with another aspect, the hyperdexterous surgical system can enable the one or more hyperdexterous surgical arms to be angled (e.g., tilt) to follow an orientation of a patient during the course of the surgery. Typically the patient is placed on a horizontal level surface (e.g., bed). In some surgeries, it may be advantageous to angle (e.g. tilt) the body of the patient relative to the horizontal surface (e.g., lowering the head of the patient to shift internal organs toward the head of the patient away from a surgical site for improved access to the surgical site) based on the surgery to be performed. The hyperdexterous surgical system thus enables the angling (e.g., tilting from horizontal) of the hyperdexterous surgical arm during the procedure with the hyperdexterous surgical arm in use.

In accordance with one aspect, the hyperdexterous surgical system accommodates the simultaneous use of a manual tool and a hyperdexterous surgical tool by one operator, such as a surgeon. The simultaneous use of manual tools and hyperdexterous surgical tools can be in the same workspace inside the patient. The operator can control a manual tool with one hand and a hyperdexterous surgical tool with the other hand.

The hyperdexterous surgical tool can include a tool shaft, a wrist and an end effector. The tool can have a motor pack at a proximal end or located at any point along the shaft of the tool. The motor pack can include a plurality of motors that actuate movement of a drive mechanism in the tool to effect motion of the end effector. In one embodiment, the motor pack can be removable.

In accordance with another aspect, the hyperdexterous surgical system enables the operator to interact with the patient from multiple locations, including at the patient's bedside, i.e., at the operating table, while operating the hyperdexterous surgical tools. The hyperdexterous surgical system enables the operator to control one or more hyperdexterous surgical tools, or simultaneously control a hyperdexterous surgical tool and a manual tool, at the patient's bedside while positioned next to the patient.

In accordance with another aspect, the hyperdexterous surgical system enables the operator to be mobile around the operating arena during the procedure. The mobility allows the surgeon to find the optimal position about the patient to perform a surgical procedure and to reposition him or herself during the course of a surgery as needed or desired. The hyperdexterous surgical system thus enables the operator to control a hyperdexterous surgical tool from a plurality of locations, including from the patient's bedside and/or from a separate remote stand. The operator can relocate to a more optimal position to manipulate a manual tool and/or a hyperdexterous surgical tool.

In accordance with another aspect, the hyperdexterous surgical system is modular, thereby enabling flexibility and versatility in arranging one or more hyperdexterous surgical arms of the hyperdexterous surgical system relative to the patient. Such flexibility provided by the hyperdexterous surgical system allows advantageous spacing of the hyperdexterous surgical arms. This flexibility also allows the operating arena to be set up to conform to the patient or the environment prior to beginning a surgical procedure, and to be modified during a surgical procedure, by adding or removing hyperdexterous surgical arms as needed. The flexibility provided by the modular aspect of the hyperdexterous surgical system also enables more free space around the patient, which limits collisions between one or more hyperdexterous surgical arms. Said free space also allows the surgeon greater access to the patient, for example to manipulate a manual tool from various positions (e.g., simultaneously with a hyperdexterous surgical tool) or reposition him or herself relative to the patient during a surgery, such as when emergency procedures need to be performed on the patient. Said free space provided by the hyperdexterous surgical system also allows for positioning of additional hyperdexterous surgical arms, as well as allows for greater range of motion of the hyperdexterous surgical arms.

In accordance with another aspect, the size and/or weight of the hyperdexterous surgical arm is minimized. The size and/or weight of the rotate/translate mechanism of a hyperdexterous surgical tool is minimized, which allows the size and/or weight of the hyperdexterous surgical arm that supports the hyperdexterous surgical tool to be minimized. Minimizing the size and weight of the hyperdexterous surgical arm allows the use of drive mechanisms, such as motors, that are less bulky to effect movement of the hyperdexterous surgical arm. Further, the amount of power needed to power the drive mechanism of the hyperdexterous surgical arm is reduced. Additionally, the smaller size and/or weight of the hyperdexterous surgical arm allows for flexibility in the mounting of the hyperdexterous surgical arm to a fixture. Due to the smaller space taken up by hyperdexterous surgical system, the operator can advantageously have more free space around the surgical arena.

In accordance with another aspect, the hyperdexterous surgical system facilitates the surgeon's natural understanding of the motion of the hyperdexterous surgical tools, by augmenting the surgeon's understanding of the positioning of the tools. The hyperdexterous surgical system provides information regarding the positioning of the manual tools and hyperdexterous surgical tools within the workspace, inside the body of a patient. For example, the hyperdexterous surgical system can provide visual cues to the surgeon that help the surgeon understand the orientation and position of the hyperdexterous surgical tools relative to the surgeon, allowing the surgeon to understand how the hyperdexterous surgical tools will move when actuated by the surgeon. The hyperdexterous surgical system enables the control of the hyperdexterous surgical tools to be adjusted based upon the preferences of the operator. The hyperdexterous surgical system enables the information presented to the operator to be adjusted based upon the preferences of the operator.

In accordance with another aspect, the hyperdexterous surgical system reduces the dead zone, the region within the body inaccessible by the hyperdexterous surgical tool. The hyperdexterous surgical arm can be positioned such that the dead zones can be placed away from the patient's body. The hyperdexterous surgical system can be designed such that mounting the hyperdexterous surgical arm to minimize the dead zone is easy to achieve. The hyperdexterous surgical system can be designed such that a neutral position and/or a zero position of the hyperdexterous surgical arm minimize the dead zone.

In accordance with another aspect, the hyperdexterous surgical arm can have a redundant degree of freedom. The redundant degree of freedom can allow the hyperdexterous surgical arm to be placed in a variety of desired poses. The redundant degree of freedom can enable more free space around the patient. The redundant degree of freedom can enable the placement and use of more hyperdexterous surgical arms (e.g., a plurality of hyperdexterous surgical arms), within the space above the patient. Additionally, the redundant degree of freedom can enable a larger workspace inside the patient. The redundant degree of freedom can limit the number of self-collisions (between components of a single hyperdexterous surgical arm) and other collisions (between hyperdexterous surgical arms, between hyperdexterous surgical arm and the patient).

In accordance with one aspect, the hyperdexterous surgical arm can have three degrees of freedom. The hyperdexterous surgical arm can have one redundant degree of freedom compared with on-market systems. The hyperdexterous surgical arm can have two roll axes. One of the two roll axes can be a redundant roll axis. The hyperdexterous surgical arm can have a redundant roll mechanism. The hyperdexterous surgical tool and the rotate/translate mechanism can have four degrees of freedom. The hyperdexterous surgical tool can rotate and translate. Additionally, the hyperdexterous surgical tool can pitch and roll (e.g., via a wrist). The hyperdexterous surgical arm, hyperdexterous surgical tool and rotate/translate mechanism can together provide seven degrees of freedom. In one embodiment, the hyperdexterous surgical arm, hyperdexterous surgical tool and rotate/translate mechanism can together provide more than seven degrees of freedom. The hyperdexterous surgical arm can have more than one redundant degree of freedom compared with on-market systems. The redundant degree of freedom can allow the hyperdexterous surgical arm to be placed in a variety of desired poses. Additionally, the redundant degree of freedom can allow the hyperdexterous surgical tool to be positioned in a desired orientation via a variety of poses of the hyperdexterous surgical arm.

The hyperdexterous surgical arm can be positioned to establish a Remote Center. The Remote Center is the location where entry into the body occurs. For the hyperdexterous surgical system, the Remote Center is a location in space where the axes of rotation of the various roll and pitch mechanisms of the hyperdexterous surgical arm and the axis of the hyperdexterous surgical tool intersect. The Remote Center can be located at the incision of a patient. The shoulder roll mechanism can be placed below the Remote Center to position the dead zone outside the body of the patient.

In accordance with another aspect, the hyperdexterous surgical arm can include a pitch mechanism, a first roll mechanism, and a second roll mechanism. The axis of the first and second roll mechanism can pass through the Remote Center. Additionally, an axis of a hyperdexterous surgical tool coupled to the hyperdexterous surgical arm can pass through the Remote Center. The hyperdexterous surgical arm can be arranged such that the vertical location of the second roll mechanism can be at or below the Remote Center through which all the axes pass. The second roll mechanism is the redundant roll mechanism.

The hyperdexterous surgical arm can be arranged such that the second roll mechanism can rotate at least up to +/−90° from an initial position. In some embodiments, the hyperdexterous surgical arm can be arranged such that the second roll mechanism can rotate more than +/−90° from an initial position. The second roll mechanism can advantageously reach targets that are inaccessible or difficult to reach with an on-market robotic arm having only the pitch mechanism and one roll mechanism.

Due to the arrangement of the pitch mechanism, the first roll mechanism, and the second roll mechanism, the hyperdexterous surgical arm can assume various poses. The target location may be accessed by changing the orientation of the pitch mechanism, the first roll mechanism, and/or the second roll mechanism while maintaining Remote Center.

In accordance with another aspect, the hyperdexterous surgical system includes a rotate/translate mechanism that can impart rotation and/or translation on a hyperdexterous surgical tool. The hyperdexterous surgical arm can be arranged such that the rotate/translate mechanism is located proximate the Remote Center (e.g., within 3-5 inches, within 2-6 inches, within 1-7 inches, less than 7 inches, less than 6 inches, less than 5 inches, less than 4 inches, less than 3 inches, less than 2 inches, less than 1 inch). The rotate/translate mechanism can be arranged to have a limited contribution to rotational moment of inertia of the hyperdexterous surgical arm. The rotate/translate mechanism can be arranged to limit interference with adjacent hyperdexterous surgical arms during movement. The rotate/translate mechanism can be arranged such that it acts directly on the shaft of the hyperdexterous surgical tool. The rotate/translate mechanism can be arranged such that it accommodates different size shafts of the hyperdexterous surgical tools. The rotate/translate mechanism can have a smaller width than on-market systems, allowing hyperdexterous surgical tools of adjacent hyperdexterous surgical arms to be positioned close together.

The rotate/translate mechanism can be arranged such that the mechanical energy inputs for rotation and translation can be differential such that rotation and/or translation are achieved by combined motion of the two mechanical energy inputs. The mechanical energy inputs for rotation and translation can be differential such that the power applied to the mechanism is the combined power of the two input motors. The rotate/translate mechanism can be arranged such that it maintains a barrier between sterile components of the hyperdexterous surgical system and non-sterile components of the hyperdexterous surgical system. The rotate/translate mechanism can be arranged such that the shaft position of the hyperdexterous surgical tool is measured directly on the shaft through the resistance or capacitance of the shaft length outside the body of the patient.

In accordance with another aspect, the hyperdexterous surgical system can include a control system. The hyperdexterous surgical arm can be controlled by an input device. The hyperdexterous surgical tool can be controlled by an input device. The position and orientation of the input device can be tracked. The input device can be wireless or wired. The hyperdexterous surgical system can include one or more input devices (e.g., two, three, four, five, six input devices, etc.).

The input devices can control one or more control points. The control points are locations which have the capability to execute some motion. One or more control points can be located on the hyperdexterous surgical arm. One or more control points can be located on the hyperdexterous surgical tool. The conversion of movement of the input device to movement of one or more control points may be independent of the movement of other control points. The conversion of movement of the input device to movement of one or more control points may be synchronized with the movement of other control points. The operator can control one or more control points simultaneously.

The controlled objects may be selected from the group comprising one or more hyperdexterous surgical tools and/or one or more hyperdexterous surgical arms. The control system of the hyperdexterous surgical system can convert the movement of the input device into movements of the controlled objects dependent on the zoom factor of images displayed on one or more displays.

The control system can include the application of constraints between the one or more input devices and the one or more controlled objects. The control system can be arranged such that the constraints are measured quantities such as position or derived parameters such as distance, velocity, force, and tension. The control system can be arranged such that the constraints can be different for each controlled object. The control system can be arranged such that the constraints can be the same for a group of controlled objects. Each hyperdexterous surgical tool in the set can have an independent constraint. The constraint can be that one or more hyperdexterous surgical tools can be manipulated together with a single input device.

The hyperdexterous surgical system can include an electronic control system that communicates with the one or more hyperdexterous surgical arms and/or one or more hyperdexterous surgical tools. The hyperdexterous surgical system can include one or more input devices that communicate a signal with the control system. The signal from the input devices can be transmitted within the operating arena. For example, the signal from the input devices can be transmitted from the bedside of a patient, allowing the operator to control hyperdexterous surgical arm from the bedside of a patient. The control system can communicate a signal with the one or more hyperdexterous surgical arms and/or one or more hyperdexterous surgical tools from various locations within the operating arena.

In accordance with another aspect, the hyperdexterous surgical system enables the control of a hyperdexterous surgical tool and a manual tool in frames of reference that are aligned, partially aligned or independent of each other. The hyperdexterous surgical system enables control of one or more hyperdexterous surgical tools in frames of reference that are aligned, partially aligned or independent of each other. The hyperdexterous surgical system provides information to the operator regarding the frames of references.

In accordance with another aspect, the hyperdexterous surgical system enables the movement of a hyperdexterous surgical tool to be locked to the movement of a single tool. The hyperdexterous surgical system enables the movement of one or more hyperdexterous surgical tools to be locked to the movement of a single hyperdexterous surgical tool. The hyperdexterous surgical system enables the movement of one or more hyperdexterous surgical tools to be locked to the movement of a single manual tool.

In accordance with another aspect, the hyperdexterous surgical system enables and disables motion of one or more hyperdexterous surgical tools with a mechanism. The mechanism can be a clutch. The operation of the mechanism can establish a frame of reference for the hyperdexterous surgical tool. The operation of the mechanism enables the operator to establish a new reference frame after the initial establishment of a reference frame. The hyperdexterous surgical system can be arranged such that the frame of reference may be associated with the wrist or forearm of the operator's hand that is operating the input device. The hyperdexterous surgical system can be arranged such that the frame of reference may be associated with the wrist or forearm of the operator's hand that is operating the manual tool. The operator can manipulate one or more hyperdexterous surgical tools in a frame of reference that is independent of the frame of reference of the one or more manual tools.

In accordance with another aspect, the hyperdexterous surgical system facilitates an understanding of the frames of references. The hyperdexterous surgical system can include a visualization system that aggregates information from one or more sources and provides one or more images to the surgeon. The information may be positional information of the surgeon, the patient, the hyperdexterous surgical arm, the hyperdexterous surgical tool, and/or the manual tool. The information may be positional information of control points. The image can be manipulated to reflect the point of view of the surgeon. The image can be updated to reflect the point of view of the surgeon as the surgeon moves to another location.

The information presented by the visualization system may be live data from the cameras, data from pre-operative MRI, CT, ultrasound or other imaging modality, and models of organs and other parts of the human body. The visualization system can be arranged such that the image can be updated in real time as data from cameras is received. The visualization system can be arranged such that the image can be a blend of information from various sources. The blending and the types of information to blend may depend on the zoom factor. The image can be updated to display warnings related to the information (e.g., non-real-time, not precisely aligned models, low-resolution data).

The visualization system can present an image on one or more displays. The image displayed on each display may be different. Each display may present different images (e.g., the location of the patient, the location of control points). The visualization system can be arranged such that the images can be adjusted automatically dependent on the type of manipulation being performed. The visualization system can be arranged such that the images may be rotated and oriented according to the surgeon's location. The visualization system can be arranged such that during the zooming operation, the images can be blended to transition smoothly between a zoomed in image and a zoomed out image. The images may be controlled by the user input devices.

BRIEF DESCRIPTION OF THE DRAWINGS

FIG. 32B is an embodiment of an input device.

FIG. 39 schematically illustrates a method of using the hyperdexterous surgical tools and a manual tool at the same time.

DETAILED DESCRIPTION

Figure 1A:
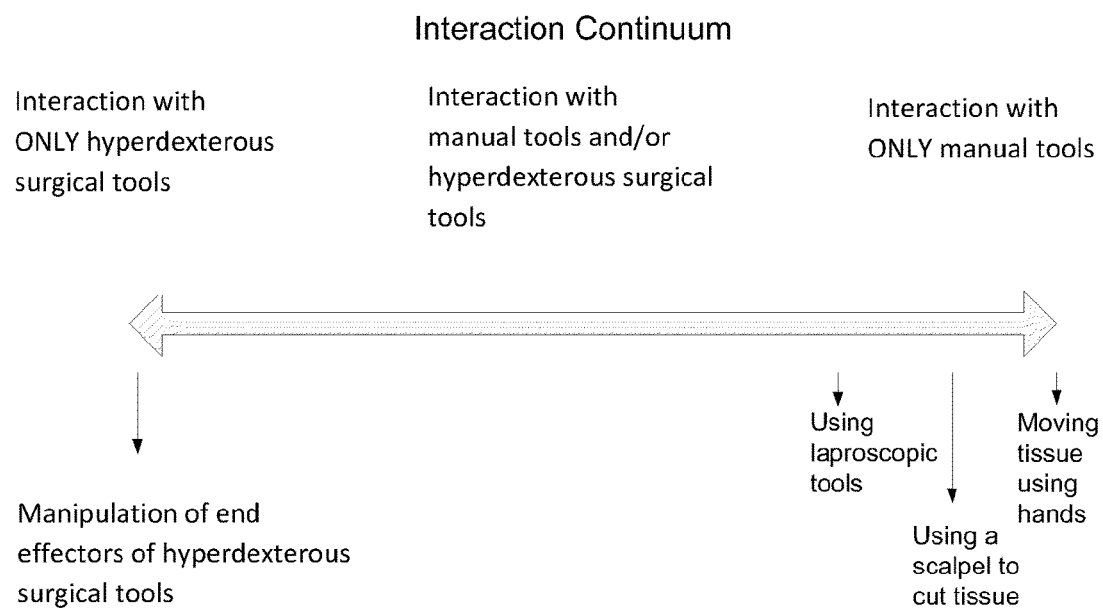
FIG. 1A schematically illustrates an interaction continuum.

The term "hyperdexterous" is a combination of the ordinary meaning of "hyper" and "dexterous"; hyper meaning over or above, and dexterous meaning skillful or adroit in the use of the hands or body. A hyperdexterous surgical system as used herein enables interactions between a surgeon and the patient along an interaction continuum, as further described below, and provides increased versatility with respect to the surgical procedures that can be performed. The hyperdexterous surgical system enhances the ability of the surgeon to interact with a patient and includes several features which combine to produce a more natural, more interactive, and more versatile surgical system. The versatility of the hyperdexterous surgical system is illustrated by various aspects of the system, such as for example its modularity, which allows the use of one or more hyperdexterous surgical arms and to move the hyperdexterous surgical arm out of the way to utilize only manual surgical tools, its enabling of the surgeon to be mobile in the surgical arena during a surgical procedure, and its enabling of the surgeon to simultaneously operate a hyperdexterous surgical tool and a manual tool while being able to maneuver between multiple bedside locations of the patient to an optimal position for a particular surgical task. With this feature, and with other features to be described below, a hyperdexterous surgical system has more versatility than on-market purely "robotic" surgical systems.

The nature of the hyperdexterous surgical system is illustrated, among other ways, by providing the surgeon with a variety of information (e.g., via displays) that allow the surgeon to readily understand the positioning of the hyperdexterous surgical tools relative to the patient so as to naturally understand how the tools will move when actuated. The interactive nature of the hyperdexterous surgical system is illustrated, among other things, by the ability of the surgeon to selectively control a plurality of hyperdexterous surgical tools with user input devices, as well as the ability to move between different frames of reference during a surgical procedure (e.g., between an immersive frame of reference inside the patient's body and a frame of reference outside the patient's body), allowing the surgeon to reposition himself or herself during a procedure, all the while remaining aware of the position and orientation of the tools relative to the surgeon.

Introduction

The hyperdexterous surgical system described herein provides a fundamentally different conceptual framework from existing on-market robotic surgical systems in that, among other things, it enables a surgeon to simultaneously use manual and hyperdexterous surgical tools while at the patient's bedside. This ability to be at the patient's bedside, i.e., beside the operating table, provides several advantages: from improved communication with the surgical team; to direct monitoring of the patient; to facilitating tool exchanges (e.g., between manual and hyperdexterous surgical tools). Moreover, the hyperdexterous surgical system, as discussed below, includes several subsystems that together provide a flexible, more natural, and more interactive system that advantageously allows surgeons to perform surgical procedures seamlessly along an interaction continuum between using only hyperdexterous surgical tools, simultaneously using a combination of manual and hyperdexterous surgical tools, and using only manual tools as desired by the surgeon or required by the surgical task.

One advantageous aspect of the hyperdexterous surgical system is the size of the hyperdexterous surgical arm, which is smaller and more compact than those of on-market systems, and which allows increased flexibility in how the arm is mounted relative to the patient—whether on a cart, or dolly, or wall or ceiling of the operating room, or directly to the patient's bed. The smaller size of the hyperdexterous surgical arm also allows for the hyperdexterous surgical system to be modular, where the number of hyperdexterous surgical arms used can vary as desired by the surgeon depending on the surgical need. The small size of the hyperdexterous surgical arms additionally provide for increased free space above the patient, which facilitates the surgeon's ability to work from a bedside location. Indeed, as noted above, one inventive aspect of the hyperdexterous surgical system is that it allows the surgeon to operate along an interaction continuum, and in one scenario the surgeon can move the hyperdexterous surgical arms out of the way and use only manual tools. This ability to maximize the free space (e.g., move the hyperdexterous surgical arms out of the way, small size of the arm), is enhanced by advantageously providing a hyperdexterous surgical arm with three degrees of freedom including a redundant roll, as discussed in more detail below. Additionally, the redundant roll of the hyperdexterous surgical arm is advantageously positioned so as to ensure that a dead zone for the hyperdexterous surgical tool is located outside the body of the patient, thereby allowing for increased access of the hyperdexterous surgical tool within the workspace in the body.

Further, the rotation and translation mechanism for the hyperdexterous surgical tool advantageously facilitates the small size of the hyperdexterous surgical arm, as discussed below. Indeed, the rotate/translate system is smaller in diameter, lighter and more compact than mechanisms that impart rotation and translation for on-market systems, which allows the hyperdexterous surgical arm that supports the rotate/translate mechanism to be smaller.

Another advantageous and interrelated aspect of the hyperdexterous surgical system is the ability it provides to the surgeon to move around freely and position him or herself in an optimal position near the patient. This ability is provided by the hyperdexterous surgical system in several ways, including allowing the surgeon to control the hyperdexterous surgical arm with one or more handheld portable input devices that communicate the movements of the surgeon's hands to a control system that controls the operation of the hyperdexterous surgical arm and hyperdexterous surgical tool. In one embodiment, the handheld portable input devices are wireless. The hyperdexterous surgical system advantageously provides for tracking of the handheld portable input devices, as well as features (e.g., a clutch) to prevent unintended motion of the hyperdexterous surgical arms or hyperdexterous surgical tools due to movements of the surgeon.

Still another advantageous and interrelated part of the hyperdexterous surgical system is the control system, which communicates the surgeon's commands (e.g., via the user input devices) to the hyperdexterous surgical tools and hyperdexterous surgical arms and facilitates how the surgeon interacts with the hyperdexterous surgical tools and hyperdexterous surgical arms. Another advantageous and interrelated part of the system is the visualization system, which aids the surgeon in manipulating the hyperdexterous surgical tools within the patient's body from various frames of reference (e.g., immersive, bird's eye view outside the patient's body). The control system and visualization system may work together to enhance the surgeon's ability in performing a surgical procedure by providing a variety of information (e.g., visual cues) that allows the surgeon to naturally recognize the positioning of the hyperdexterous surgical tools and manual tools.

Each of the components or subsystems of the hyperdexterous surgical system have advantages over corresponding components in on-market systems. Additionally, taken together the components and subsystems provide a hyperdexterous surgical system that provides a completely different paradigm for surgical procedures that enhances the ability of the surgeon to interact with a patient in a more natural, more interactive, and more flexible manner. The hyperdexterous surgical system will now be described in more detail.

FIG. 1A shows the interaction continuum of the hyperdexterous surgical system. The right end of the continuum illustrates physical interactions between the body of the surgeon and the body of the patient. The far right end of the continuum includes the surgeon moving tissue by hand. The use of a manual tool such as a scalpel is less physically interactive than moving tissue by hand. The use of a laparoscopic tool such as a scalpel is less physically interactive than moving tissue by hand. The left end of the continuum illustrates the use of a hyperdexterous surgical arm to control end effectors. Along the continuum, the operator can use manual tools and/or hyperdexterous tools in various combinations. The hyperdexterous surgical system enables an operator 1, such as a surgeon, to work anywhere along the continuum.

At the right end of the continuum, the surgeon is in close proximity to the patient in order to physically manipulate the tissue. The surgeon is able to directly touch and feel tissue at the surgical site. At the left end of the continuum, the surgeon interacts with the patient remotely by manipulating user input devices that serve as proxies for the real tools. The surgeon manipulates end-effectors such as graspers by manipulating user input devices. Many scenarios occur along the interaction continuum.

Embodiments herein describe the use of a hyperdexterous surgical system that can be used by an operator. The operator may be a surgeon, a medical assistant, staff, medical examiners, or any other person operating the hyperdexterous surgical system. An operator is not limited to a medical professional qualified to practice surgery, but includes any operator trained to operate the hyperdexterous surgical system.

Figure 1B:
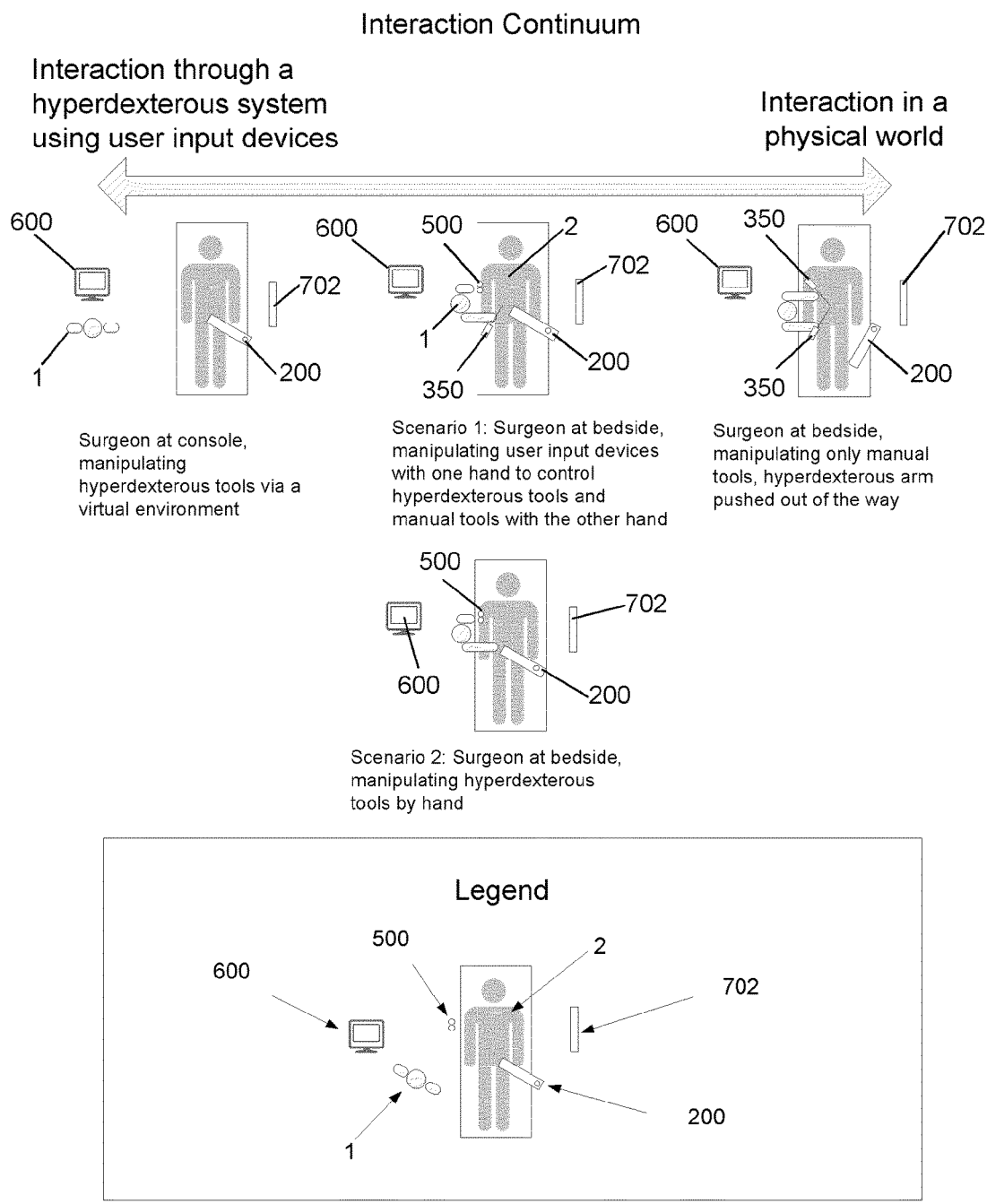
FIG. 1B schematically illustrates scenarios along the interaction continuum.

FIG. 1B replicates the interactive continuum of FIG. 1A in more detail. FIG. 1B shows various methods of using a hyperdexterous surgical system, such as the hyperdexterous surgical system 100 shown in FIG. 2. On the right side of FIG. 1B, an operator 1 may perform a surgical step with manual tools 350. In this scenario, a hyperdexterous surgical arm 200 of the hyperdexterous surgical system 100 may be moved away from the work space. The operator 1 may refer to a display 702 which provides images of the surgery. On the left side of FIG. 1B, the operator 1 interacts with an input device 500 to control the hyperdexterous surgical arm 200. The operator 1 may refer to a display 600 which provides images of the surgery.

Figure 2:
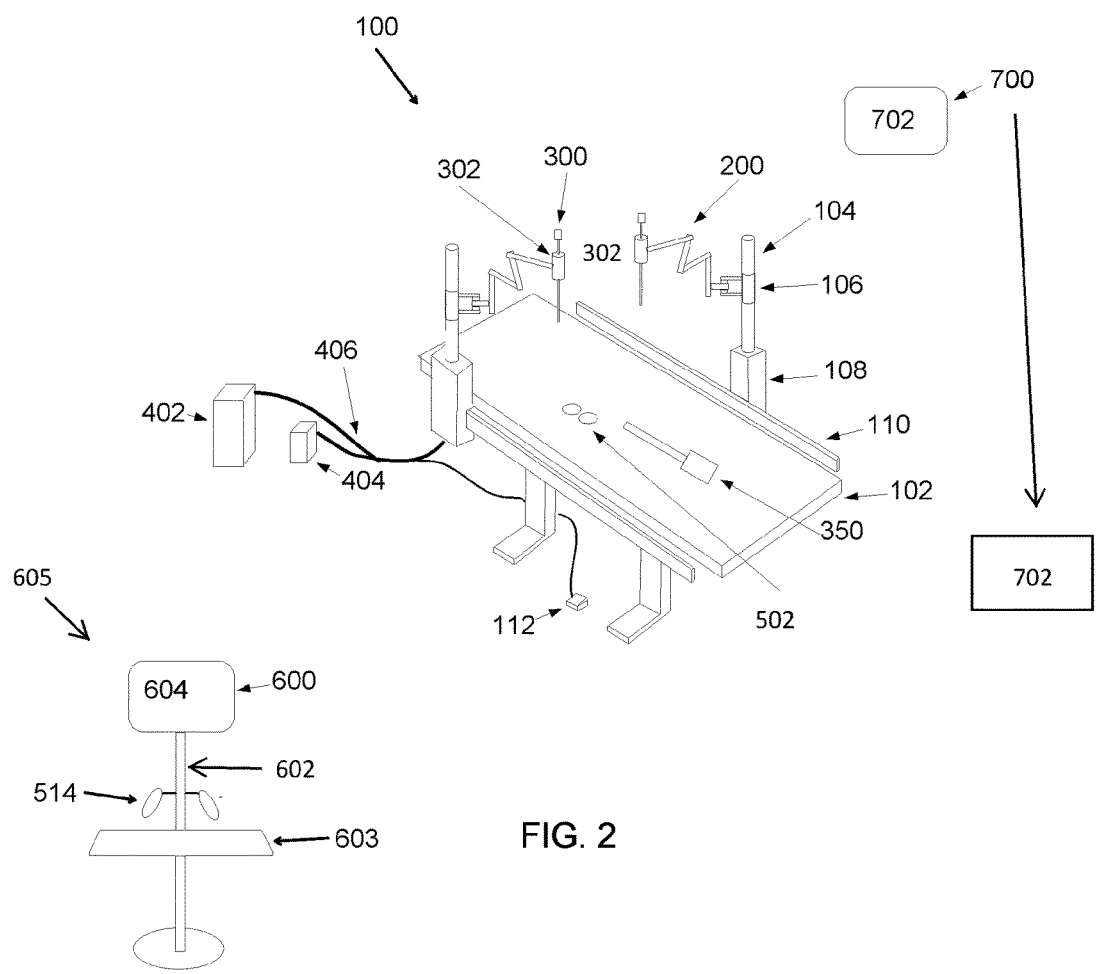
FIG. 2 schematically illustrates one embodiment of a hyperdexterous surgical system.

In the middle of this continuum, different scenarios may occur. One scenario is illustrated as Scenario 1 in FIG. 1B. In this scenario, the operator 1 may simultaneously use one or more hyperdexterous surgical tools 300 and one or more manual tools 350 (e.g., at the same time, in the same workspace). The surgeon can manipulate one or more of the hyperdexterous surgical tools 300 with one or more of the input devices 500. The operator 1 may refer to a display 702 which provides images of the surgery. Another scenario is illustrated as Scenario 2 in FIG. 1B. In this scenario, the operator 1 may manipulate the hyperdexterous surgical arm 200 by hand. This scenario may occur for example when executing large scale motions of the hyperdexterous surgical arms 200. Though FIG. 1B shows only one hyperdexterous surgical arm 200, the hyperdexterous surgical system 100 can have a plurality of hyperdexterous surgical arms 200, as shown in FIG. 2.

In another scenarios, not shown, the operator 1 can insert the manual tool 350 into a trocar 302 (shown in FIG. 2) supported by the hyperdexterous surgical arm 200. The trocar 302, with the manual tool 350 inserted therein, may be manipulated by hand. The third scenario may be useful when it may be difficult to maneuver the manual tool 350 only with the hands. Some examples where such situations may be encountered is when the patient is obese or if the angle of entry into the patient is awkward. In such situations the hyperdexterous surgical arm 200 holding the trocar 302 may act as a power assist to position the manual tool 350. In other words, the hyperdexterous surgical arm 200 holding the trocar 302 may counter the forces that are applied on the manual tool 350 by the patient's body, and can enhance maneuverability of the manual tool 350. The versatility of the hyperdexterous surgical system 100 advantageously allows all such combinations.

Figure 3A:
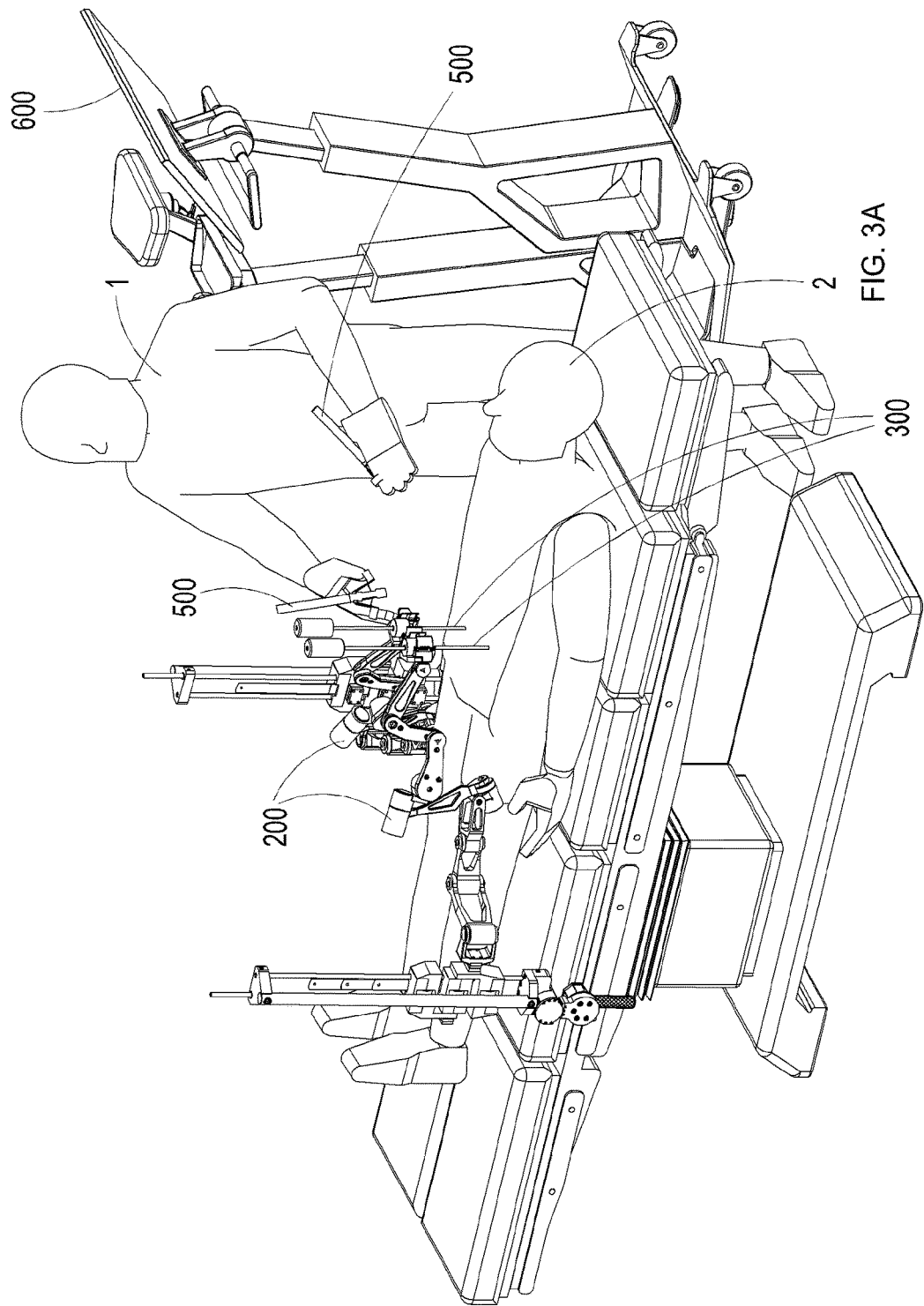
FIG. 3A-C schematically illustrates scenarios along the interaction continuum.
Figure 3B:
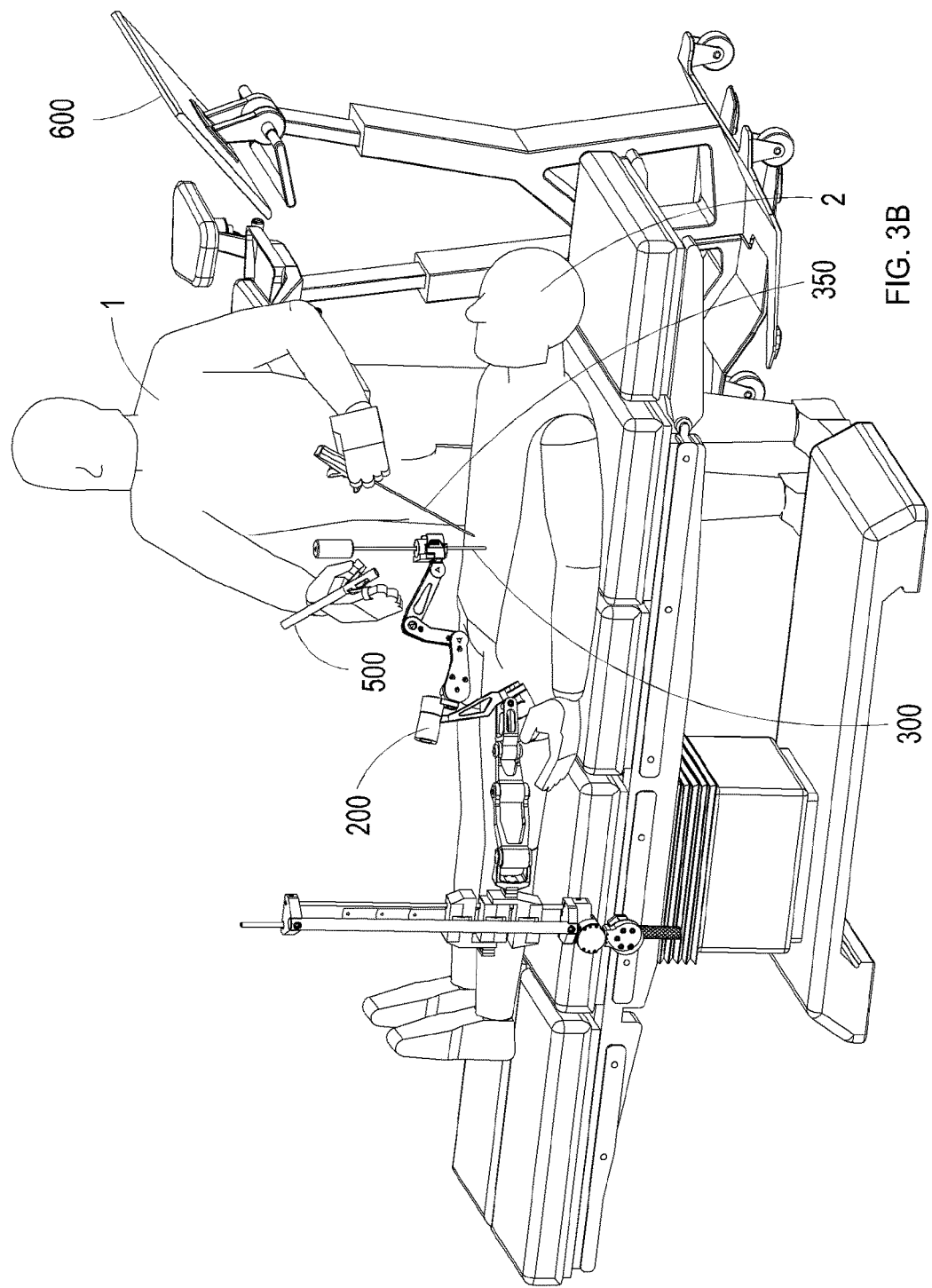
Figure 3C:
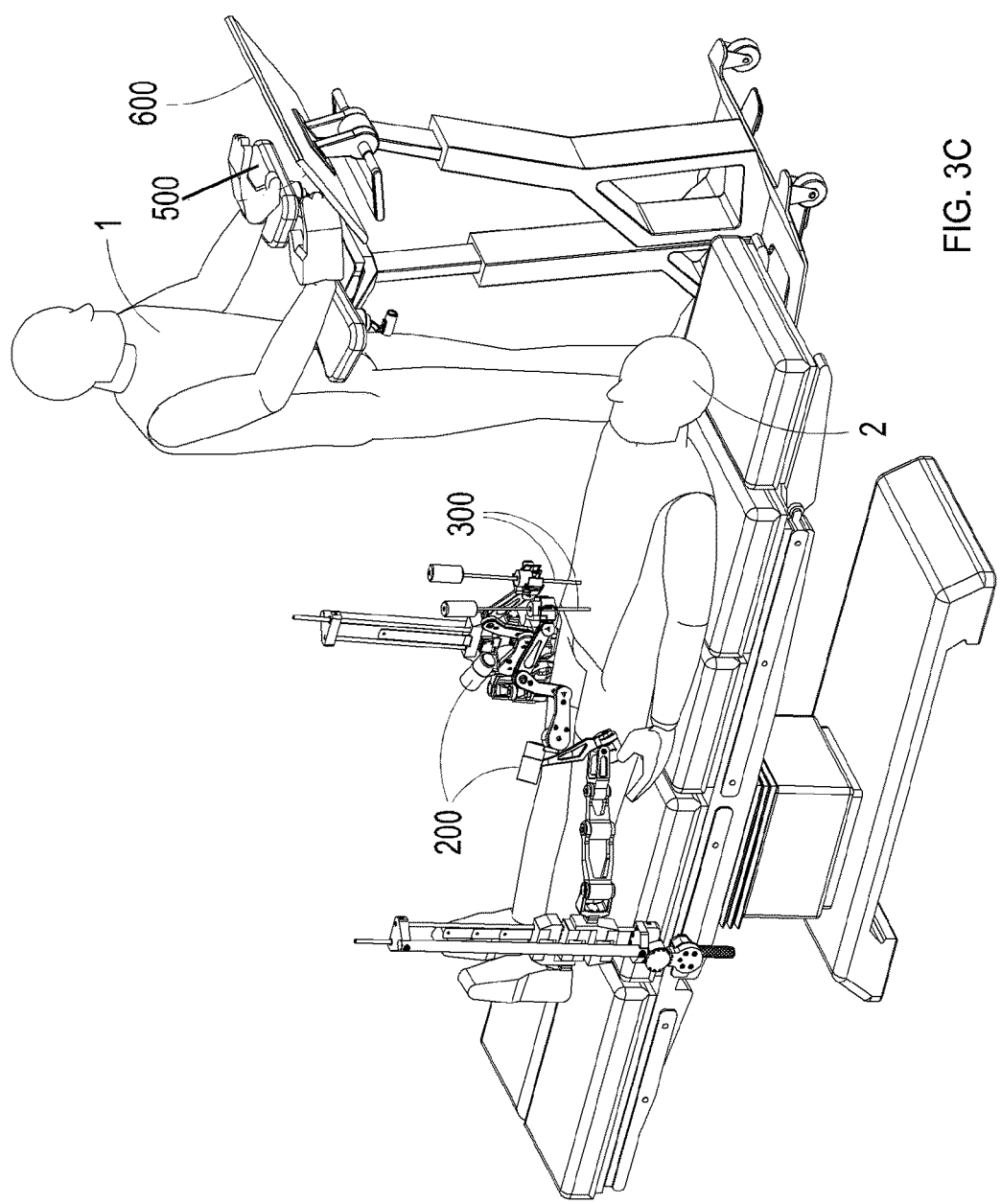

FIGS. 3A-3C shows scenarios wherein the operator 1 selects the type of tools to be used in a surgical procedure. FIG. 3B is similar to Scenario 1 and FIG. 3C is similar to the left side of the continuum shown in FIG. 1B. The figures show three dimensional depiction of use the hyperdexterous surgical system 100 during a surgical procedure on a patient 2.

In FIG. 3A, the hyperdexterous surgical system 100 includes two hyperdexterous surgical arms 200, each coupled to a hyperdexterous surgical tool 300. The operator 1 controls a hyperdexterous surgical arm 200 with an input device 500 held in his right hand. The operator 1 controls another hyperdexterous surgical arm 200 with an input device 500 held in his left hand. The input devices 500 move the hyperdexterous surgical arms 200 and/or the hyperdexterous surgical tools 300 in response to the operator's 1 movement. The hyperdexterous surgical system 100 includes a display 600. The display 600 may allow the operator 1 to establish constraints to be applied to the hyperdexterous surgical system 100. For example, the display 600 may allow the operator 1 to establish associations (e.g., a pairing) between the input devices 500 and the controlled objects (e.g., the hyperdexterous surgical arms 200 and/or the hyperdexterous surgical tools 300). The display 600 may provide images of the surgery.

In FIG. 3B, the hyperdexterous surgical system 100 includes a hyperdexterous surgical arm 200 coupled to a hyperdexterous surgical tool 300. The operator 1 controls the hyperdexterous surgical arm 200 with an input device 500 held in his right hand. The input device 500 moves the hyperdexterous surgical arm 200 and/or the hyperdexterous surgical tool 300 in response to the operator's 1 movement. The operator 1 controls a manual tool 350 with his left hand. As illustrated in FIG. 3B and discussed herein, the hyperdexterous surgical system 100 advantageously enables the operator 1 (e.g., surgeon) to simultaneously control a hyperdexterous surgical tool 300 and a manual tool 350.

In FIG. 3C, the hyperdexterous surgical system 100 includes two hyperdexterous surgical arms 200, each coupled to a hyperdexterous surgical tool 300. The operator 1 can control the hyperdexterous surgical arms 200 with one or more input devices 500. The input devices 500 can be the input devices shown in FIG. 3A. The input devices 500 can be controllers as shown in FIG. 3C. The one or more input devices 500 can be mounted or otherwise fixed near the display 600. In another embodiment, the one or more input devices 500 can be handheld portable input devices, such as those shown in FIG. 3A, and the operator 1 can support his or her arms on a support bar or rest bar of the stand while standing or sitting at the stand and operating the handheld portable input devices. Like the input devices 500 shown in FIG. 3A, the one or more input devices 500 shown in FIG. 3C moves the hyperdexterous surgical arms 200 and/or the hyperdexterous surgical tools 300 in response to the operator's 1 movement.

System Overview

The hyperdexterous surgical system 100 can include many components that can work together to achieve benefits described herein, such as enhancing the ability of the surgeon to interact with the patient by providing a more natural, more interactive, and more versatile surgical system. The hyperdexterous surgical system 100 can include one or more hyperdexterous surgical arms 200, and each hyperdexterous surgical arms 200 can manipulate a hyperdexterous surgical tool 300. The hyperdexterous surgical system 100 includes a control system and displays 600, 702 which provide the operator with visual cues that aid the surgeon in controlling the operation of the one or more hyperdexterous surgical tools 300 and the manual tools 350. The operator, such as a surgeon can optionally manipulate the hyperdexterous surgical tool 300 and the manual tools 350 simultaneously at various locations in the operating arena.

FIG. 2 shows one embodiment of a hyperdexterous surgical system 100. The hyperdexterous surgical system 100 includes one or more hyperdexterous surgical arms 200. Each hyperdexterous surgical arm 200 can support a hyperdexterous surgical tool 300 (e.g., via a trocar 302). The hyperdexterous surgical system 100 can include one or more manual tools 350. The manual tool 350 can be used simultaneously with the hyperdexterous surgical tool 300 by the operator (e.g., surgeon). The hyperdexterous surgical tool 300 can be controlled by an input device 500. The input device 500 can take many forms including a pincher 502 (see FIG. 32A) and a controller 514.

The hyperdexterous surgical system 100 can include a control system to translate movements from the input devices 500 to movements of the hyperdexterous surgical arms 200 and hyperdexterous surgical tool 300. The operator 1 can select which input device 500 controls which hyperdexterous surgical tool 300 or hyperdexterous surgical arms 200. The control system 400 can include a computer 402, one or more cables 406 and/or a power supply 404.

The hyperdexterous surgical arm 200 can be coupled with a fixture (e.g., operating table, hospital bed, examination table, wall, floor, ceiling, table, cart, dolly). In one embodiment, where the fixture is a cart or dolly, the fixture can be anchored (e.g., temporarily) to the floor. The hyperdexterous surgical system 100 may include mechanisms that couple or hold the hyperdexterous surgical arm 200 to the fixture. In the embodiment of FIG. 2, the fixture is a bed or operating table 102.

Figure 34:
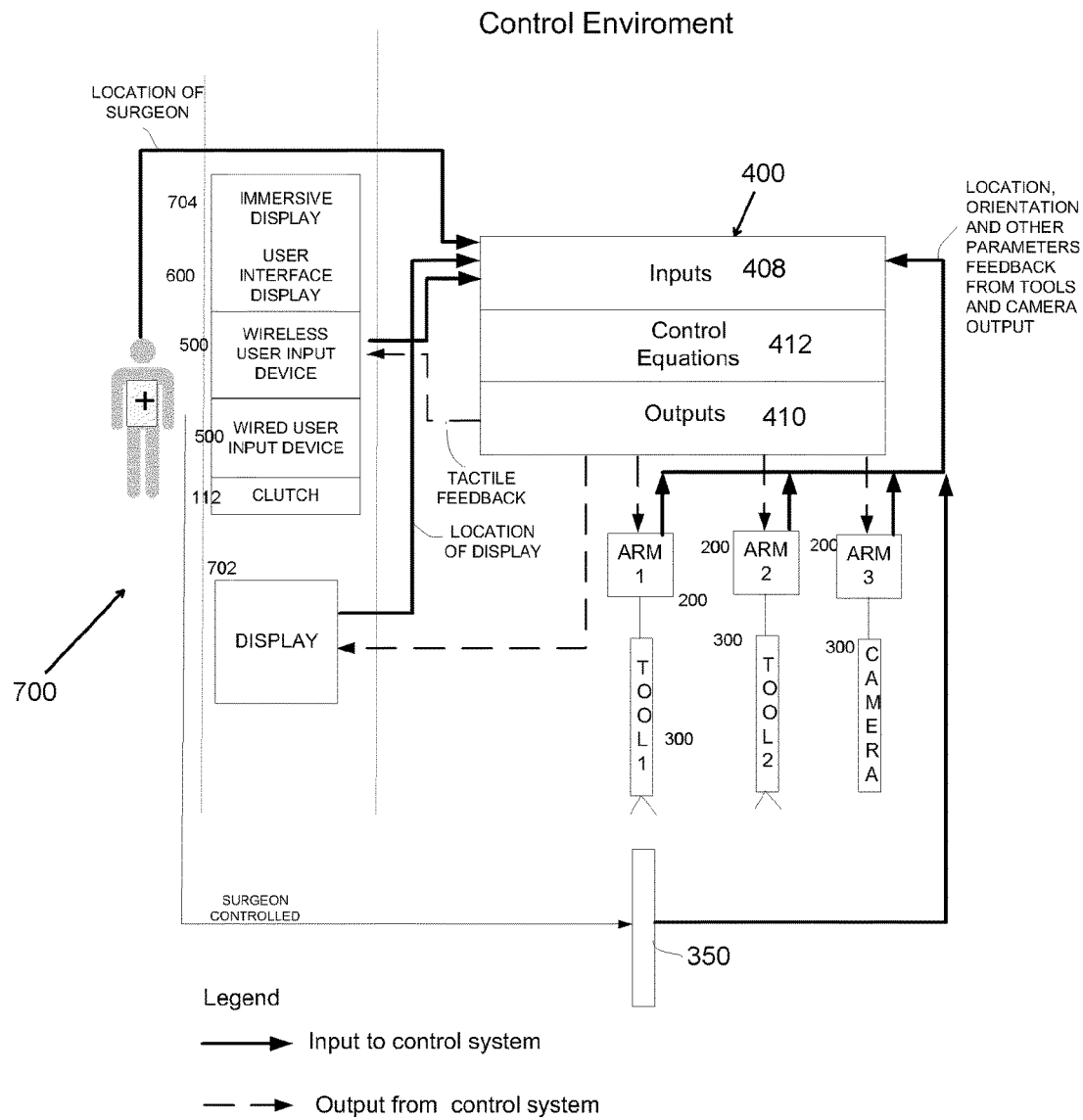
FIG. 34 schematically illustrates an embodiment of a control system of a hyperdexterous surgical system.
Figure 35:
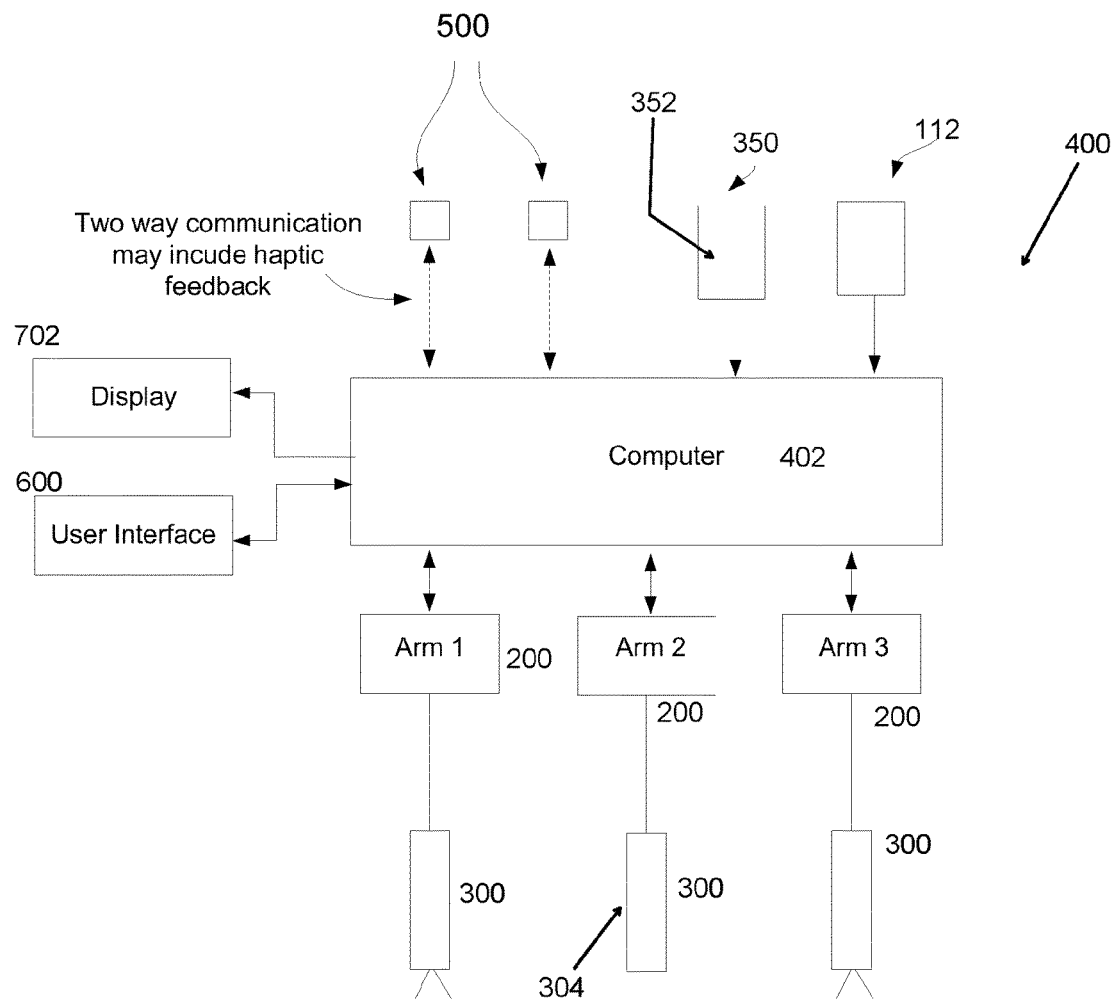
FIG. 35 schematically illustrates a block diagram of a control system.

The hyperdexterous surgical arm 200 and the hyperdexterous surgical tool 300 can be controlled by a control system 400, a schematic of which is shown in FIGS. 34-35. The algorithms that guide the control system and/or any computations performed by the control system may be stored by the computer 402. The control system 400 can translate user commands to motion of the hyperdexterous surgical arm 200 and/or motions of the hyperdexterous surgical tool 300. The computer 402 may be connected to the power supply 404. The computer 402 may be connected to a clutch 112 which may take the form of a foot pedal. The computer 402 may include cables 406 that connect the computer 402 to other components.

The hyperdexterous surgical system 100 can include one or more input devices 500. The input device 500 can communicate with the control system 400, either through a wired or wireless connection. As used in embodiments herein, the term "wireless" encompasses all forms of wireless communication, including, but not limited to, infrared (IR), radiofrequency (RF), microwave, and ultrasonic. The input device 500 can send control signals to the appropriate motors within the hyperdexterous surgical arm 200 and the hyperdexterous surgical tools 300 via the control system 400 (e.g., by communicating a signal from a transmitter in the input device 500 to a receiver of the control system 400). The input devices 500 can be handheld and/or portable devices that advantageously allow the operator 1, such as a surgeon, to move about the bedside of the patient 2 during a procedure. The input devices 500 can allow the operator 1 to control the hyperdexterous surgical arm 200 and/or the hyperdexterous surgical tools 300 from one or more locations (e.g., a plurality of locations). Some of the locations may be at the bedside of a patient 2. The hyperdexterous surgical system 100 can include the clutch 112. The clutch 112 can be used to engage or disengage one or more hyperdexterous surgical tools 300. The clutch 112 can be a foot pedal, as shown in FIG. 2.

With continued reference to FIG. 2, the hyperdexterous surgical system 100 can include a user interface sub-system 605. The user interface sub-system 605 can include an input device (e.g., controller 514). The user interface sub-system 605 can include a platform 602 which can include features such as a horizontal resting bar 603. The user interface sub-system 605 can include a display 600. The display 600 can include a touch screen 604. The display 600 can be interactive and receive an input from the operator 1. The display 600 can be used to control the control system 400. The display 600 can be located remotely from the patient. In some embodiments, the display 600 is mounted onto the platform 602, as shown in FIG. 2. In some embodiments, the display 600 can be affixed to the body of the operator 1, such as the surgeon.

In some embodiments, the user interface sub-system 605 can include an input device 500 (e.g., a wired controller). The input device 500 may be a controller 514 mounted to the platform 602. The user interface sub-system 605 allows an operator 1, such as a surgeon, to control the input device 500 in close proximity to the display 600, as shown in FIG. 2.

The display 600 allows the operator 1 to perform many functions including pairing a hyperdexterous surgical tool 300 with an input device 500 so that the operator 1 can operate the paired hyperdexterous surgical tool 300 with the input device 500. The display 600 can allow the operator 1 to control one or more hyperdexterous surgical tools 300 with the one or more input devices 500. The display 600 also allows the operator 1, such as a surgeon, to pair a hyperdexterous surgical arm 200 with an input device 500 so that the operator 1 can operate the paired hyperdexterous surgical arm 200 with the input device 500. The display 600 can allow the operator 1 to control one or more hyperdexterous surgical arms 200. The user interface 600 can show or illustrate a map of the one or more input devices 500 and the one or more controlled objects, such as the one or more hyperdexterous surgical arms 200 or hyperdexterous surgical tools 300.

With continued reference to FIG. 2, a visualization system 700 can include one or more displays 702. The display 702 can display information about the one or more hyperdexterous surgical arms 200, the one or more hyperdexterous surgical tools 300, the patient, or any other information that may be relevant to the surgeon or surgical team. The display 702 can show images as seen by a camera 304 (shown schematically in FIG. 35) or other visualization devices, such as images of the hyperdexterous surgical tools 300 that are held by the hyperdexterous surgical arms 200, or images of a manual tool 350 held by the operator (e.g., surgeon). The camera 304 can be controlled by the control system 400. The camera 304 can be considered a hyperdexterous surgical tool 300 and moved by a hyperdexterous robotic arm 200. In one embodiment, the camera 304 can be controlled by the input device 500 via the control system 400, which enables the operator 1, such as the surgeon, to position the camera 304 as needed. The hyperdexterous surgical system 100 can include multiple displays 702 positioned at various locations throughout the operating arena. Additionally, the displays 600, 702 can show the same information or different information.

As shown in FIG. 2, the hyperdexterous surgical system 100 can be used with one or more manual tools 350 (e.g., a plurality of manual tools 350). One manual tool 350 is shown in FIG. 2. The manual tool 350 can be utilized in the same work space as the one or more hyperdexterous surgical tools 300. One or more manual tools 350 can be used because the hyperdexterous surgical system 100 advantageously allows the operator 1 to stand right by the patient 2, as discussed previously. One or more manual tools 350 can be used because the hyperdexterous surgical arm 200 is compact, thereby freeing up the space around the patient 2. The redundant roll mechanism and the placement of the redundant roll mechanism, described herein, also maximizes the free space around the patient 2. Therefore, the operator 1 can simultaneously manipulate hyperdexterous surgical tools 300 and manual tools 350 without colliding into other components of the hyperdexterous surgical system 100. The operator 1, not shown in FIG. 2, may stand by the bedside, and have the ability to choose to control one or more hyperdexterous surgical tools 300 (e.g., via the input devices 500), one or more manual tools 350, or any combination of hyperdexterous surgical tools 300 and manual tools 350.

As shown in FIG. 2, the hyperdexterous surgical arm 200 can be coupled to a hyperdexterous surgical tool 300. Accordingly, the system 100 can have one or more (e.g. a plurality) of hyperdexterous surgical arms 200 and one or more (e.g. a plurality) of hyperdexterous surgical tools 300. In some embodiments, the hyperdexterous surgical tool 300 is inserted into a trocar 302. The trocar 302 can be coupled to the hyperdexterous surgical arm 200 (e.g., affixed, integrally formed with, held by, etc.). The hyperdexterous surgical arm 200 can support and manipulate the hyperdexterous surgical tools 300 through the trocar 302. In some embodiments, the one or more hyperdexterous surgical arms 200 can insert one or more hyperdexterous surgical tools 300 through an incision in a patient 2, as shown in FIGS. 3A-C. The hyperdexterous surgical arm 200 and the hyperdexterous surgical tool 300 can have one or more motors (e.g., electrical motors) at various locations, as discussed further below. The motors facilitate the placement of the hyperdexterous surgical tools 300 appropriately in the operating work space, inside the patient 2. The hyperdexterous surgical arm 200 and the hyperdexterous surgical tool 300 can be powered by the power supply 404. In some embodiments, the one or more hyperdexterous surgical tools 300 can be disposable. In some embodiments, at least a portion of the hyperdexterous surgical tools 300 can be capable of being sterilized (e.g., reusable).

Mounting the Hyperdexterous Surgical Arm

The hyperdexterous surgical system 100 can provide a mounting to support the hyperdexterous surgical arm 200. The mounting enables the positioning of the hyperdexterous surgical arm 200 and/or the hyperdexterous surgical tools 300 relative to the patient. The hyperdexterous surgical arm 200 can be mounted to a number of fixtures, which may be movable or fixed. The flexibility in mounting the hyperdexterous surgical arm 200 and/or the hyperdexterous surgical tools 300 provides versatility in designing the operating arena and the free space outside the patient.

Figure 4:
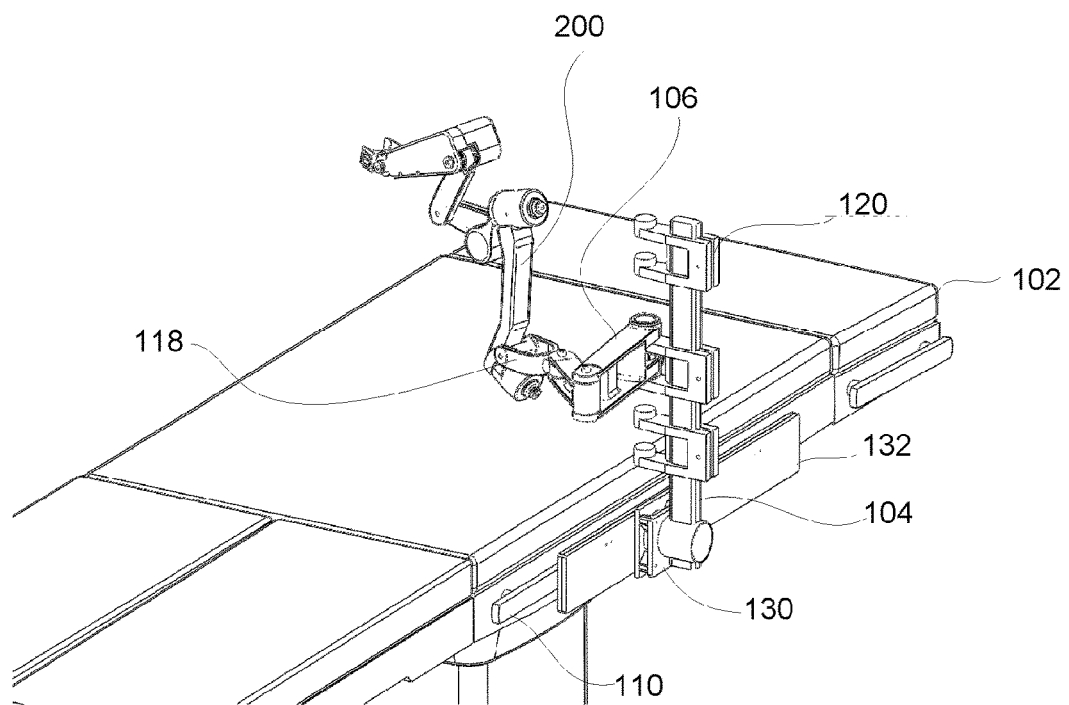
FIG. 4 schematically illustrates a hyperdexterous surgical arm coupled to a bed.

FIGS. 2 and 4 show embodiments of the hyperdexterous surgical arm 200 mounted to a fixture. The various components allow the hyperdexterous surgical arm 200 to be positioned relative to the patient 2. The various components also allow the hyperdexterous surgical arm 200 to avoid collisions with other hyperdexterous surgical arms 200. The hyperdexterous surgical arm 200 can be positioned to facilitate access to the patient 2. The hyperdexterous surgical arm 200 can be positioned to permit the operator 1 to use hyperdexterous surgical tools 300 and manual tools 350 simultaneously. The flexibility of the hyperdexterous surgical system 100 including the support arm 106, the elevator 120, and the carriage 130 allows the positioning of a Remote Center 250 (see FIG. 7) for the hyperdexterous surgical arm 200. Once the Remote Center 250 is established, the hyperdexterous surgical arm 200 can be manipulated while maintaining the Remote Center 250.

As shown in FIG. 2, the hyperdexterous surgical system 100 can include a plurality of mounting poles 104. The hyperdexterous surgical system can include any number of mounting poles 104 (e.g., one, three, four, etc.), but two are shown in FIG. 2 for illustrative purposes. Each mounting pole 104 can support a hyperdexterous surgical arm 200. FIG. 2 shows each mounting pole 104 only holding one hyperdexterous surgical arm 200, but each mounting pole 104 can optionally support any number of hyperdexterous surgical arms 200 (e.g., one, two, three, four, etc.). The hyperdexterous surgical system 100 is advantageously modular in nature. This modularity allows the users, such as a surgical team, to configure the hyperdexterous surgical system 100 most efficiently for the type of procedure being performed. Such modularity also allows the team to add or remove mounting poles 104 and/or hyperdexterous surgical arms 200 during a surgery. The modularity permits the hyperdexterous surgical system 100 to be configured in various ways.

The mounting pole 104 may be supported by a movable fixture (e.g., a dolly, a hand-truck or a small cart). The mounting pole 104, and all associated hyperdexterous surgical arms 200 and support arms 106, may be mounted to the moveable fixture at a location remote from the operating arena. The movable fixture may be transported into the operating arena before or during the surgery. If additional hyperdexterous surgical arms 200 are needed during surgery, the hyperdexterous surgical arm 200 can be mounted quickly and easily onto the fixture. In some embodiments, if additional hyperdexterous surgical arms 200 are needed during surgery, additional hyperdexterous surgical arms 200 mounted on movable fixtures may be transported into the operating arena. The moveable fixture and/or the mounting pole can be anchored to another fixture (e.g., the floor) to enhance stability. The mounting pole 104 may be supported by an immobile fixture (e.g., bed, floor, wall, or ceiling).

The mounting pole 104 can be attached to a clamp 108, as shown in FIG. 2. The clamp 108 can be connected to the fixture. In the illustrated embodiment, the fixture is a bed 102, though as discussed above, other suitable fixtures can be used. In some embodiments, the clamp 108 can be coupled to one or more rails 110 of the bed 102. Other attaching mechanisms are possible. The mounting pole 104 may be placed substantially vertically (e.g., at ninety degrees) relative to the fixture (e.g., bed 102). The mounting pole 104 may be placed at other angles, such as 15 degrees, 30 degrees, 45 degrees, 60 degrees, relative to the fixture (e.g., bed 102). The mounting pole 104 can be placed at other angles based on the orientation of the patient.

The hyperdexterous surgical arm 200 can be directly or indirectly attached to the fixture (e.g., bed 102). In one embodiment, the mounting pole and/or the support arm 106 is excluded and the hyperdexterous surgical arm 200 can be coupled directly to the mounting pole 104 or to a portion of the fixture (e.g., bed 102). In some embodiments, the hyperdexterous surgical system 100 can be detached from the fixture (e.g., bed 102 and/or rail 110).

Referring to FIG. 4, the mounting pole 104 can be coupled to components that permit horizontal movement (e.g., parallel to the bed 102) or vertical movement (e.g., perpendicular to the bed 102). The elevator 120 allows the placement of the support arm 106 and/or the hyperdexterous surgical arm 200 along the length of the mounting pole 104. One or more elevators 120 may be coupled to the mounting pole 104, as shown. Each elevator 120 may be connected to an additional support arm 106 and/or an additional hyperdexterous surgical arm 200. Accordingly, the mounting pole 104 can optionally support multiple support arms 106, each support arm 106 coupled to a hyperdexterous surgical arm 200. The elevators 120 may provide alternative vertical locations at which the hyperdexterous surgical arm 200 may be coupled to the mounting pole 104.

With continued reference to the embodiment illustrated in FIG. 4, the mounting pole 104 can be coupled to a carriage 130. The carriage 130 may be coupled to an adaptor 132. The carriage 130 and the adaptor 132 may form a slide assembly that allows the carriage 130 to slide linearly along the adaptor 132. The adaptor 132 can be coupled to the fixture (e.g., bed 102 and/or the rail 110). The carriage 130 may be directly coupled to the fixture (e.g., bed 102 and/or rail 110) without the adaptor 132. The carriage 130 and the adaptor 132 permit the movement of the mounting pole 104, the support arm 106, and the hyperdexterous surgical arm 200 in the generally horizontal direction. In some embodiments, the mounting pole 104 directly couples to the fixture (e.g., bed 102 and/or the rails 110) without the carriage 130 and/or the adaptor 132. The mounting pole 104 can be arranged such that the mounting pole 104 slides linearly along the fixture (e.g., bed 102 and/or the rails 110).

Referring to FIG. 4, the mounting pole 104 can be coupled to components that permit movement in other directions. For example, the mounting pole can be coupled to a slide (not shown) that moves orthogonal to the horizontal and vertical direction (e.g., extends outward from the fixture). The slide can be a drawer mounted to the fixture. For example, in embodiments where the fixture is the bed 102 the hyperdexterous surgical arm 200 can be moved laterally away from a side of the bed 102 (e.g., via a slidable drawer).

Figure 5:
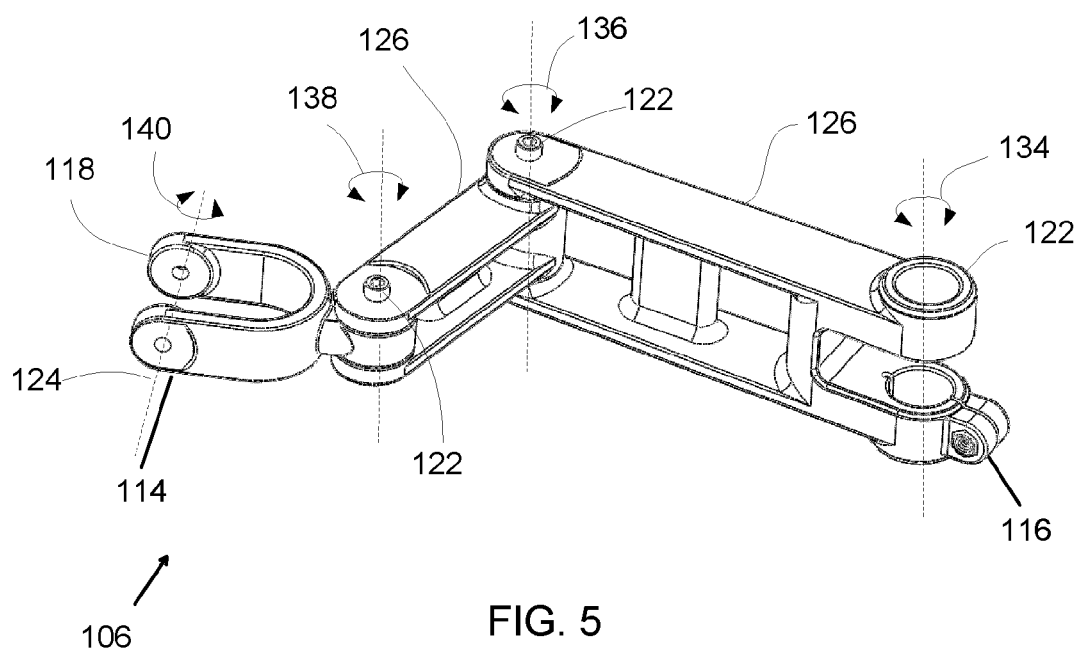
FIG. 5 schematically illustrates an embodiment of a support arm.

The hyperdexterous surgical system 100 can include mechanisms that couple or hold the hyperdexterous surgical arms 200 upright. FIGS. 2 and 4 shows the hyperdexterous surgical arm 200 optionally coupled to a support arm 106. The support arm 106 can be a passive arm, lacking motors or other electrical features. As shown in FIG. 5, the support arm 106 has a first end 114 and a second end 116. The first end 114 can include a bracket 118, such as a u-shaped bracket, that can be coupled to the hyperdexterous surgical arm 200. Other connections known in the art can also be utilized. The bracket 118 can couple to the hyperdexterous surgical arm 200 at the base of the hyperdexterous surgical arm 200, for example near a shoulder roll mechanism 202 (see FIG. 7), described further below. The second end 116 can be coupled to the elevator 120. The second end 116 can rotate about a center of rotation 122.

The support arm 106 may include one or more centers of rotation that allow the support arm 106 to rotate. The support arm 106 shown in FIG. 5 has three centers of rotation 122. The centers of rotation 122 rotate about an axis in the direction of the arrows, as shown in FIG. 5. The support arm 106 may include one or more tilt axes 124 which allow a portion of the support arm 106 to tilt. As shown in FIG. 5, the support arm 106 has one tilt axis 124 that allows a hyperdexterous surgical arm 200 coupled to the support arm 106 to tilt. The centers of rotation 122 and/or the tilt axis 124 allow the one or more links 126 of the support arm 106 and the bracket 118 to be rotated and positioned. The centers of rotation 122 may rotate the links 126 of the support arm 106 in the same plane, or in different planes, or in some combination of planes.

The support arm 106 can be passive. The operator 1 can move the support arm 106 by hand to position the support arm 106. The operator 1 can move the support arm 106 by hand to establish the Remote Center 250, described herein. In some embodiments, the support arm 106 can be active. In such an embodiment, the support arm 106 can include one or more motors to move joints of the support arm 106. The operator 1 can move the support arm 106 via the motors to establish the Remote Center 250.

The hyperdexterous surgical system 100 provides flexibility in positioning the hyperdexterous surgical arm 200 and/or the hyperdexterous surgical tool 300. The flexibility is advantageously enhanced by the centers of rotation 122 and/or tilt axes 124 of the support arm 106, shown in FIG. 5. The flexibility can be enhanced by the ability to move (e.g., vertically) the elevator 120 along the mounting pole 104. The flexibility can be enhanced by the ability to move (e.g., horizontally) the carriage 130 along the adaptor 132.

Figure 6:
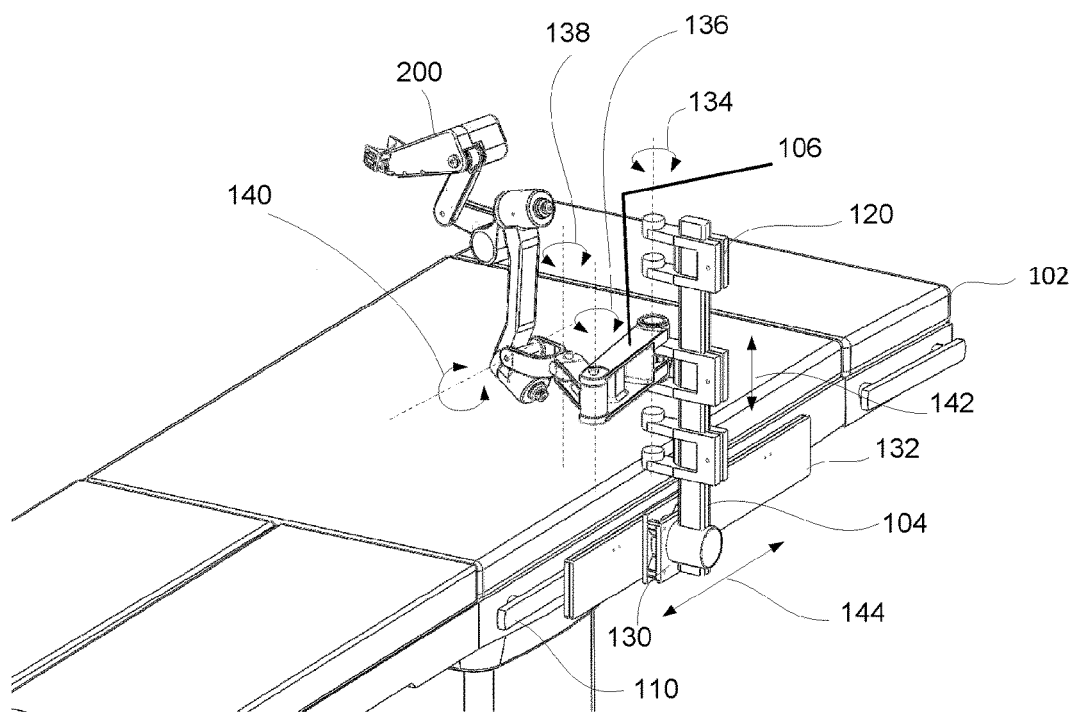
FIG. 6 schematically illustrates the multiple degrees of freedom of the hyperdexterous surgical arm of FIG. 4.

Referring now to FIG. 6, the support arm 106, the elevator 120, and the carriage 130 can facilitate the positioning of the hyperdexterous surgical arm 200. Arrow 134, Arrow 136, Arrow 138 and Arrow 140 demonstrate the centers of rotations and tilt axes of the support arm 106. Arrow 142 demonstrates the generally vertical direction the elevator 120 may be positioned along the mounting pole 104. Arrow 144 demonstrates the generally horizontal direction the carriage 130 may move along the adaptor 132 in relation to the fixture (e.g., bed 102 and/or rails 110). In one embodiment, the mounting pole 104 may be vertical, and the adaptor 132 may be horizontal; hence Arrow 142 may be vertical and Arrow 144 may be horizontal. All of the arrows or degrees of freedom can be configured differently than shown in FIG. 6 (e.g. the support arm 106 can have more or fewer centers of rotations or tilt axes).

The hyperdexterous surgical system 100 can enable the one or more hyperdexterous surgical arms 200 to be angled (e.g., tilt) to follow an orientation of a patient during the course of the surgery. Typically the patient is placed on a horizontal level surface (e.g., bed). In some surgeries, it may be advantageous to angle (e.g. tilt) the body of the patient relative to the horizontal surface (e.g., lowering the head of the patient to shift internal organs toward the head of the patient away from a surgical site for improved access to the surgical site) based on the surgery to be performed. The hyperdexterous surgical system 100 enables the angling (e.g., tilting from horizontal) of the hyperdexterous surgical arm 200 so that it follows the orientation of the patient 2 (e.g., the hyperdexterous surgical arm 200 is mounted to follow the orientation of the patient 2). The support arm 106, the elevator 120, the carriage 130 and the slide (not shown) can facilitate the tilting of the hyperdexterous surgical arm 200.

The position of the hyperdexterous surgical arm 200 in the work space may be tracked. In some embodiments, the position is tracked by coupling absolute encoders (not shown) at each joint of the hyperdexterous surgical arm 200. In some embodiments, a position sensor (such as an optical tracker) is mounted at the base of the hyperdexterous surgical arm 200. The position sensor can provide the position of the hyperdexterous surgical arm 200 relative to a ground reference point (not shown). The position sensor and/or the encoders can be utilized to track the position of the hyperdexterous surgical arm 200. Further, the position sensor and/or the encoders can be utilized to track the position of the hyperdexterous surgical tool 300. One skilled in the art may utilize others suitable sensors, mechanism or methods of tracking components of the hyperdexterous surgical system 100. The hyperdexterous surgical system 100 can have a global tracker that tracks the hyperdexterous surgical arm 200, hyperdexterous surgical tool 300, and additional components of the hyperdexterous surgical system 100 (e.g., the operator 1, the input devices 500).

The Hyperdexterous Surgical Arm

The hyperdexterous surgical arm 200 used with the hyperdexterous surgical system 100 can have a redundant degree of freedom. The redundant degree of freedom can advantageously allow the hyperdexterous surgical arm 200 to be placed in a variety of desired poses. Additionally, the redundant degree of freedom can advantageously enable more free space around the patient. The redundant degree of freedom can enable the use of more hyperdexterous surgical arms 200 (e.g., a plurality of hyperdexterous surgical arms 200). The redundant degree of freedom can enable the placement of more hyperdexterous surgical arms 200 within the free space above the patient 2. The redundant degree of freedom can also enable a larger workspace inside the patient. The redundant degree of freedom can reduce self-collisions (between components of a single hyperdexterous surgical arm 200) and other collisions (between hyperdexterous surgical arms 200, between hyperdexterous surgical arm 200 and the patient 2).

Redundancy is defined as follows: "When a manipulator can reach a specified position with more than one configuration of the linkages, the manipulator is said to be redundant." P. J. KcKerrow, Introduction to Robotics (Addison-Wesley Publishing Co, Sydney, 1991).

Figure 7:
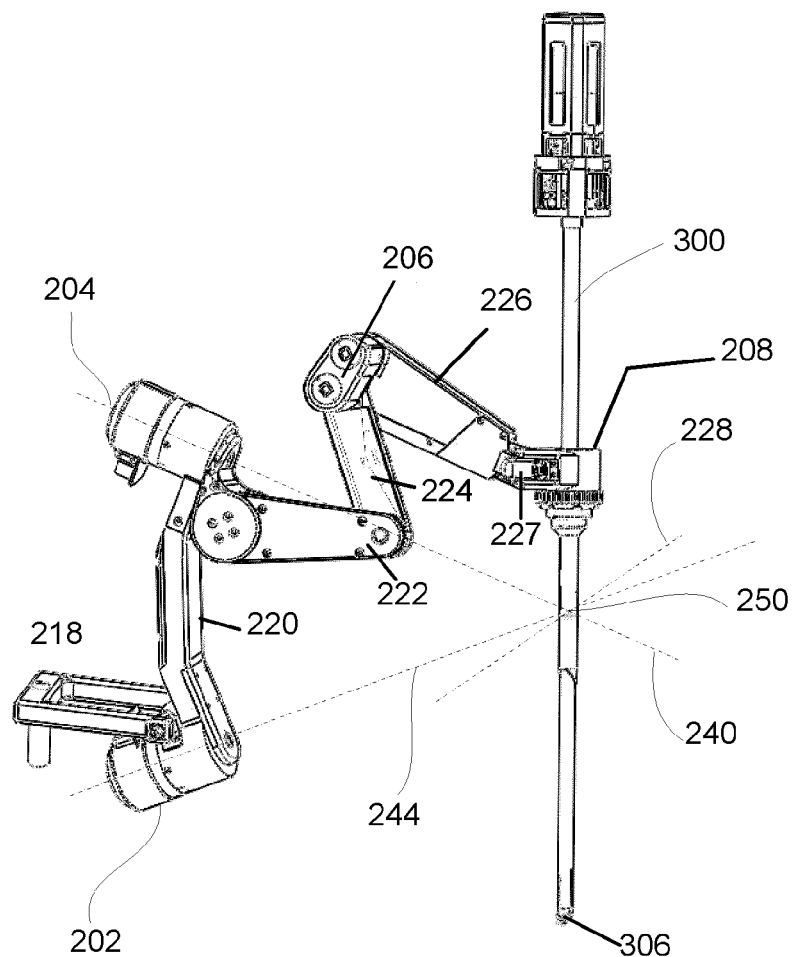
FIG. 7 schematically illustrates an embodiment of a hyperdexterous surgical arm with rotation axes and a Remote Center.

FIG. 7 shows one embodiment of a hyperdexterous surgical arm 200. The hyperdexterous surgical arm 200 can be used with the hyperdexterous surgical system 100 described herein. The hyperdexterous surgical arm 200 can have three degrees of freedom.

The redundant degree of freedom, in relation to on-market surgical systems, can be provided by the shoulder roll mechanism 202. The shoulder roll mechanism 202 can be located near a bottom of the hyperdexterous surgical arm 200. The redundant degree of freedom provides additional flexibility and advantages. An advantage provided by the redundant degree of freedom is that the hyperdexterous surgical arm 200 can access a larger work space and can access additional anatomical targets that on-market robotic arms with two degrees of freedom cannot reach. The redundant degree of freedom allows the hyperdexterous surgical arm 200 to maintain a tip position of the hyperdexterous surgical tool 300 and Remote Center 250 while reconfiguring the components of the hyperdexterous surgical arm 200 external to the body. These different poses enable the hyperdexterous surgical arm 200 to avoid collisions with the patient 2, other tools or other objects in the surgical arena.

In some embodiments, the redundant degree of freedom, in relation to on-market surgical systems, is provided by a redundant pitch mechanism (not shown). The redundant pitch mechanism can be located anywhere on the hyperdexterous surgical arm 200. The redundant pitch mechanism can be located near a bottom of the hyperdexterous surgical arm 200. The redundant pitch mechanism can have a pitch axis that intersects the Remote Center, as described herein. The redundant degree of freedom provided by a redundant pitch mechanism can have the same advantages of the redundant degree of freedom provided by the redundant roll mechanism 202 described herein. The hyperdexterous surgical tool 300 and the rotate/translate mechanism 208 can have four degrees of freedom (e.g., rotate, translate, pitch, yaw). The rotate/translate mechanism 208 can rotate and translate the tool 300. The hyperdexterous surgical tool 300 can pitch and roll. Therefore, the hyperdexterous surgical arm 200 and the hyperdexterous surgical tool 300 can have seven degrees of freedom in total. The hyperdexterous surgical arm 200 and the hyperdexterous surgical tool 300 can have more than seven degrees of freedom (e.g., eight degrees of freedom, nine degrees of freedom, etc.). The hyperdexterous surgical arm 200 and the hyperdexterous surgical tool can have additional degrees of freedom (e.g., provided by end effectors, such as graspers, flexible elbows). Typically, on-market surgical robotic systems have a robotic arm with two degrees of freedom (pitch and roll) and the tool has four degrees of freedom (rotate, translate, pitch, yaw), such that on-market robotic surgical systems typically have a total of six degrees of freedom.

With continued reference to FIG. 7, the shoulder roll mechanism 202 provides one degree of freedom. The main roll mechanism 204 provides one degree of freedom. The pitch mechanism 206 provides one degree of freedom. The rotate/translate mechanism 208 and hyperdexterous surgical tool 300 provide four degrees of freedom (rotate, translate, pitch, yaw). There are four mechanisms which contribute to the dexterity of the hyperdexterous surgical arm: (1) the shoulder roll mechanism 202; (2) the main roll mechanism 204; (3) the pitch mechanism 206; and (4) the rotate translate mechanism 208. Incorporating a second roll mechanism, the shoulder roll mechanism 202, provides a redundant degree of freedom (e.g. a seventh degree of freedom) as compared to on-market surgical system.

The shoulder roll mechanism 202 has shoulder roll axis 244. The main roll mechanism 204 has main roll axis 240. The pitch mechanism 206 has pitch axis 228. The axes 228, 240, 244 of the mechanisms 202, 204, 206 intersect at a common point. In FIG. 7, this point is labeled the Remote Center 250.

Figure 8:
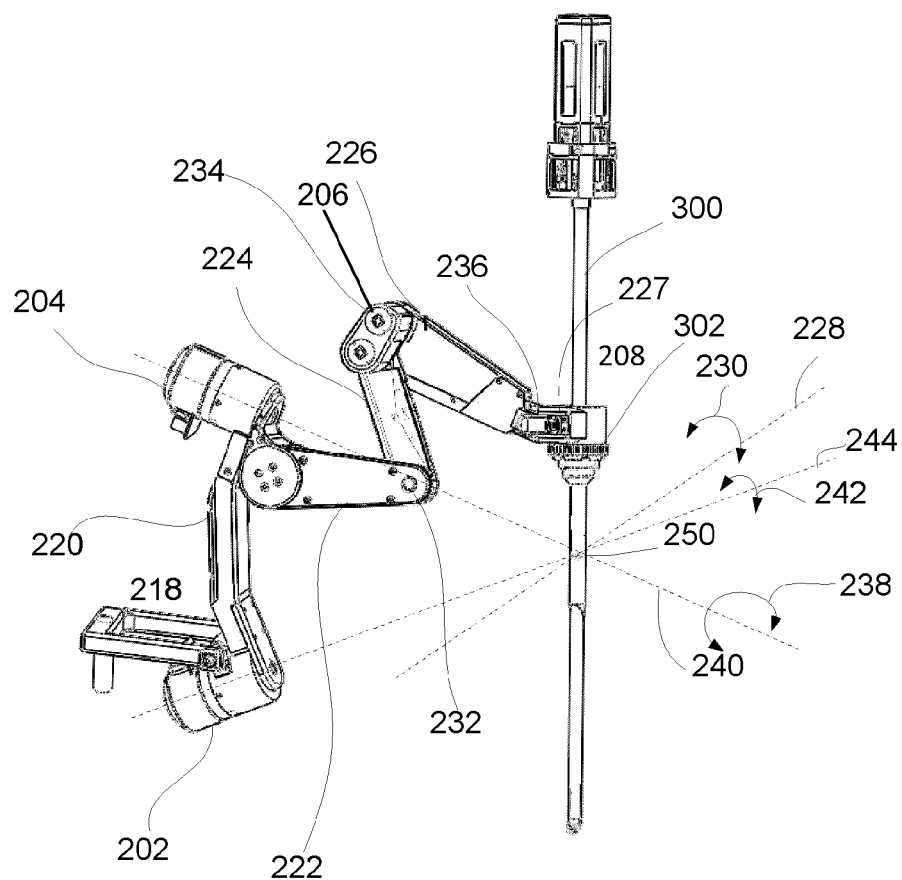
FIG. 8 schematically illustrates the degree of freedoms of an embodiment of the hyperdexterous surgical arm of FIG. 7.

Referring to FIG. 8, the pitch mechanism 206 allows the hyperdexterous surgical arm 200 to rotate the hyperdexterous surgical tool 300 about the pitch axis 228. The pitch axis 228 passes through the Remote Center 250. Arrow 230 illustrates the arc representing the path of the hyperdexterous surgical tool 300 about the pitch axis 228. The pitch mechanism 206 has three centers of rotation, 232, 234, and 236. The centers of rotation 232, 234, and 236 are mechanically linked so as to create motion about the pitch axis 228.

Referring still to FIG. 8, the pitch mechanism 206 has three segments, the pitch segment 224, the pitch segment 226, and the pitch segment 227. The pitch segments 224, 226, and 227 of the pitch mechanism 206 can have many configurations, such as a 2-bar, 3-bar, or 4-bar linkage, or cable linkages. In some embodiments, bands or belts constrain the relative angles between the pitch segments 224, 226, and 227. The pitch segment 224 and the pitch segment 226 may collapse on top of each other or have a small angle between each other while rotating the hyperdexterous surgical tool 300 around the pitch axis 228. When the pitch segments are close to the collapsed position, the main roll mechanism 204 and proximal end of the trocar 302 can be brought close together. Alternatively, the pitch segment 224 and pitch segment 226 can also extend out, or have a large angle between each other so that the distance between the main roll mechanism 204 and the proximal end of the trocar 302 are spaced further apart.

The rotations and motions of the roll mechanisms 202, 204 are shown in FIG. 8. The arrow 238 shows the rotation of the main roll mechanism 204 about main roll axis 240. The arrow 242 shows the rotation of the shoulder roll mechanism 202 about the shoulder roll axis 244. In some embodiments, the shoulder roll mechanism 202 can rotate at least up to +/−90° from an initial position. In other embodiments, the shoulder roll mechanism 202 can rotate more than +/−90° from an initial position. The main roll axis 240 and the shoulder roll axis 244 intersect at the Remote Center 250 as shown in FIG. 8. The main roll segment 222 of the main roll mechanism 204 and/or shoulder roll segment 220 of the shoulder roll mechanism 202 can have any size, shape and/or number of segments. As shown, a shoulder roll segment 220 couples the shoulder roll mechanism 202 to the main roll mechanism 204 and a main roll segment 222 couples the main roll mechanism 204 to the pitch segment 224.

One embodiment of the arrangement of the various segments of the hyperdexterous surgical arm 200 is shown in FIG. 7. One end of the first segment 218 can optionally be coupled to a fixture (e.g., the bed 102), the support arm 106 or other support objects within the operating arena, as discussed above. The other end of the first segment 218 is coupled with the shoulder roll mechanism 202. The shoulder roll mechanism 202 is connected to the main roll mechanism 204 with one or more segments 220. One or more segments 222, 224 connect the main roll mechanism 204 with the pitch mechanism 206. One or more segments 226, 227 can connect the pitch mechanism 206 with the trocar 302.

In typical minimally invasive surgery, a small incision is made on the patient's body through which the tools are passed into the body. For example, in abdominal surgery an incision is placed on the abdominal wall. To reduce the risk of harm to the patient, it is desirable to minimize movements that involve translation along the surface of the body at the point of entry into the body as these types of movements may cause tearing of the tissues at the point of entry. Thus in minimally invasive procedures, it is desirable for the tool shaft to always pass through a constant point. The Remote Center may be located at the point of entry of the tools into the body. The hyperdexterous surgical tools 300 can be pivoted about this point by the hyperdexterous surgical arm 200 without tearing the tissue at the point of entry. The mounting of the hyperdexterous surgical arm 200 relative to the patient 2 can establish the Remote Center 250 at the incision.

The arrangement of the axes allows the mechanisms 202, 204, 208 to achieve the desired position of the hyperdexterous surgical tool 300 while the location of the Remote Center 250 is held constant. The Remote Center 250 may correspond with the location of an incision on a patient or the location of the entry point of a hyperdexterous surgical tool 300 into the body as noted above. The Remote Center 250 can advantageously be held constant in order to reduce the risk of harm or injury to a patient. During surgery, for example during abdominal surgery, the Remote Center 250 may be placed at the abdominal wall. This location can be a gateway for tools to enter the abdominal cavity. As different positions and orientations of a hyperdexterous surgical tool 300 are desired, the shoulder roll mechanism 202, the main roll mechanism 204, and the pitch mechanism 206 may be activated in such a manner that the hyperdexterous surgical tool 300 pivots in the allowable degrees of freedom about the Remote Center 250.

The location of the Remote Center 250 may be constrained by the anatomy of the patient. The flexibility of the hyperdexterous surgical system 100 advantageously allows the efficient placement of the one or more hyperdexterous surgical arms 200 and/or the hyperdexterous surgical tool 300 in relation to the patient, the one or more operators 1 such as surgeons, the one or more assistants, and/or other objects or components found within the operating arena.

Figure 9:
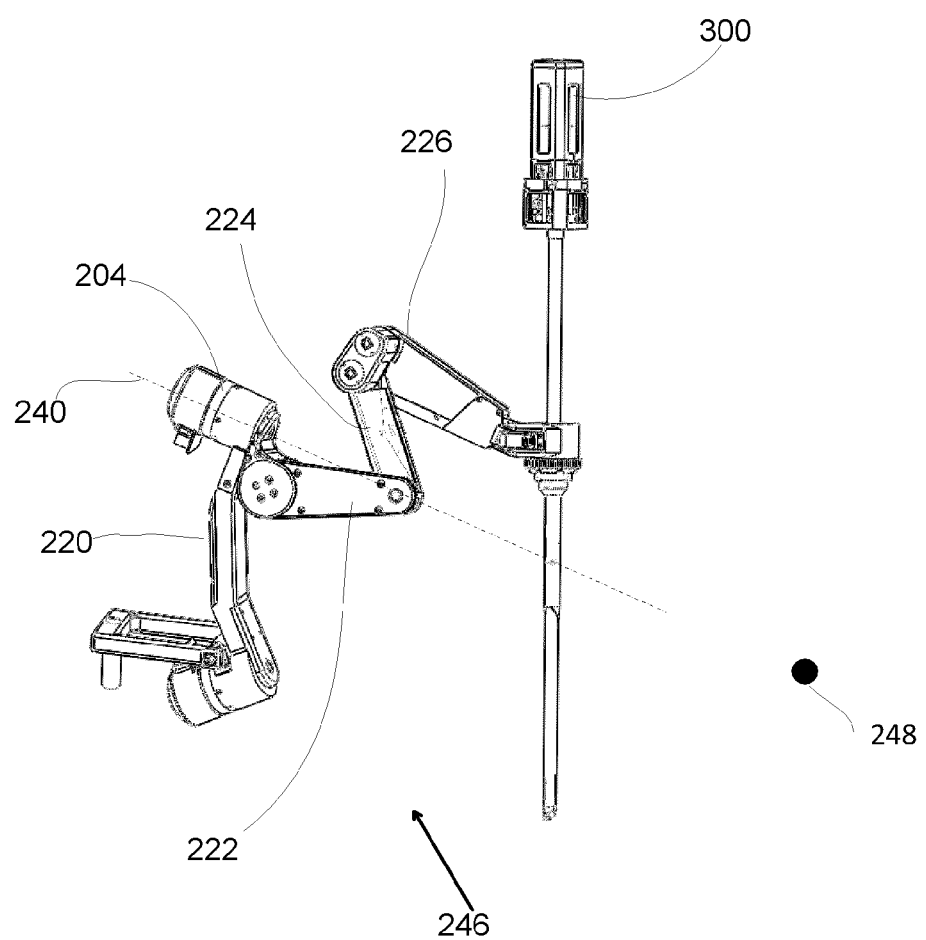
FIG. 9 schematically illustrates a zero position, an initial position of a hyperdexterous surgical tool, and a target position.
Figure 10:
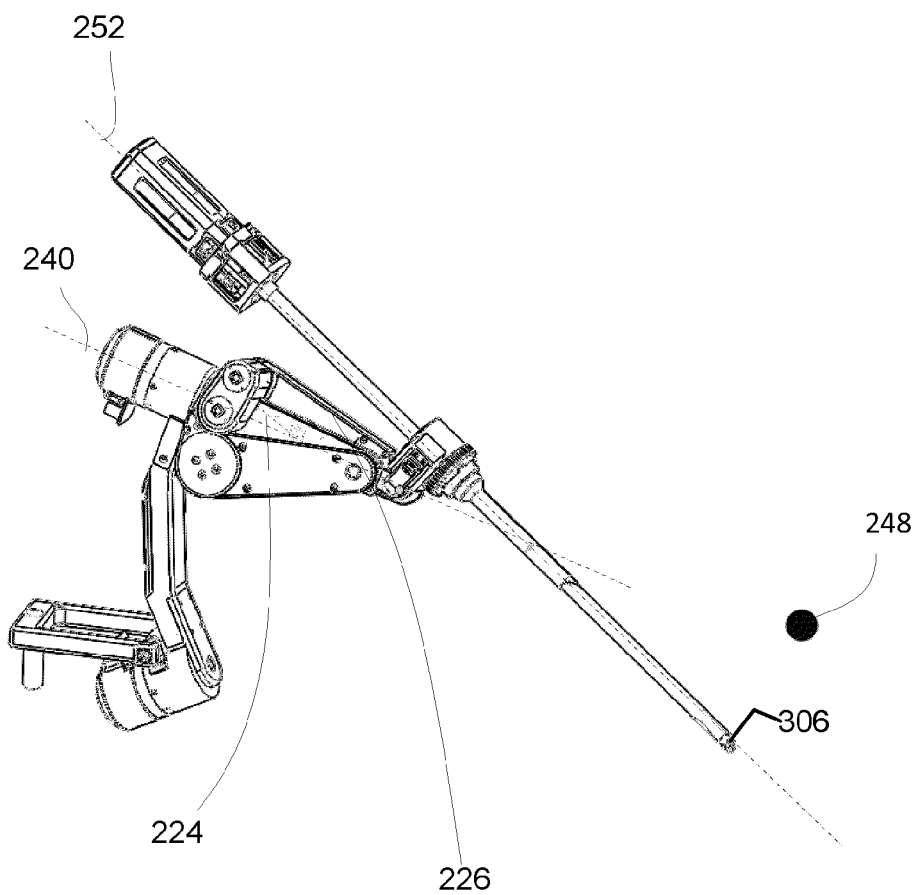
FIG. 10 schematically illustrates the inability of a hyperdexterous surgical tool to reach the target position due to the interference between the pitch segment and the other portions of the hyperdexterous surgical arm.

FIG. 9 illustrates a hyperdexterous surgical arm 200 in an initial position, referred to herein a zero position 246. An example of a targeted position, the target tool tip position 248, is shown. In this example, the target tool tip position 248 is directly in front of the main roll mechanism 204 and is collinear with the main roll axis 240. One way to try to reach the target tip position 248 is to collapse pitch segment 224 and pitch segment 226 as shown in FIG. 10. However even after collapsing the pitch segments 224, 226, the hyperdexterous surgical tool 300 is unable to reach the target tool tip position 248 (see FIG. 10). This may occur, for example, because the end of the range of the pitch motion is encountered.

Figure 11:
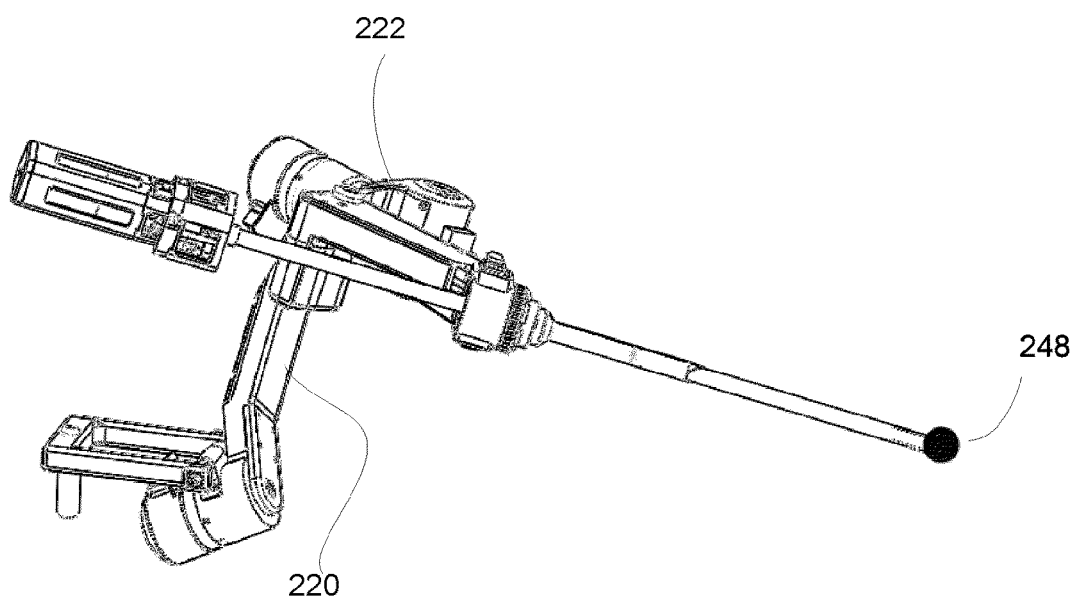
FIG. 11 schematically illustrates how the shoulder roll segment may be activated to reach the same target point of FIG. 10.

The shoulder roll mechanism 202 provides the redundant degree of freedom enabling the hyperdexterous surgical arm 200 to reach the target tool tip position 248, as shown in FIG. 11. The shoulder roll mechanism 202 is a redundant roll mechanism. The shoulder roll mechanism 202 provides the redundant degree of freedom as compared with on-market robotic systems. Viewing the hyperdexterous surgical arm 200 from the target tool tip position 248, the shoulder roll segment 220 is partly rotated clockwise and the main roll segment 222 is partly rotated counterclockwise, from the zero position 246, shown in FIG. 9. By rotating the shoulder roll mechanism 202 and the main roll mechanism 204, the target tool tip position 248 is now accessible. Thus it may be seen that a second roll mechanism, such as the shoulder roll mechanism 202 shown in FIGS. 9-11, with an axis of rotation that intersects the axis of rotation of another roll mechanism increases the dexterity of the hyperdexterous surgical arm 200. The shoulder roll mechanism 202 has an axis of rotation 244 that intersects the axis of rotation 240 of the main roll mechanism 204, as shown in FIG. 8, therefore increasing the maneuverability and/or dexterity of the hyperdexterous surgical arm 200.

Singularities, Dead Zones, Free Space, Backlash

The design of the hyperdexterous surgical arm 200 provides significant attributes to the hyperdexterous surgical system 100. The location of the Rotation Center 250 relative to the hyperdexterous surgical arm 200 permits dead zones to be placed away from the patient. The small size of the hyperdexterous surgical arm 200 enables the maximizing of free space around the patient, which facilitates the simultaneous use of manual tools and/or hyperdexterous surgical tools. The redundant degree of freedom provided by the shoulder roll mechanism 202 can increase the performance of the system in such areas as lowering the effect of backlash and improving the practical bandwidth of the hyperdexterous surgical arm 200.

The hyperdexterous surgical arm 200 may advantageously avoid singularities during operation. A singularity is defined as the collinear alignment of two or more axes. This condition may result in unpredictable motion and velocities of the hyperdexterous surgical arm 200. When two axes align, rotation about either axis is not unique. In other words, motion along one degree of freedom is lost.

Referring back to FIG. 10, the pitch segment 224 and the pitch segment 226 are collapsed relative to each other. In such positions, the tool shaft axis 252 and the main roll axis 240 subtend an acute angle. If the tool shaft axis 252 and the main roll axis 240 were aligned, then the rotation about the main roll axis 240 would be identical to the rotation about the tool shaft axis 252. In such positions, movement about either axis imparts the same motion to the hyperdexterous surgical tool 300. In such positions, control of the end effector 306 is not optimal because one degree of freedom is lost. FIG. 11 shows that the shoulder roll mechanism 202 can rotate the hyperdexterous surgical arm 200 such that the tool shaft axis 252 and the main roll axis 240 are not aligned. The additional degree of freedom offered by the shoulder roll mechanism 202 prevents the hyperdexterous surgical system 100 from losing one degree of freedom when axes align, substantially align, or are in near alignment. In this way, the hyperdexterous surgical arm 200 may be designed to avoid singularities during the operation of the hyperdexterous surgical arm 200.

Figure 12:
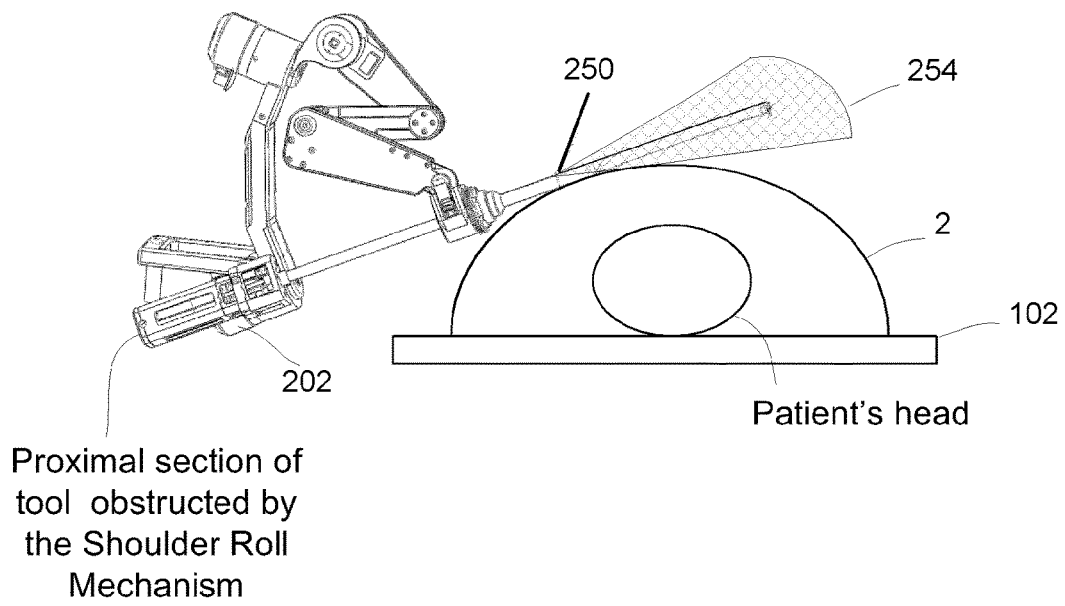
FIG. 12 schematically illustrates the location of a dead zone for a hyperdexterous surgical arm.

The hyperdexterous surgical arm 200 may advantageously minimize a dead zone. A dead zone is defined as one or more regions inaccessible by the hyperdexterous surgical tool 300. The dead zone 254 can be created by interference between components of the hyperdexterous surgical arm 200. For example, as shown in FIG. 12, the dead zone 254 can be created because of interference between the proximal end of the hyperdexterous surgical tool 300 and the shoulder roll mechanism 202. The dead zone 254 shown in FIG. 12 may be eliminated by making the pitch segments 224, 226 and/or 227 with a different size, shape or number of segments (e.g., longer to fit around the proximal end of the hyperdexterous surgical tool 300). However, this may increase the size and/or weight of the hyperdexterous surgical arm 200. The dead zone 254 shown in FIG. 12 may be eliminated by making the proximal end of hyperdexterous surgical tool 300 a different size or shape (e.g., shorter to fit inside the shoulder roll mechanism 202).

The hyperdexterous surgical arm 200 may be designed so that one or more dead zones 254 occur outside the body of the patient 2, such that the dead zone does not limit the functionality of the hyperdexterous surgical arm 200. The hyperdexterous surgical arm 200 is therefore able to position the hyperdexterous surgical tool 300 anywhere within the workspace, inside the patient's body.

Referring to FIG. 12, the main roll mechanism 204 is rotated such that the hyperdexterous surgical tool 300 now faces upwards. The shoulder roll mechanism 202 interferes or otherwise limits the movement of the proximal end of the hyperdexterous surgical tool 300 such as to create a dead zone 254. The cross hatched area illustrating the dead zone 254 shows positions the distal tip of the hyperdexterous surgical tool 300 cannot achieve due to the obstruction of the proximal end of the hyperdexterous surgical tool 300 with the shoulder roll mechanism 202. FIG. 12 shows the body of the patient 2. As shown, the dead zone 254 is placed outside and upwards away from the body of the patient 2. The inability of the distal tip of the hyperdexterous surgical tool 300 to reach points within the dead zone 254 shown in FIG. 12 will not impact the use of the hyperdexterous surgical tool 300 in surgical procedures. The dead zone 254 shown in FIG. 12 includes positions where surgery is not performed.

As discussed above, the hyperdexterous surgical arm 200 can be mounted (e.g., via support arm 106, mounting poles 104, etc.) so that the dead zone occurs outside of the body. In some embodiments, the shoulder roll mechanism 202 may be located below the Remote Center 250 as shown in FIG. 7. In some embodiments, the shoulder roll mechanism 202 is closer to the fixture (e.g., hospital bed) to which the hyperdexterous surgical arm 200 is mounted as shown in FIG. 12. By orienting the shoulder roll mechanism 202 as low as possible relative to the Remote Center 250, the dead zones 254 are advantageously placed up and away from the body of the patient 2. Referring back to FIG. 6, the shoulder roll mechanism 202 is closer to the bed 102 or horizontal surface upon which the patient 2 is placed. The ability to position the hyperdexterous surgical arm 200 by positioning the support arm 106, the mounting pole 104, the elevator 120, the carriage 130 and/or the adaptor 132 advantageously provides additional flexibility in the placement of the dead zone 254. In some embodiments, the shoulder roll mechanism 202 may be located above the Remote Center 250 (e.g., due to mounting, positioning of patient on their side).

In some embodiments, the hyperdexterous surgical arm 200 is small in size. The hyperdexterous surgical arm 200 can in some embodiments weigh less than 10 pounds, less than 8 pounds, less than 6 pounds, less than 4 pounds, less than 3 pounds. The hyperdexterous surgical arm 200 can be less than 24 inches long, less than less than 22 inches long, less than 20 inches long, less than 16 inches long, less than 14 inches long, less than 12 inches long. In one embodiment, the hyperdexterous surgical arm 200 can be compact when in a collapsed configuration.

The small size of the hyperdexterous surgical arm 200 enables more free space around the patient 2. The free space enables the surgeon to manipulate a manual tool 350 from various positions. The free space enables the surgeon to reposition himself at multiple locations during surgery. The free space enables the operator to use manual tools 350 concurrently with use of the hyperdexterous surgical arm 200. The free space permits easier physical access to the patient when necessary.

Figure 13A:
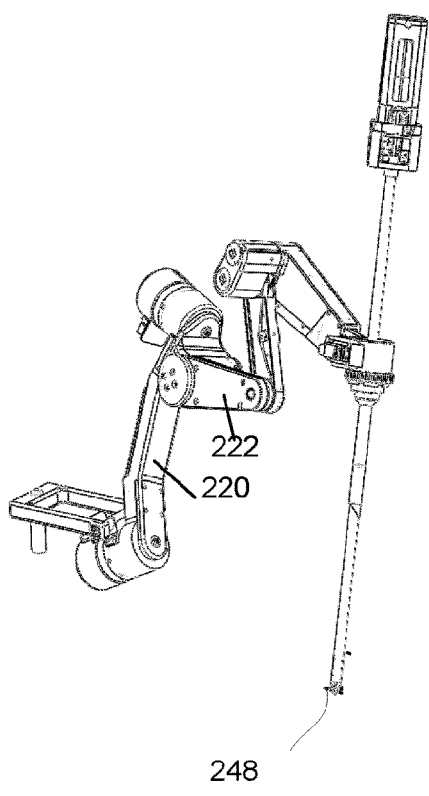
FIG. 13A schematically illustrates an arrangement of a hyperdexterous surgical arm to reach a target position.
Figure 13B:
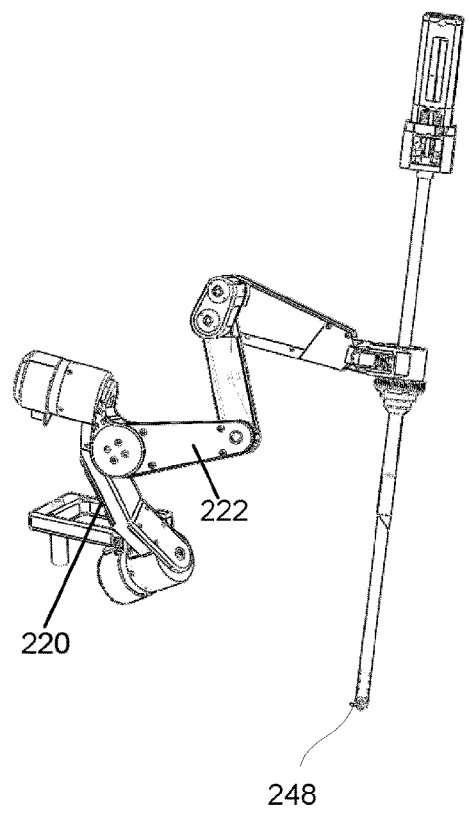
FIG. 13B schematically illustrates another arrangement of a hyperdexterous surgical arm to reach the target position of FIG. 13A.

Advantageously, the operator 1 is able to access the patient to use a manual tool 350 while simultaneously using the hyperdexterous surgical arm 200 to control the hyperdexterous surgical tool 300. The operator 1 may prefer to have free space to manipulate the required tools or to move to a more optimal position with respect to the patient 2. The hyperdexterous surgical arm 200 can be moved to a different position while maintaining the Remote Center 250. The different position may allow greater access to the patient. The shoulder roll mechanism 202 provides the ability to move the hyperdexterous surgical arm 200 to different positions while maintaining the Remote Center FIG. 13A shows an initial position of hyperdexterous surgical arm 200. The figure shows the target tool tip position 248 of the hyperdexterous surgical tool 300. In FIG. 13B, the location and orientation of the hyperdexterous surgical tool 300 remains the same. The hyperdexterous surgical arm 200 has assumed a different position. Viewing the hyperdexterous surgical arm 200 from the target tool tip position 248, the shoulder roll segment 220 is partly rotated counterclockwise and the main roll segment 222 is partly rotated clockwise from the position shown in FIG. 13A. Thus along with the rotate/translate mechanism 206 which imparts translation and rotation along the toll shaft axis 252, the hyperdexterous surgical tool 300 may be able to maintained at the same target tool tip position 248 with various poses of the hyperdexterous surgical arm 200. The operator 1 can place the hyperdexterous surgical arm 200 in an optimal position for a procedure, as needed.

The shoulder roll mechanism 202 provides the ability to move the hyperdexterous surgical arm 200 to different positions to avoid other restrictions. Restrictions may be imposed in a surgical environment by a variety of factors. These factors include the body habitus of the patient 2, limitations of objects in the operating arena based on physical dimensions and movability, and the presence of other instruments near or in the work space. The shoulder roll mechanism 202 may help to work around these restrictions. The hyperdexterous surgical arm 200 may be positioned to minimize or eliminate the effects of the restrictions.

The redundant degree of freedom provided by the shoulder roll mechanism 202 (as compared with on-market systems) will increase the performance of the hyperdexterous surgical system 100 in such areas as lowering the effect of backlash and improving or increasing the practical bandwidth of the system. Bandwidth is the ability of a hyperdexterous surgical tool 300 to faithfully follow the motion of an input device 500. Higher bandwidths may allow the hyperdexterous surgical tool 300 to accelerate faster. For instance, in a low bandwidth system, if an operator 1 moves the input device 500 quickly or at a rapid speed, the hyperdexterous surgical tool 300 may not be able to follow the motion of the input device 500. Backlash is the amount of "play" in a mechanical system.

In systems that have a fixed Remote Center 250, bandwidth and backlash are generally inversely related. For example, if the end effector 306 of the hyperdexterous surgical tool 300 is very close to the Remote Center 250, the main roll mechanism 204 and/or the shoulder roll mechanism 202 moves a large amount to cause a small movement of the end effector 306. This movement stresses the bandwidth limitations of the hyperdexterous surgical arm 200, but is favorable from an actuator backlash perspective. As another example, if the shaft of the hyperdexterous surgical tool 300 is extended far into the body of the patient 2 and away from any singularities, more demand is placed on the main roll mechanism 204 and/or the shoulder roll mechanism 202 to effect a change of the end effector 306. The bandwidth is appropriate but the backlash may become significant. The parameters such as bandwidth and backlash may vary considerably from region to region within the work space.

Sweet spots are regions where the hyperdexterous surgical system 100 is controlled and parameters such as bandwidth and backlash are within acceptable parameters. Factors including bandwidth, backlash, mechanical limitations imposed by the design of the system, location of singularities (where two or more degrees of freedom coincide) may impact the sweet spot of the system. Designers attempt to have the sweet spot define a region as large as possible for the task to be performed.

In some embodiments, the bandwidth and backlash are optimized for all regions within the work space. The bandwidth and backlash are not optimal around singularities. For example, a singularity may exist when the tool shaft axis 252 aligns with the main roll axis 240, as shown in FIG. 10. The end effector 306 may be more difficult to control. The shoulder roll mechanism 202 may prevent singularities by providing an additional degree of freedom. The shoulder roll mechanism 202 may provide additional poses of the hyperdexterous surgical arm 200 and provide additional ways to arrange segments of the hyperdexterous surgical arm 200. The shoulder roll mechanism 202 can provide a greater working area over which the bandwidth and backlash are within acceptable parameters.

Alternative Arms

Figure 14:
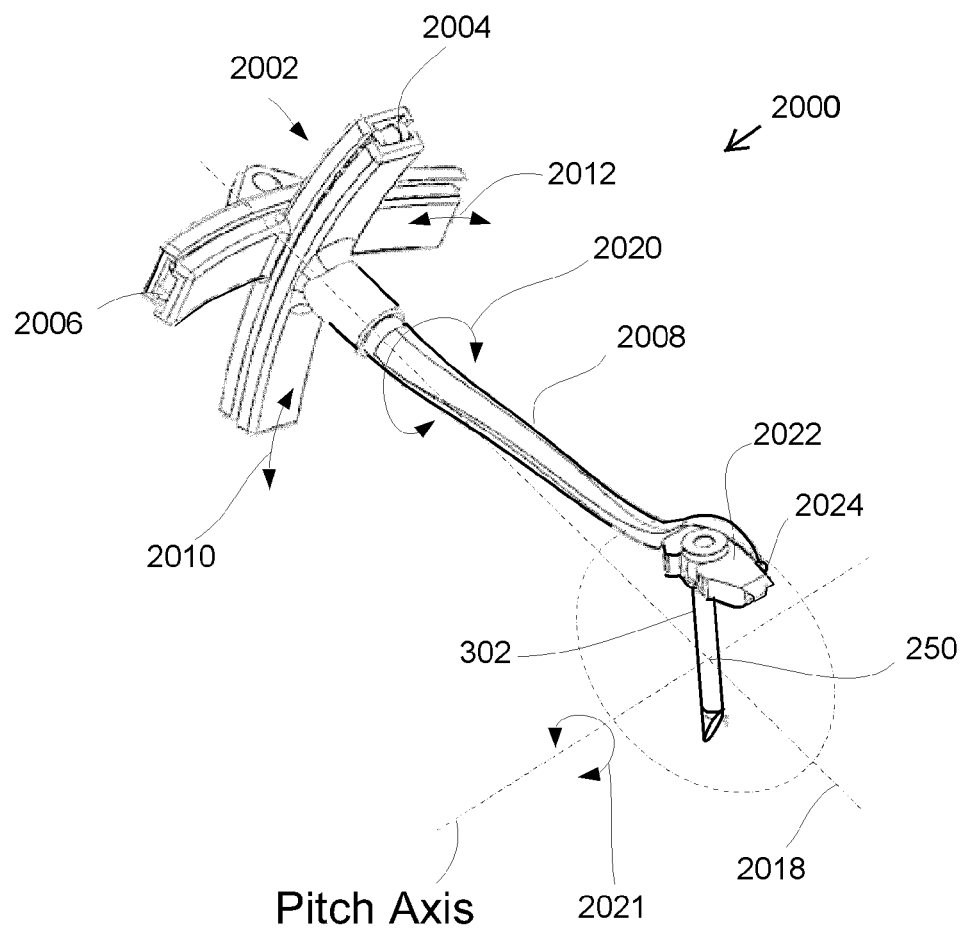
FIG. 14 schematically illustrates an embodiment of a hyperdexterous surgical arm.
Figure 15:
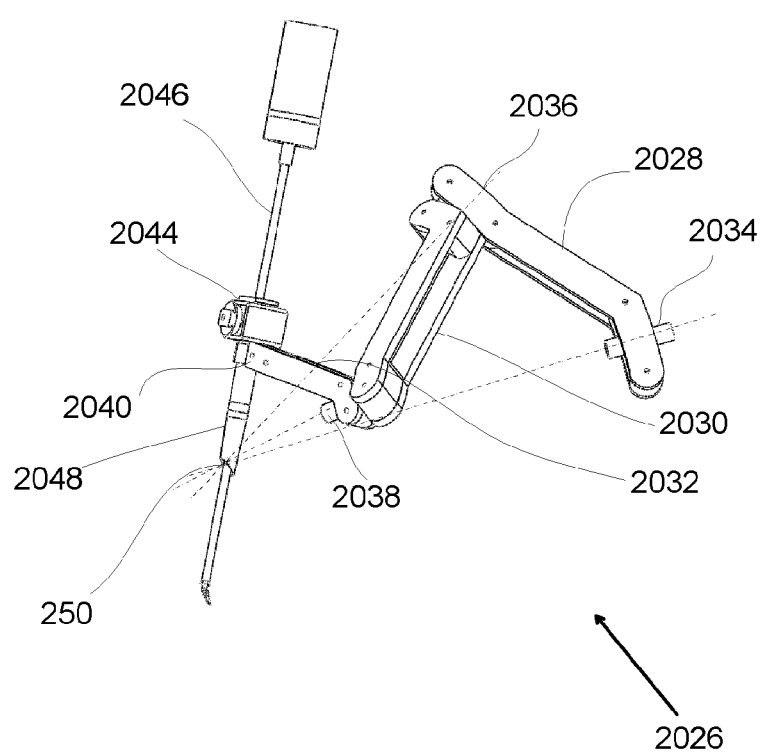
FIG. 15 schematically illustrates an embodiment of a hyperdexterous surgical arm.
Figure 16:
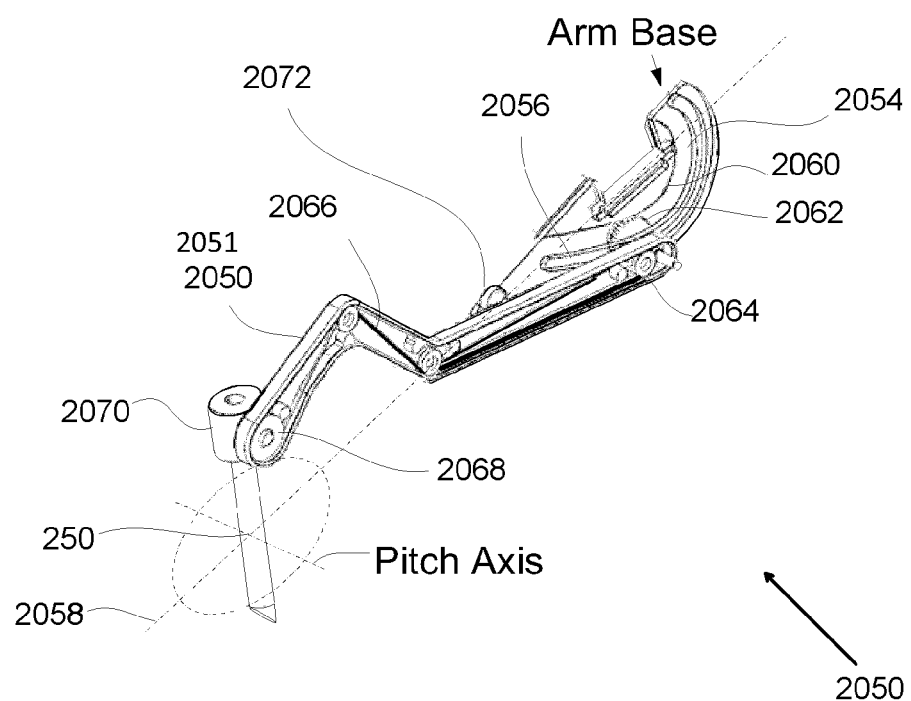
FIG. 16 schematically illustrates an embodiment of a hyperdexterous surgical arm.

The hyperdexterous surgical arm can have many configurations. FIGS. 14-16 show alternative configurations of the hyperdexterous surgical arm. The hyperdexterous surgical arm can preserve a Remote Center 250, as described herein. The hyperdexterous surgical arm can be incorporated into the hyperdexterous surgical systems described herein. The hyperdexterous surgical arm can be controlled by input devices 500 which enable the operator to be mobile.

FIG. 14 shows an embodiment of a hyperdexterous surgical arm 2000. The hyperdexterous surgical arm 2000 can include a base 2002 including a first roller slide 2004 and a second roller slide 2006. The first roller slide 2004 can be orthogonal to the second roller slide 2006. The first roller slide 2004 permits movement in a first direction (e.g. vertical). The second roller slide 2006 permits movement in a second direction (e.g. horizontal). The rolling slide 2004 can position an offset arm 2008 along the direction of Arrow 2010 and/or rolling slide 2006 can position the offset arm along the direction of Arrow 2012. The first roller slide 2004 and/or the second roller slide can be passive (e.g., not motorized). The first roller slide 2004 and/or the second roller slide can be active (e.g., motorized).

The hyperdexterous surgical arm 2000 includes an offset arm 2008. The offset arm 2008 is offset (e.g., the structure of the offset arm 2008 is not concentric or symmetric about its longitudinal axis). The offset arm 2008 includes two degrees of freedom (pitch and roll). The offset arm 2008 can include a pitch mechanism 2024 and a roll mechanism. The pitch mechanism 2024 has a pitch axis. The offset arm 2008 can rotate a trocar 302 about the pitch axis, about Arrow 2021. The roll mechanism has a roll axis 2018. The offset arm 2008 can rotate around the roll axis 2018 in the direction of Arrow 2020. The pitch axis and the roll axis intersect the Remote Center 250. The rolling slide 2004 and the rolling slide 2006 also allow motion only about axes which pass through the Remote Center.

The distal end of the offset arm 2008 may be coupled to a trocar carrier 2022. In some embodiments, the offset arm 2008 is coupled to the trocar carrier 2022 by an arcing slide. An arcing slide having a circular radius will maintain a fixed center of rotation, such as the Remote Center 250. The shape of the arc can be altered. In some embodiments, the shape of the arc is elliptical. By alternating the shape, the location of Rotation Center could be made to vary in the vertical direction. In one embodiment, the pitch mechanism 2024 is provided at least in part by the rolling slide 2004 coupled to the trocar carrier 2022.

The rolling slide 2024 may extend up to +/−90° from vertical (including +/−15°, +/−30°, +/−45°, +/−60°, +/−75°, etc.) by rolling between the distal end of the hyperdexterous surgical arm 2000 and the trocar carrier 2022 in a curved, telescoping fashion. When the rolling slide 2024 is vertical, the rolling slide 2024 may be within the profile of the trocar carrier 2022. This may minimize the swept volume, thereby reducing interference with surrounding tissue, other equipment, and/or operating room personnel.

The pitch mechanism 2024, the roll mechanism, first roller slide 2004, and the second roller slide 2006 can be passive or active. In some embodiments, the motion of the hyperdexterous surgical arm 2000 may be actively controlled and may be manipulated by an energy source (e.g., motors such as electric motors, hydraulics, pneumatics, etc. not shown).

The offset arm 2008 has two degrees of freedom (pitch and roll). The rolling slide 2004 and the rolling slide 2006 can provide two degrees of freedom by providing movement along Arrow 2010 and Arrow 2012. The hyperdexterous surgical arm 2000 can have four degrees of freedom.

FIG. 15 shows an embodiment of a hyperdexterous surgical arm 2026. The hyperdexterous surgical arm 2026 may include three segments, segment 2028, segment 2030, and segment 2032. The segments 2028, 2030, and 2032 are coupled to each other by roll mechanism. In other embodiments, the segments 2028, 2030, 2032 are coupled to each other via other suitable mechanisms. The three mechanisms have axes of rotation 2034, 2036, 2038. These axes intersect at the Remote Center 250. The third roll mechanism in the hyperdexterous surgical arm 2026 provides a redundant degree of freedom.

The distal end of the hyperdexterous surgical arm 2026 may be coupled to a hyperdexterous surgical tool 2046 and/or a trocar 2048. The hyperdexterous surgical arm 2026 may include a rotate/translate mechanism 2044 which translates and rotates the tool 2046. The tool 2046 may have two degrees of freedom (pitch, yaw). The combination of the hyperdexterous surgical arm 2026, the rotate/translate mechanism 2044, and the hyperdexterous surgical tool 2046 can have seven degrees of freedom. The tool 2046 can have additional degrees of freedom.

FIG. 16 shows an embodiment of an alternative pitch mechanism. The arm 2050 of FIG. 16 can be combined with additional mechanism (e.g., roll mechanisms, pitch mechanisms) in order to provide a hyperdexterous surgical arm. The arm 2050 can preserve a Remote Center 250. The arm 2050 can include a roll mechanism that rotates about the roll axis 2058. The follower plate 2054 can rotate about the roll axis 2058 and can be supported by a bearing (not shown). The arm 2050 can be mounted to other mechanisms in such a way that the arm 2050 would rotate about roll axis 2058, supported by the bearing (not shown) and actuated by a motor (not shown).

The arm 2050 can provide a pitch mechanism that rotates about the pitch axis. The pitch mechanism can take a number of forms include four bar linkages, band- or cable-constrained parallel mechanisms, or gear and cam. A gear and cam mechanisms is shown in FIG. 16.

The follower plate 2054 can include a profiled slot 2056. The follower plate 2054 can include a gear profile 2060 which can engage a gear follower 2062. The gear profile 2060 may be non-circular, and/or the gear follower can be non-circular. The gear follower 2062 can drive a cable spool 2064 which can drive a cable 2066. The cable 2066 can be coupled to the arm 2051. The arm 2051 may include gears or pulleys that interact with the cable 2066. The cable 2066 drives the rotation of the output pulley 2068. The output pulley 2068 may be near the distal end of the arm 2051 and may be coupled to the trocar 2070. The arm 2051 may slide through a linear bearing 2072. The profiles of the profiled slot 2056, non-circular gear profile 2060 and non-circular gear follower 2062 may cause the trocar 2070 to rotate about the pitch axis. The shape of the arm 2051 may be straight or be curved as shown for tissue clearance.

The arm 2050 has one degree of freedom provided by the pitch mechanism. The arm 2050 can have one degree of freedom provided by a roll mechanism (not shown), with a roll axis 2058. Additional redundant degrees of freedom can be added to the arm 2050 to make the arm 2050 a hyperdexterous surgical arm. The hyperdexterous surgical tool (not shown) and the rotate/translate mechanism can provide four degrees of freedom, for a total of six degrees of freedom.

The pitch mechanism and the roll mechanism can be passive or active. In some embodiments, the motion of the arm 2050 may be actively controlled and may be manipulated by an energy source (e.g., motors such as electric motors, hydraulics, pneumatics, etc. not shown). The operator 1 can mount the arm 2050 to establish the Rotation Center 250.

Hyperdexterous Surgical Tool

The hyperdexterous surgical tool 300 and the rotate/translate mechanism 208 provides four degrees of freedom for the hyperdexterous surgical system 100. The rotate/translate mechanism 208 can both rotate and translate the hyperdexterous surgical tool 300. The smaller size of the rotate/translate mechanism 208 advantageously allows the hyperdexterous surgical arm 200 to be smaller in size, as discussed previously. The small size of the rotate/translate mechanism 208 enables the hyperdexterous surgical arm 200 to be smaller and lightweight, which among other things enables more free space around the patient 2.

The hyperdexterous surgical tool 300 can be rotated and/or translated by a rotate/translate mechanism 208. The rotate/translate mechanism 208 rotates the hyperdexterous surgical tool 300 along with the rotate/translate mechanism 208. The rotate/translate mechanism 208 translates the hyperdexterous surgical tool 300. The rotate/translate mechanism 208 can provide any combination of translation and/or rotation. The rotate/translate mechanism 208 can advantageously accommodate tool shafts of various diameters. The rotate/translate mechanism 208 accommodate tool shafts of any length. The mechanisms that interact with the tool shaft as described in FIGS. 17-22 are not limited to a specific number of rotations. Therefore the mechanism can accommodate a tool shaft of any length, which is an advantage over existing, on-market translation mechanisms which use telescoping segments that are inherently limited in range. The compact size of the rotate/translate mechanism 208 can be lighter, allowing for the use of a smaller hyperdexterous surgical arm.

The end effector provides two degrees of freedom (pitch, yaw) and can provide additional degrees of freedom (jaw actuation, pinch). Referring back to FIG. 10, the hyperdexterous surgical tool 300 includes the end effector 306, for example a grasper, a needle holder, a stapler, a cauterizing tool, deployed at the tip of an elongated shaft. The hyperdexterous surgical tool 300 can be introduced through a small incision in the body (e.g., of the patient 2).

FIG. 7 shows the hyperdexterous surgical arm 200 and the rotate/translate mechanism 208. The rotate/translate mechanism 208 provides two degree of freedom to the hyperdexterous surgical system 100 (rotate, translate). Among the degrees of freedom imparted by the rotate/translate mechanism are rotation of the hyperdexterous surgical tool 300 about the tool shaft axis 252 and linear translation of the hyperdexterous surgical tool 300 along the tool shaft axis 252 (see FIG. 10). The hyperdexterous surgical tool 300 may be rotated or translated without moving the Remote Center 250. The rotate/translate mechanism 208 imparts rotation and/or translation directly onto the hyperdexterous surgical tool 300 that is supported by the hyperdexterous surgical arm 200.

The rotation of the rotate/translate mechanism 208 is transformed into rotation of the hyperdexterous surgical tool 300. The translation of the rotate/translate mechanism 208 is transformed into translation of the hyperdexterous surgical tool 300. The direction and speed of the pulleys, geared wheels, or other engagement mechanisms of the rotate/translate mechanism 208 results in different types of motion of the hyperdexterous surgical tool 300.

The smaller size of the rotate/translate mechanism 208 may ensure that that the hyperdexterous surgical arm 200 can be smaller in size. The smaller size may reduce the chances for collision with other components of the hyperdexterous surgical system 100 (e.g., other hyperdexterous surgical arms 200, other segments). The smaller size of the proximal section of the hyperdexterous surgical tools 300 may ensure that that the hyperdexterous surgical tool 300 encounters fewer restrictions of movement. The smaller weight of hyperdexterous surgical tools 300 allows the use of drive mechanisms, such as motors, that are less bulky. Further, the need for large and powerful motors may be reduced.

The small size of the rotate/translate mechanism 208 enables more free space around the patient 2. The free space enables the surgeon to manipulate a manual tool 350 simultaneously with the hyperdexterous surgical tool 300 from various positions. The free space enables the surgeon to reposition himself at multiple locations during surgery. The free space enables the operator to use manual tools 350 concurrently with use of the hyperdexterous surgical arm 200. The free space permits easier physical access to the patient when necessary.

Due to the smaller space taken up by hyperdexterous surgical system 100, the operator 1, such as a surgeon or surgical team member, can advantageously enable more free space around the patient. The free space enables the operator 1 to readily gain access to the patient.

FIGS. 17-22 illustrate one embodiment of the rotate/translate mechanism 208. Two different types of rotate/translate mechanisms 208 will be discussed below—the asymmetric rotate/translate mechanism 258 and a symmetric rotate/translate mechanism 2500. There may be other types of rotate/translate mechanisms 208 as well. The rotate/translate mechanism 258, 2500 may use rollers, gears, pulleys, friction surfaces, etc. in either symmetric or asymmetric differential configurations. It may also be combined with the hyperdexterous surgical tool in order to minimize the number of discrete parts of the system and increase the ease of use and setup. The asymmetric rotate/translate mechanism 258 can include at least two pulleys, a pulley 260 and a pulley 262. The asymmetric rotate/translate mechanism 258 has a central housing 264 located through the centers of the pulleys 260, 262. The pulley 260 can be coupled to the central housing 264. The pulley 262 can rotate about the central housing 264. The hyperdexterous surgical tools 300 can be inserted through the central housing 264.

Figure 18:
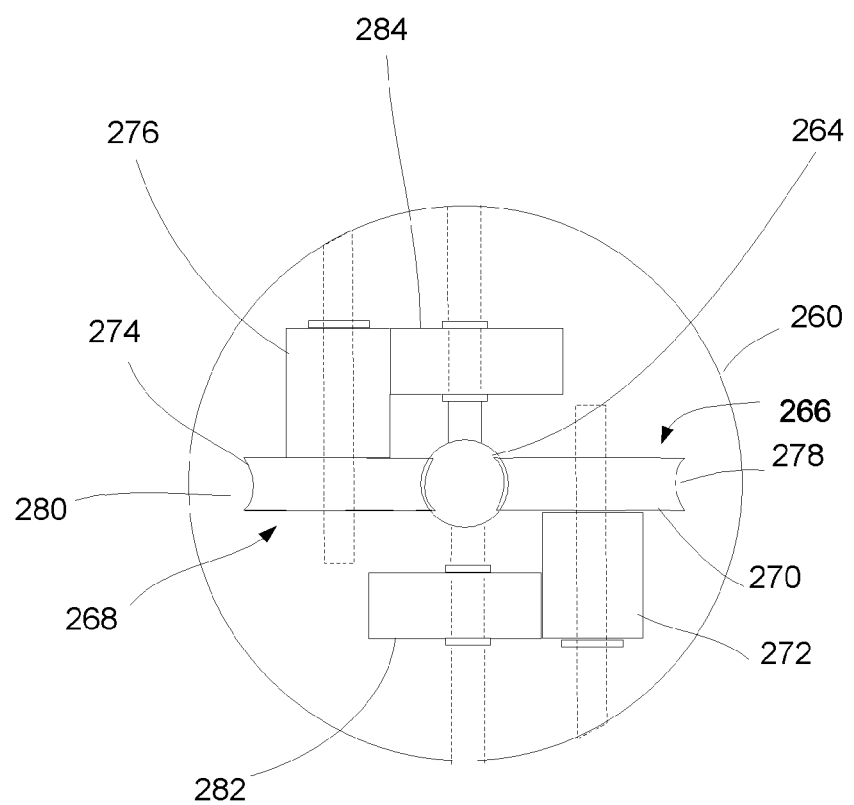
FIG. 18 schematically illustrates a top view of the asymmetric rotate/translate mechanism of FIG. 17.

The pulley 260 can include at least two rollers, a roller 266 and a roller 268. Referring now to FIG. 18, the roller 266 has a roller wheel 270 and a roller drum 272. The roller 268 has a roller wheel 274 and a roller drum 276. The diameter of the roller drums 272, 276 may be smaller than the roller wheel 270, 274. The roller wheel 270 has a concave surface 278 and the roller wheel 274 has a concave surface 280. The concave surfaces 278, 280 can conform to the shape of the hyperdexterous surgical tool 300 and facilitate the ability of the rollers 266, 268 to grip or engage the hyperdexterous surgical tool 300 through slots in the central housing 264. Although roller wheel 270 and roller wheel 274 are shown to have concave surfaces, various other surfaces may be utilized to engage the surface of the tool shaft of the hyperdexterous surgical tool 300, including but not limited to textured surfaces, gear teeth, and belts.

Figure 17:
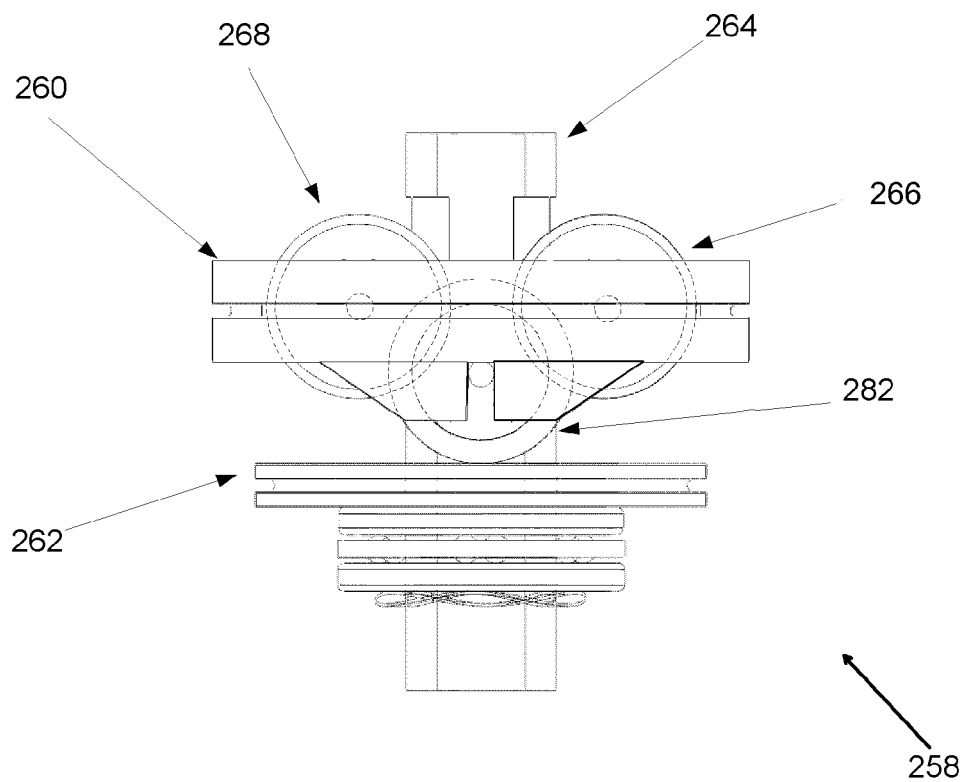
FIG. 17 schematically illustrates an embodiment of an asymmetric rotate/translate mechanism.

The pulley 260 includes at least two additional rollers, a roller 282 and a roller 284. The rollers 282, 284 are attached to the underside of the pulley 260. FIG. 17 shows the roller 282 attached to the underside of the pulley 260.

Figure 19:
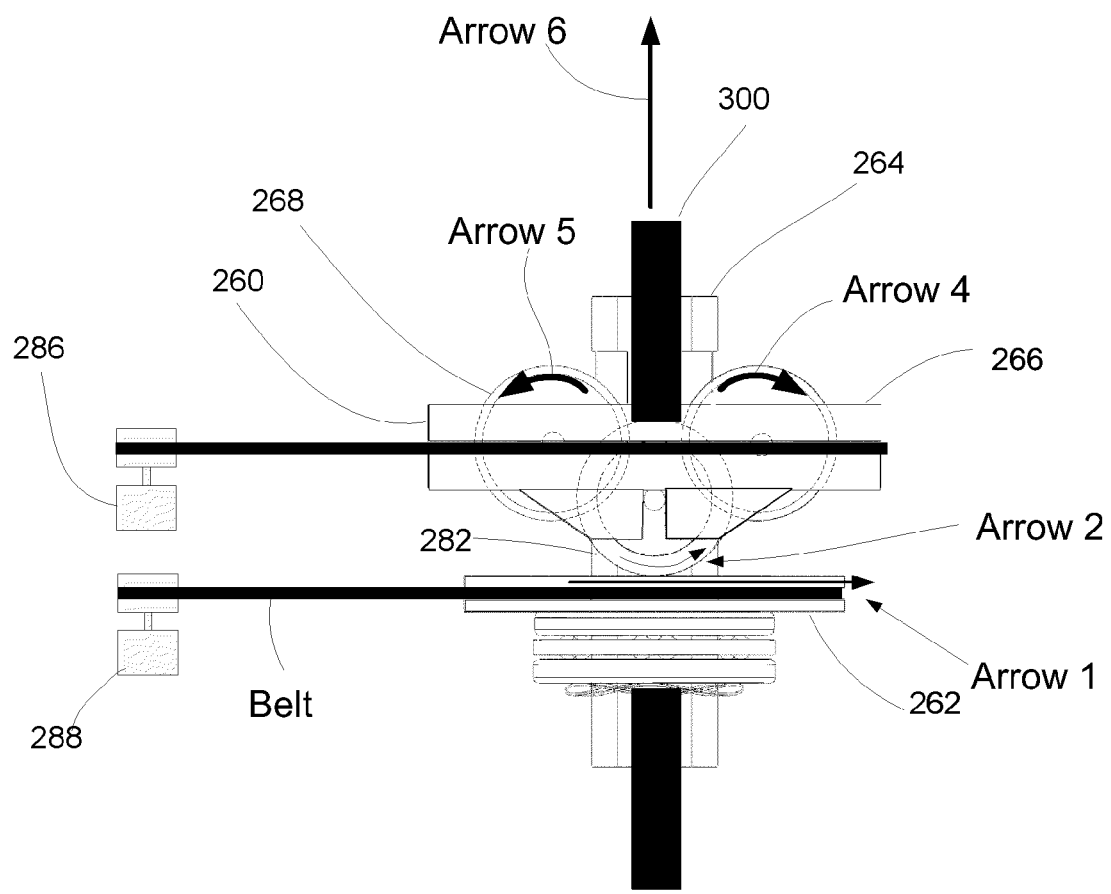
FIG. 19 schematically illustrates a side view of the asymmetric rotate/translate mechanism of FIG. 17 with arrows showing translation of a hyperdexterous surgical tool.
Figure 20:
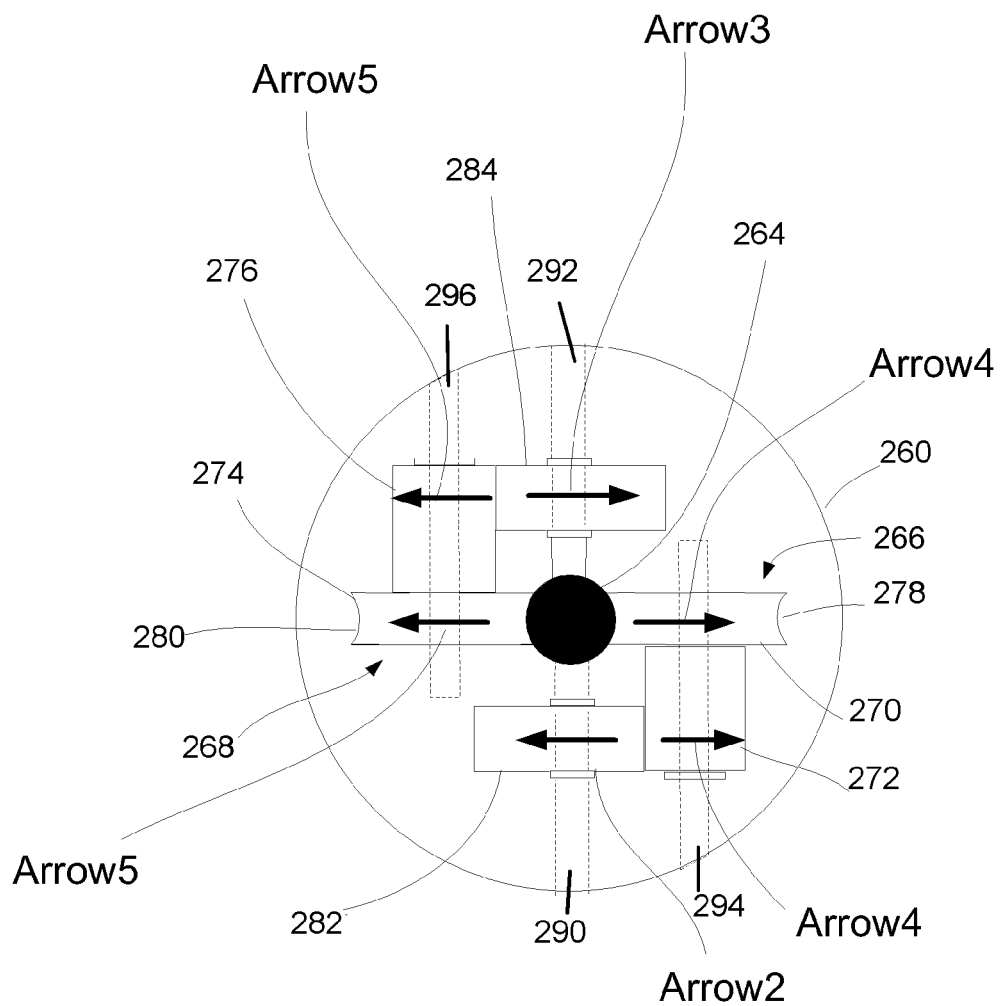
FIG. 20 schematically illustrates the top view of the asymmetric rotate/translate mechanism of FIG. 17 with arrows showing translation of a hyperdexterous surgical tool.

The process of translation of the hyperdexterous surgical tool 300 is shown in FIGS. 19 and 20. As shown in FIG. 19, a motor 286 drives the pulley 260 and a motor 288 drives pulley 262. As mentioned previously, the hyperdexterous surgical tool 300 can be inserted through the central housing 264. If the motor 288 is driven such that the pulley 262 rotates in the direction of Arrow 1, the roller 282 will rotate in the direction of Arrow 2. Turning to FIG. 20, which is the top view illustrating the same motion as shown in FIG. 19, the roller 282 is shown rotating in the direction of Arrow 2.

The roller 284 is not shown in FIG. 19. Turning to FIG. 20, which is the top view illustrating the same motion as shown in FIG. 19; the roller 284 is shown rotating in the direction of Arrow 3. The rotation of the rollers 282, 284 will cause the roller drum 272 and the roller drum 276 to rotate. The rotation of the roller drums 272, 276 will cause the roller wheel 270 and the roller wheel 274 to rotate. The rotation of the roller 266, including the roller wheel 270 and the roller drum 272, is shown by Arrow 4. The rotation of the roller 268, including the roller wheel 274 and the roller drum 276, is shown by Arrow 5.

The rotation of the roller wheel 270 of roller 266 and the rotation of the roller wheel 274 of roller 268 causes the hyperdexterous surgical tool 300 inserted in the central housing 264 to translate. However, the hyperdexterous surgical tool 300 must be allowed to uncouple from the central housing 264 to permit the use of a different hyperdexterous surgical tool 300. The hyperdexterous surgical tool 300 translates in the direction of Arrow 6, shown in FIG. 19. Arrow 6 is not shown in FIG. 20 as it would be perpendicular, out of the plane of the drawing. To translate the hyperdexterous surgical tool 300 in the downward direction, the motor 288 simply turns in the reverse direction, reverse to Arrow 1. This causes the motions of the rollers 266, 268, including the roller wheels 270, 274 and the roller drums 272, 276, to rotate in reverse. This causes the hyperdexterous surgical tool 300 to translate in the opposite direction to the direction shown in FIGS. 19 and 20.

Figure 21:
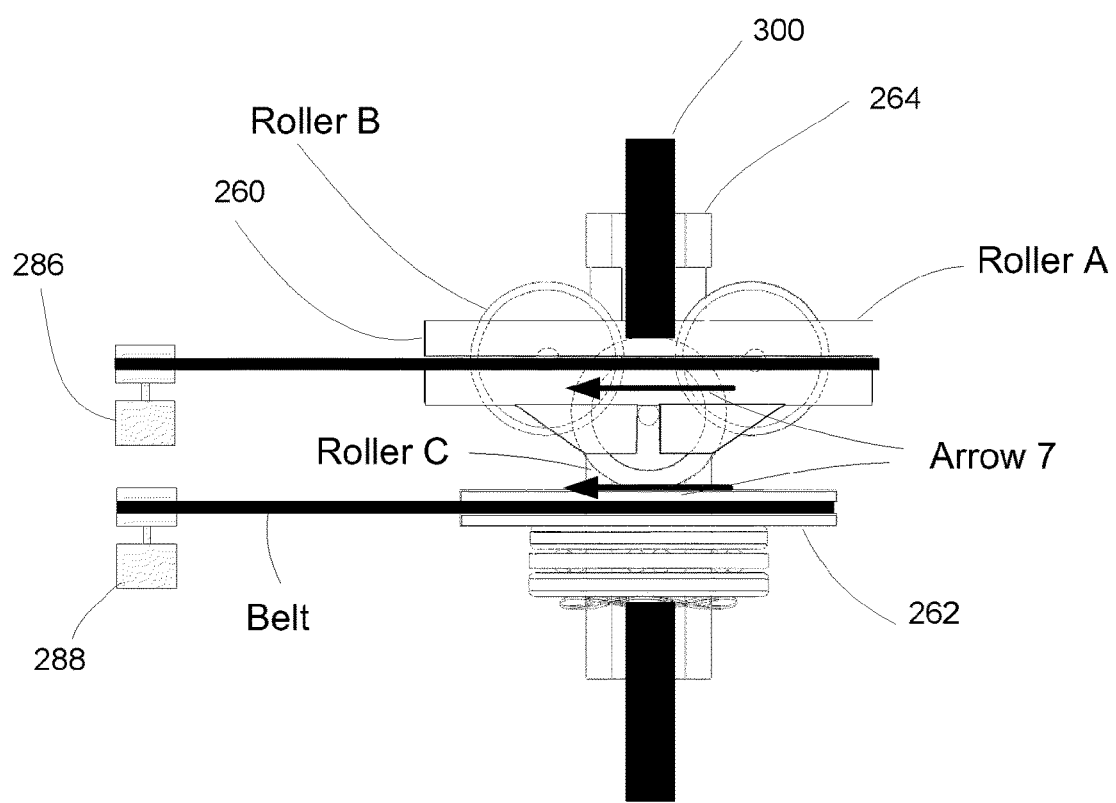
FIG. 21 schematically illustrates the side view of the asymmetric rotate/translate mechanism of FIG. 17 with arrows showing rotation of a hyperdexterous surgical tool.
Figure 22:
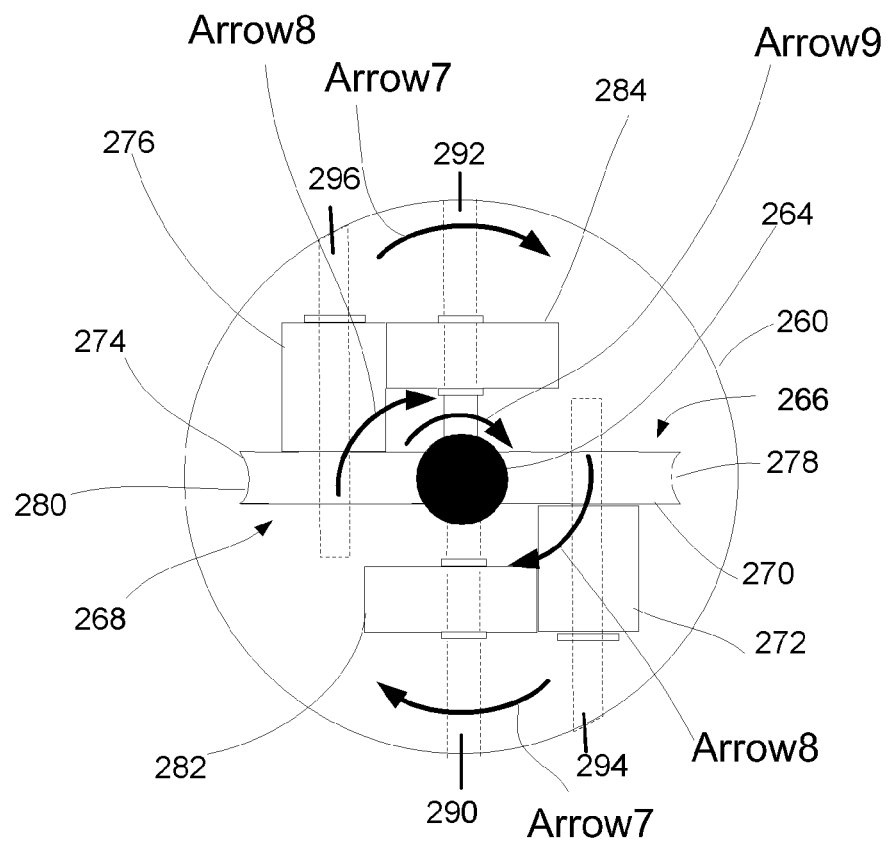
FIG. 22 schematically illustrates the top view of the asymmetric rotate/translate mechanism of FIG. 17 with arrows showing rotation of a hyperdexterous surgical tool.

The process of rotation of the hyperdexterous surgical tool 300 is shown in FIGS. 21 and 22. In FIG. 21, the pulley 260 and the pulley 262 are rotated by the motor 286 and the motor 288, respectively. Both pulleys 260, 262 are rotated in the same direction, shown by Arrow 7. Due to the motion of both motors 286, 288, the roller 282 will not rotate in the direction of Arrow 2, as shown in FIGS. 19 and 20. Due to the motion of both motors 286, 288, the roller 284 will not rotate in the direction of Arrow 3, as shown in FIG. 20. When both pulleys 260, 262 rotate in the same direction, the roller 282 and 284 do not rotate about their own rotation axes 290, 292. Subsequently, the rollers 266 and 268 do not rotate about their own rotation axes 294, 296, as shown in FIG. 20. The rollers 266, 268, 282, 284 do rotate with the pulley 260, as shown by Arrow 8 in FIG. 22. The pulley 260 rotates about the central housing 264. As the pulley 260 is rotated, the hyperdexterous surgical tool 300 rotates as shown by Arrow 9. To rotate in the other direction, the motors simply turns in the reverse direction, reverse to Arrow 7 shown in FIG. 21.

The rotate translate 258 uses engagement mechanisms such as rollers and friction wheels. Other types of engagement mechanism may additionally or alternatively be utilized including gears, belts, beveled gears, and cables.

Figure 23:
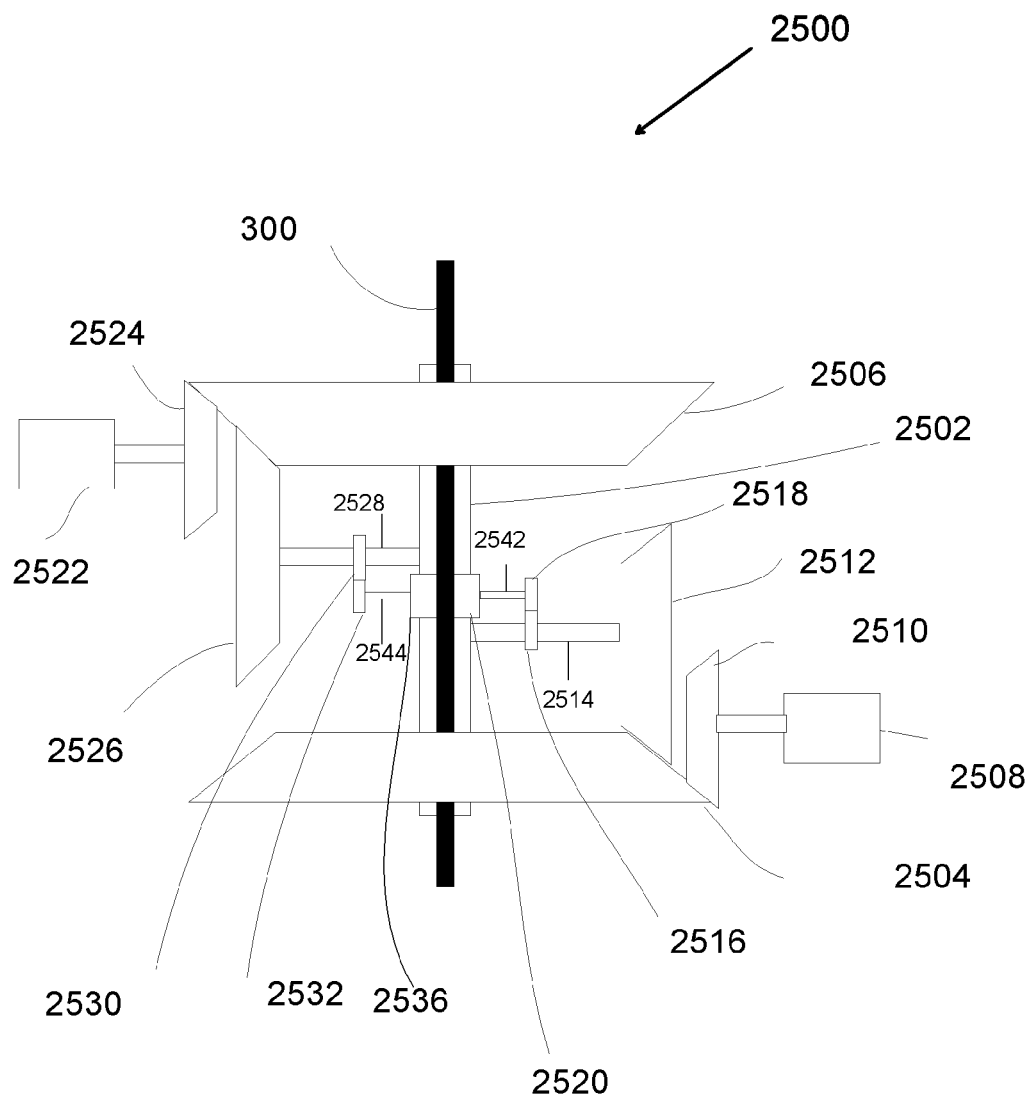
FIG. 23 schematically illustrates an embodiment of a symmetric rotate/translate mechanism.
Figure 24:
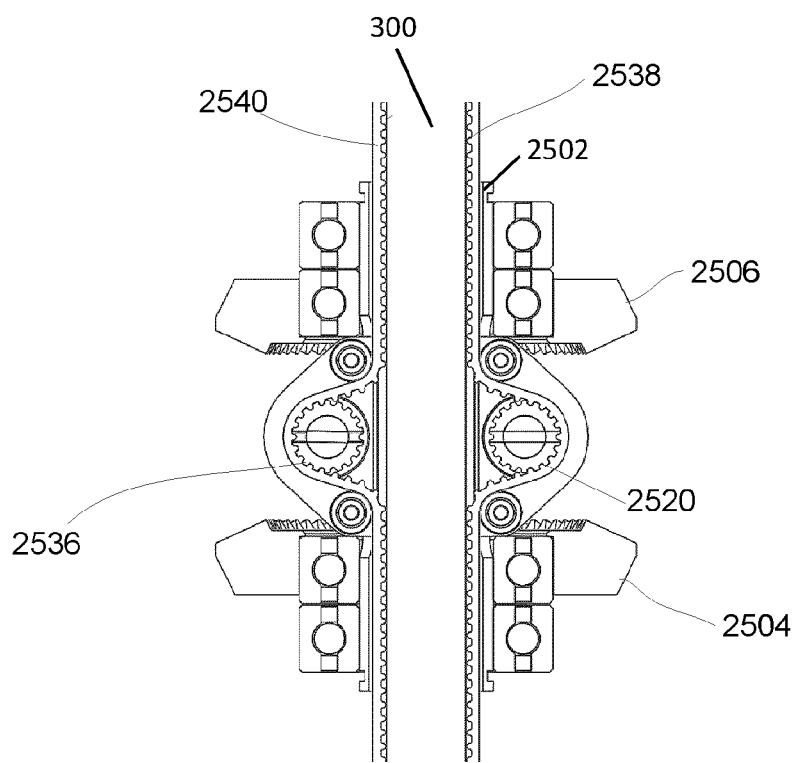
FIG. 24 schematically illustrates a side view of the symmetric rotate/translate mechanism of FIG. 23 showing the linear drive belts and the rollers of FIG. 23.

FIGS. 23-27 illustrate another embodiment of a rotate/translate mechanism 2500. This mechanism falls in the category of symmetric rotate/translate and differential rotate/translate mechanisms. The symmetric rotate/translate mechanism 2500 can include a beveled gear 2504 and a beveled gear 2506. In FIG. 23, the central housing 2502 is generally perpendicular to the beveled gears 2504, 2506. The beveled gears 2504, 2506 include teeth, which are shown in FIG. 24.

The motor 2508 (e.g., electric motor) includes motor gear 2510. The motor 2508 and motor gear 2510 drive beveled gear 2504. The beveled gear 2504 drives an inset beveled gear 2512. The inset gear 2512 and the inset gear 2526 are connected to the central housing 2502 but can rotate about their own central rotation axes. The inset beveled gear 2512 is coupled with the central housing 2502. The inset beveled gear 2512 rotates about the axle 2514. The axle 2514 is coupled to a secondary gear 2516. The secondary gear 2516 interfaces with a spur gear 2518. The spur gear 2518 is connected to a roller 2520.

The motor 2522 (e.g., electric motor) includes motor gear 2524. The motor 2522 and motor gear 2524 drive beveled gear 2506. The beveled gear 2506 drives an inset beveled gear 2526. The inset beveled gear 2526 is coupled with the central housing 2502. The inset beveled gear 2526 rotates about the axle 2528. The axle 2528 is coupled to a secondary gear 2530. The secondary gear 2530 interfaces with a spur gear 2532. The spur gear 2532 is connected with a roller 2536.

FIG. 24 shows the rollers 2520, 2536 and the beveled gears 2504, 2506. The symmetric rotate/translate mechanism 2500 includes a linear drive belt 2538 coupled with the roller 2520 and a linear drive belt 2540 coupled with the roller 2536. The roller 2520 is placed between the linear drive belt 2538 and the central housing 2502, so that the linear drive belt 2538 partially wraps around the roller 2520. The roller 2536 is placed between the linear drive belt 2540 and the central housing 2502, so that the linear drive belt 2540 partially wraps around the roller 2536. The linear drive belt 2538 and the linear drive belt 2540 can extend at least partially along the length of the hyperdexterous surgical tool 300 and are coupled to the shaft of the hyperdexterous surgical tool 300.

Figure 25:
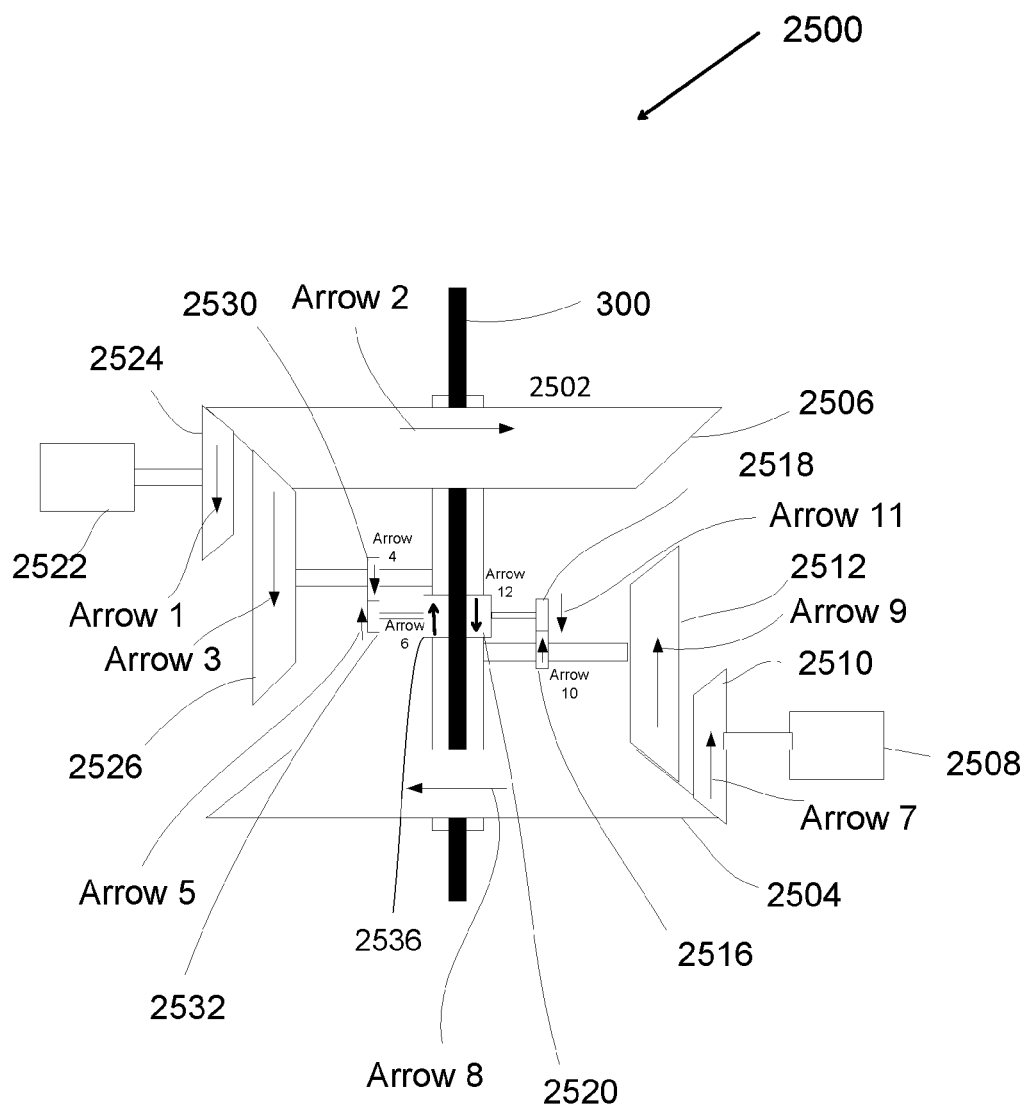
FIG. 25 schematically illustrates a side view of the symmetric rotate/translate mechanism of FIG. 23 with arrows showing translation of a hyperdexterous surgical tool.
Figure 26:
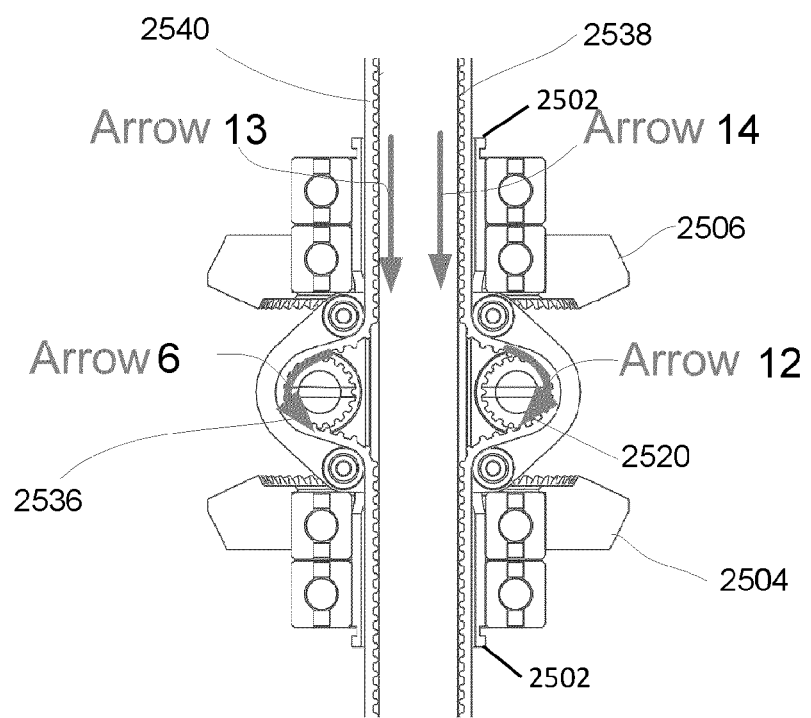
FIG. 26 schematically illustrates the side view showing the linear drive belts and the rollers of the symmetric rotate/translate mechanism of FIG. 23 with arrows showing translation of a hyperdexterous surgical tool.

The process of translation of the hyperdexterous surgical tool 300 is shown in FIGS. 25 and 26. The motor 2522 is rotated as shown in the direction of Arrow 1. This causes the beveled gear 2506 to rotate in the direction of Arrow 2. The beveled gear 2506 causes the inset beveled gear 2526 to rotate in the direction of Arrow 3. The rotation of inset beveled gear 2526 causes the secondary gear 2530 rotate in the same direction as Arrow 4. The rotation of the secondary gear causes 2530 the spur gear 2532 to rotate in the direction of Arrow 5. The rotation of the spur gear 2532 causes the roller 2536 to rotate in the direction of Arrow 6. Referring now to FIG. 26, the roller 2536 rotates in the direction of Arrow 6.

The motor 2508 is rotated as shown in the direction of Arrow 7. This causes the beveled gear 2504 to rotate in the direction of Arrow 8. The beveled gear 2504 causes the inset beveled gear 2512 to rotate in the direction of Arrow 9. The rotation of inset beveled gear 2512 causes the secondary gear 2516 rotate in the direction as Arrow 10. The rotation of the secondary gear 2516 causes the spur gear 2518 to rotate in the direction of Arrow 11. The rotation of the spur gear 2518 causes the roller 2520 to rotate in the direction of Arrow 12. Referring now to FIG. 26, the roller 2520 rotates in the direction of Arrow 12. The rollers 2520 engage opposite sides of the hyperdexterous surgical tool 300, as shown in FIG. 26. In FIGS. 23 and 25, the roller 2520 is behind the central housing 2502 and the hyperdexterous surgical tool 300 and is therefore shown in dashed lines.

The rotation of the rollers 2520, 2536 will cause linear translation of the linear belt drives 2538, 2540 in the direction indicated by Arrow 13 and Arrow 14 in FIG. 26. The motion of the linear belt drives 2538, 2540 causes linear translation of the hyperdexterous surgical tool 300. The linear belt drives 2538, 2540 are coupled to the tool shaft of the hyperdexterous surgical tool 300, and the hyperdexterous surgical tool 300 translates through the central housing 2502. A hyperdexterous surgical tool 300 inserted in the central housing 2502 would translate in the direction of Arrow 13 and Arrow 14. To move the hyperdexterous surgical tool 300 in the upward direction, the motors 2508, 2522 would simply rotate in the opposite direction, a direction opposite to Arrow 1 and Arrow 7 in FIG. 25.

Figure 27:
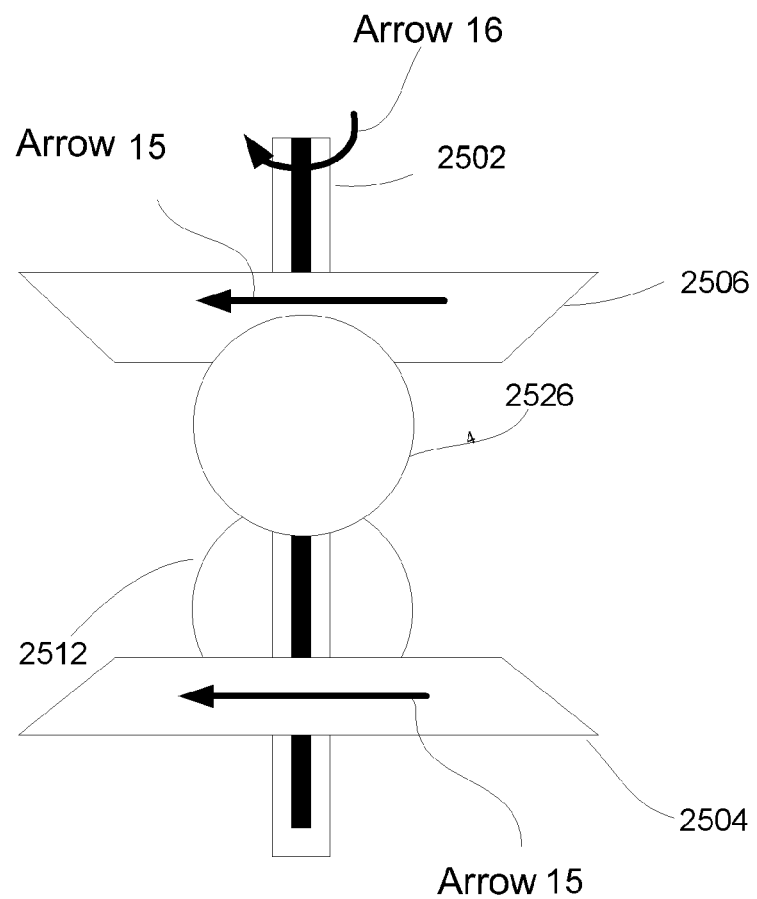
FIG. 27 schematically illustrates the side view of the symmetric rotate/translate mechanism of FIG. 23 with arrows showing rotation of a hyperdexterous surgical tool.
Figure 28:
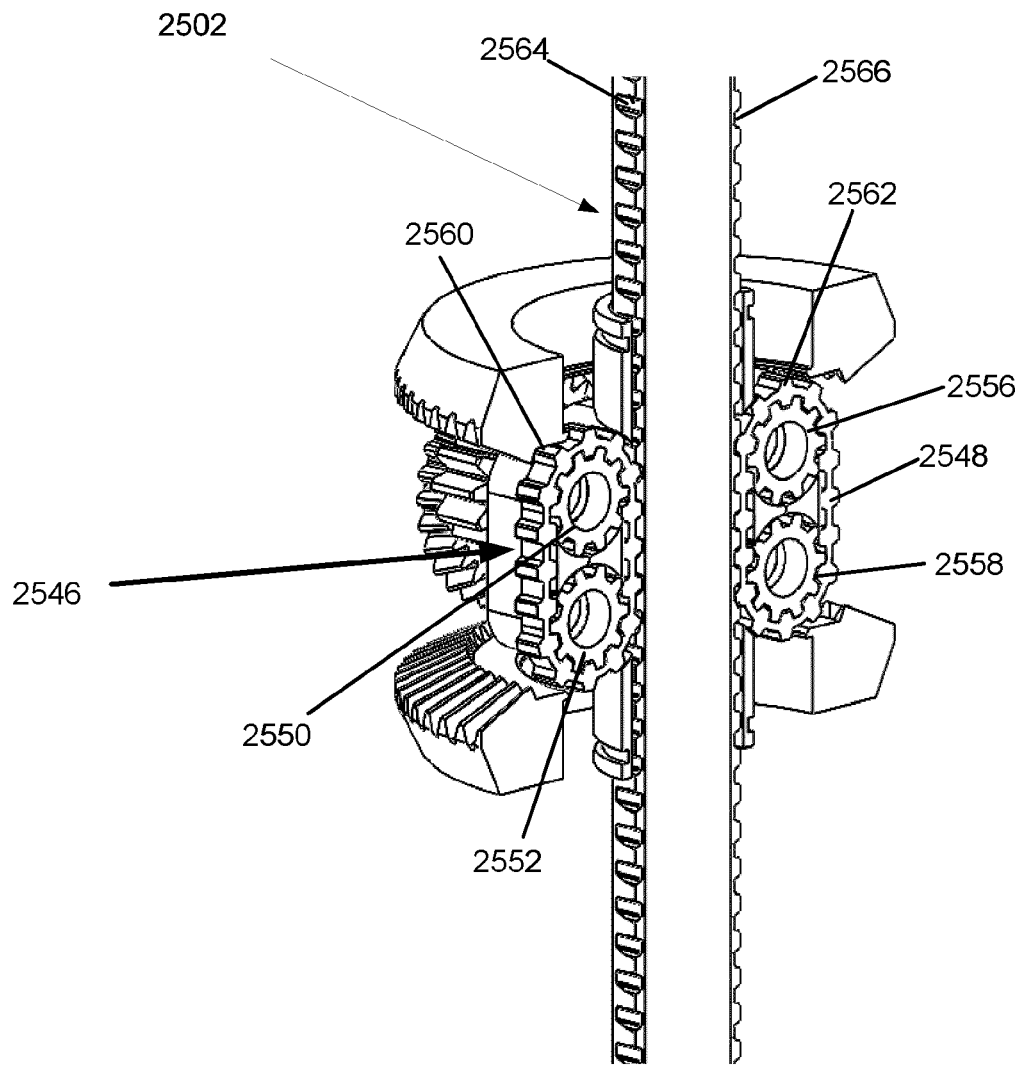
FIG. 28 schematically illustrates an embodiment of a rotate/translate mechanism with a continuous belt drive mechanism.

The process of rotation of the hyperdexterous surgical tool 300 is shown in FIGS. 27 and 28. The motors, motor gears, secondary gears, spur gears and rollers below the linear belt drive are not shown. In addition, the teeth for the beveled gears and the inset gears are not shown. In FIG. 27, the beveled gears 2504, 2506 are rotated by the motors (not shown). Both beveled gears 2504, 2506 are rotated in the same direction, shown by Arrow 15. Due to the motion of both motors, the inset beveled gears 2512, 2526 will not rotate in the direction of Arrow 3 and 9, as shown in FIG. 22.

Due to the motion of both motors, the rollers 2520, 2536 rotate with the beveled gears 2504, 2506, as shown by Arrow 16 in FIG. 27. The rotation of both bevel gears 2504, 2506 in the same direction causes the central housing 2502 and the captured hyperdexterous surgical tool 300 to all rotate at the same speed. As the beveled gears 2504, 2506 are rotated, the hyperdexterous surgical tool 300 rotates as shown by Arrow 16. To rotate in the other direction, the motors simply turn in the reverse direction.

Due to the motion of both motors 2508, 2522, the inset beveled gears 2512, 2526 rotate with the beveled gears 2504, 2506. The inset beveled gears 2512, 2526 are coupled with the central housing 2502. The rotation of the bevel gears 2504, 2506, and the inset beveled gears 2512, 2526 in the same direction causes the central housing 2502 and the captured hyperdexterous surgical tool 300 to all rotate at the same speed. The engagement mechanisms such as gears, belts, and beveled gears can be utilized in the rotate/translate mechanism 208. Other types of engagement mechanism may additionally or alternatively be utilized in other embodiments such as rollers, bearings, and cables.

FIG. 28 illustrates an alternative embodiment of the linear belt drives 2538, 2540 and rollers 2520, 2536 of FIGS. 23-27. The embodiment includes smaller continuous belt drives 2546, 2548. The belt drive 2546 surrounds two rollers 2550, 2552. The belt drive 2548 surrounds two rollers 2556, 2558. The teeth 2560, 2562 for the belt drives 2546, 2548 are placed on the outside surface of the belt drives 2546, 2548. The teeth 2560, 2562 for the belt drives 2546, 2548 engage the teeth 2564, 2566 on the outside surface of the central housing 2502 or directly on the tool shaft of the hyperdexterous surgical tool 300. Although belt drives are used to engage the central housing 2502 or the tool shaft of the hyperdexterous surgical tool 300 in the illustrated embodiment, various other suitable mechanisms may be utilized to engage the central housing 2502 or the tool shaft of the hyperdexterous surgical tool 300.

The rotate/translate mechanism 208 can provide any combination of translation or rotation. Referring back to FIG. 23, assume that the anticlockwise rotation of the motor 2508 and the anticlockwise rotation of the motor 2522 is assigned a "+" direction and the clockwise rotation of motor 2508 and 2522 is assigned a "−" direction. Further also assume that one unit of translation of the central housing 2502 or the tool shaft of the hyperdexterous surgical tool 300 in the downward direction is called "T+" and one unit of clockwise rotation of the central housing 2502 is called "R+". This nomenclature may be reversed without changing the concept. It must be further noted that the one translation unit may not correspond with an integral units of distance, such as 1 cm. Similarly one rotation unit may not correspond to a complete rotation of the central housing 2502. The conversion of these units to actual distance or degrees depends on the gear ratio selected.

Assuming that one unit of rotation of the motor 2508 or "MA+" produces one translation unit in the positive direction and one rotation unit of the central housing 2502 in the positive direction. Thus:

$$MA_+ = T_+ + R_+ \qquad \text{Eqn. 1}$$

Similarly, one unit of rotation of the motor 2522 or MB+ produces one translation unit in the positive direction and one rotation unit of the central housing 2502 in the negative direction. Thus:

$$MB_+ = T_+ + R_- \qquad \text{Eqn. 2}$$

For example, to get two units of translation in the positive direction:

$$MA_+ + MB_+ = 2T_+ \qquad \text{Eqn. 3}$$

To get one unit of rotation in the negative direction $$\tfrac{1}{2}MA_- + \tfrac{1}{2}MB_+ = R_- \qquad \text{Eqn. 4}$$

Thus any combination of translation and/or rotation may be obtained by combining the motions of the motors 2508, 2522 including the combination where one motor does not move. In some embodiments, the speed of translation and rotation may be varied using the same concepts. The speed of the motors 2508, 2522 may be set as a predetermined value. In some embodiments, through the display 600, an operator 1 (e.g., surgeon) may want to choose a slower, more sensitive setting, whereas another operator may prefer a less sensitive setting. This is analogous to a setting the sensitivity settings of a computer mouse where the response of the pointer on the screen may follow the user settings based on preference settings.

In some embodiments, the translation unit and the rotation unit may correspond to actual distances and actual degrees of rotations. The conversion values may be determined during the design stage of the hyperdexterous surgical arm 200 or may be determined via a calibration procedure. The conversion values may be stored in memory within the control system 400. Due to play in the components and other factors, each motor 2508, 2522 may not result in exactly the same amount of translation and rotation. In this case, these differences may be accounted by the control system 400 and in the equations described above.

Figure 29:
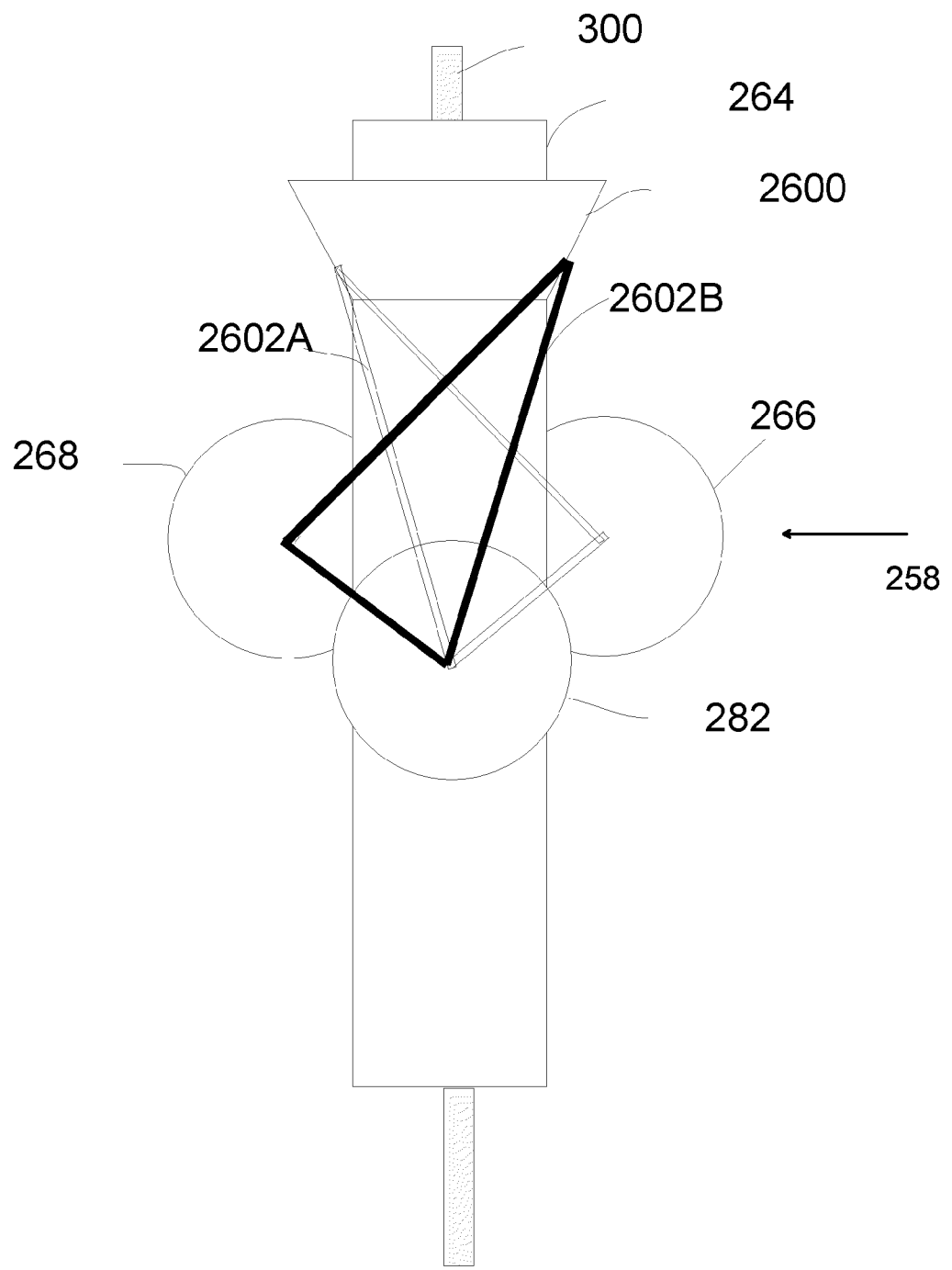
FIG. 29 schematically illustrates an embodiment of a width adjuster mechanism.
Figure 30:
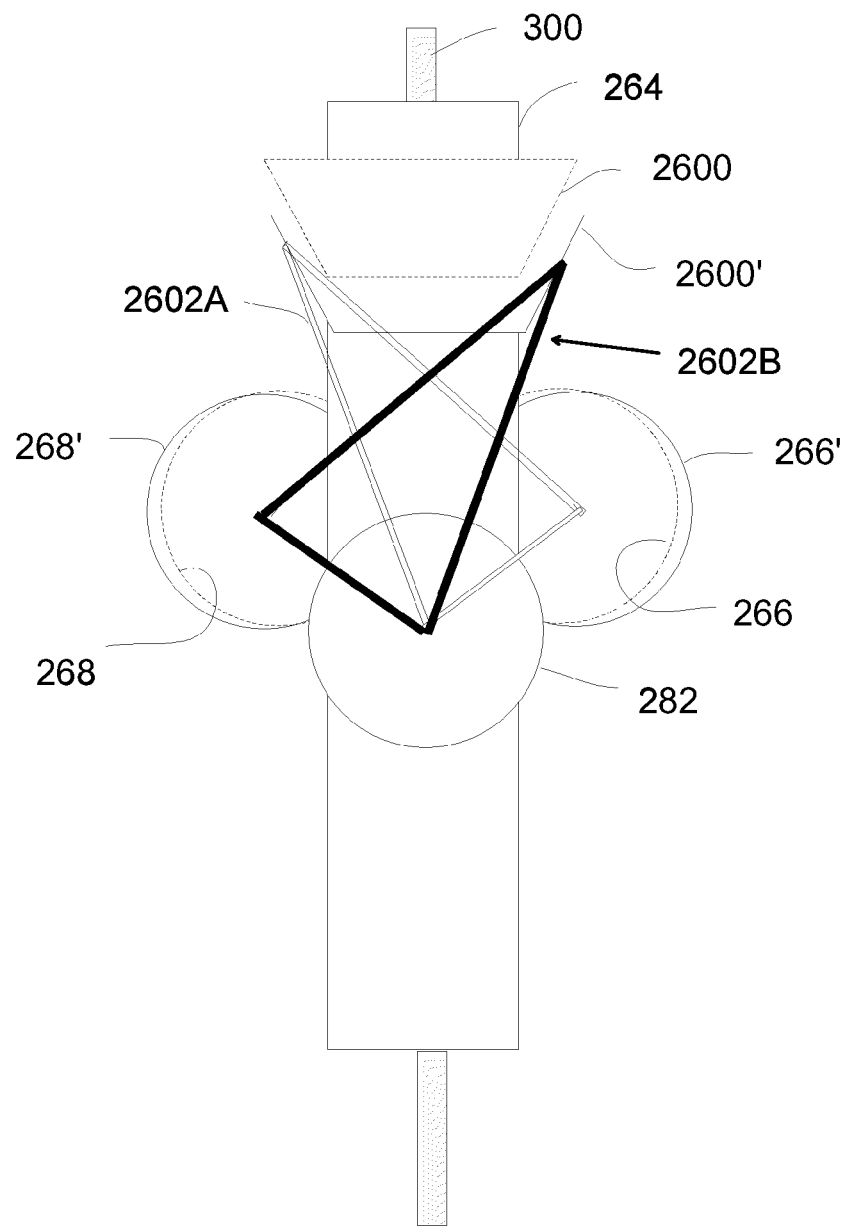
FIG. 30 schematically illustrates the side view of the width adjuster mechanism of FIG. 29 in a new position.
Figure 31:
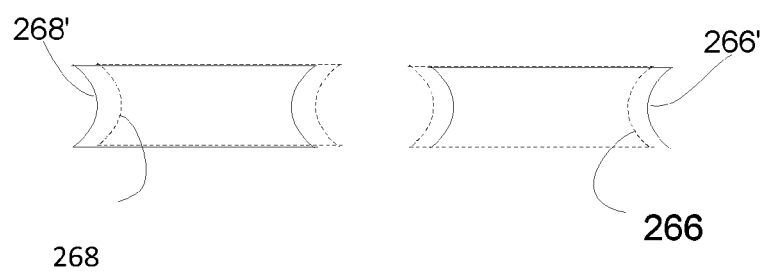
FIG. 31 schematically illustrates the top view of the new position of the rollers of FIG. 30.

The rotate/translate mechanism 208 can advantageously accommodate tool shafts of various diameters. FIGS. 29-31 show a width adjuster 2600 coupled to the asymmetric rotate/translate mechanism 258, described herein. The width adjuster 2600 can be coupled to the symmetrical rotate/translate mechanism 2500. FIG. 29 shows a side view of the width adjuster 2600, coupled to the central housing 264. The width adjuster 2600 may move up and down along the length of the central housing 264. The width adjuster can have a plurality of links 2602A, 2602B, 2602C (not shown), 2602D (not shown) attached to the rollers 266, 268, and 282. A link can be attached to roller 284 (not shown). The links 2602A, 2602B may be arranged in a triangular shape. The links 2602A connect the width adjuster 2600 to the roller 266 and the roller 282 in a generally triangular shape. The links 2602B connect the width adjuster 2600 to the roller 268 and the roller 282 in a generally triangular shape. The links 2602C connect the width adjuster 2600 to the roller 266 and the roller 284 in a generally triangular shape (not shown). The links 2602D connect the width adjuster 2600 to the roller 268 and the roller 284 in a generally triangular shape (not shown). The triangle shape is an example of shapes that can be deployed, and other shapes are possible. The links 2602 can be solid pieces.

The links 2602 pivot around the axis of rotation of the rollers 282 and 284. The links 2602 can adjust the position of the centers of roller 266 and 268. The rollers 266, 268 have shafts that extend along their rotation axis 294, 296. The shafts of the rollers 266 and 268 are coupled to the links 2602.

The width adjuster 2600 can translate along the axis of the central housing 264. When the width adjuster 2600 moves downward, the links 2602 pivot to assume a new position. The links pivot around the axes 290, 292 of the rollers 282, 284. In this new position of the links 2602, the rollers 266, 268 assume a new position, as shown in FIG. 31. The new position of rollers 266', 268' permit a hyperdexterous surgical tool 300 of a greater diameter to be inserted into the central housing 264. As shown in FIGS. 30-31, the old position of the rollers 266, 268 is shown in dashed lines, while the new position of the rollers 266', 268' is shown is shown in solid lines. There is more space between the roller in the new position 266' and 268'.

In another example, in obese patients the manipulation of tools becomes difficult due to the body habitus; in these cases a larger or longer hyperdexterous surgical tool 300 can be supported by the hyperdexterous surgical arms 200. The width adjuster 2600 enables larger diameter tools to be used. The rotate/translate mechanism 208 enables the uses of longer tools.

In other aspect of the invention, it is often desirable to know how far a hyperdexterous surgical tool 300 is inserted into the body of a patient 2. In a surgical setting, the hyperdexterous surgical tool 300 is inserted into the body of the patient 2, such as the abdomen of the patient 2. It may be advantageous to know how much of the hyperdexterous surgical tool 300 is inside the body of the patient 2 and/or know how much of the hyperdexterous surgical tool 300 is outside the body. This distance may be determined by monitoring and calculating electrical parameters such as resistance or capacitance of the section of the hyperdexterous surgical tool 300 that is outside the body of the patient 2.

A contact between the body of the patient 2 and the hyperdexterous surgical tool 300 is made at the point of entry. An electrical circuit may be completed between a set point on the hyperdexterous surgical tool 300 outside the patient and the contact point on the hyperdexterous surgical tool 300 at the point of entry. As the hyperdexterous surgical tool 300 is manipulated, electrical parameters such as resistance or capacitance between the set point and the contact point may change. This change may be monitored and further processed (e.g., by the control system 400) to calculate the ratio of the tool outside the patient 2 to the ratio of the tool inside the patient 2.

Input Devices

The input devices 500 control the hyperdexterous surgical arm 200 and/or the hyperdexterous surgical tools 300. The input devices 500 can be wireless and/or portable allowing the operator to move about the patient 2. The input devices 500 allow the operator to be at various locations within the operating arena (e.g., various locations at the patient's bedside). The input devices 500 enable the operator to control the hyperdexterous surgical tools 300 and the manual tool 350 simultaneously. The simultaneous manipulation the hyperdexterous surgical tool 300 and the manual tools 350 advantageously reduces the need for a surgical assistant to manipulate the manual tools 350 while the operator controls the hyperdexterous surgical tool 300. The input device 500 of the present invention can take a number of forms including the pincher 502 (see FIG. 32A) and the controller 514 (see FIG. 2).

The input devices 500 can be wireless or wired. In some embodiments, the input devices 500 are handheld, portable devices that can be carried by the operator allowing the operator to move about the patient 2 and operate the input devices 500 from various locations (e.g., various bedside locations) during use of the hyperdexterous surgical system 100. The operator 1 can therefore move around the operating arena and control the hyperdexterous surgical arm 200 from various locations, as illustrated in FIGS. 3A-3C.

Figure 32A:
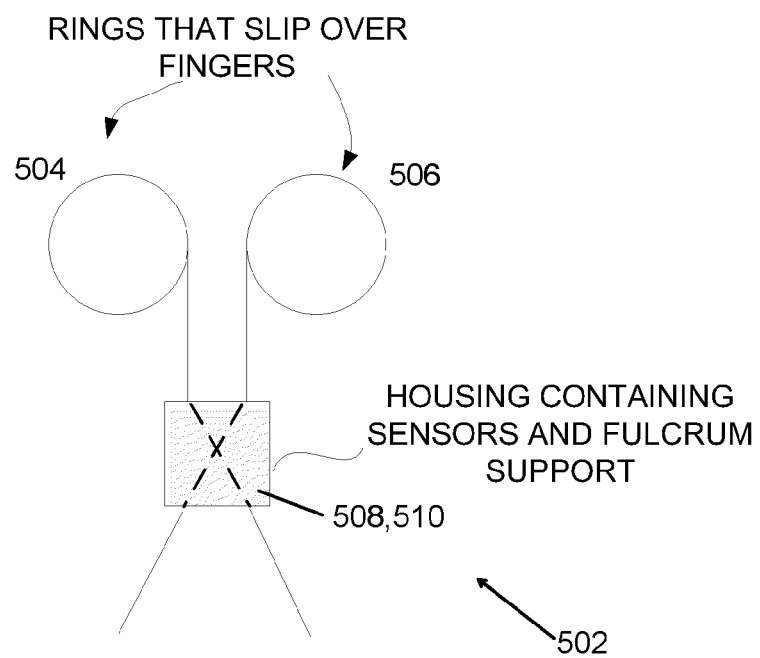
FIG. 32A is an embodiment of an input device.

In some embodiments, the input device 500 can be coupled to the body of the operator 1. FIG. 32A shows the pincher 502. The pincher 502 may assist the operator 1 in controlling a hyperdexterous surgical tool 300 in a manner consistent with holding the hyperdexterous surgical tool 300 with the thumb and the forefinger. The pincher 502 may assist the operator 1 in controlling a hyperdexterous surgical tool 300 at a control point such as the tool tip.

The operator 1, such as a surgeon, wears the two rings 504, 506 of the pincher 502. One ring 504 can be placed around the thumb of the operator 1 and one ring 506 can be placed around the forefinger of the operator 1. However, the rings 504, 506 can be worn on other fingers based on the configuration of the pinchers. There may be an association with the motion of the input device 502 and the motion of a tool tip or the end-effector 306.

The pincher 502 may have various sensors 508 such as position sensors and gyroscopes. Additional sensors 510 such as strain sensors may also measure the distance between the two arms of the pincher 502. The sensors 508, 510 can provide information related to the position and orientation of the pincher 502 to the control system 400. The information from these sensors 508, 510 serve as inputs to the control algorithms such that the hand, wrist and finger movement of the operator 1 may be translated to motion of the control point. The movements of the input device 502 can control the movements of the hyperdexterous surgical arm 200, the hyperdexterous surgical tool 300, and/or the end-effector 306 of the hyperdexterous surgical tool 300, such as a gripper. In one embodiment, the pincher 502 can include a power source such as a button cell (not shown).

In some embodiments, a second a pair of rings can be provided. The second pair of rings can be worn on other fingers of the same hand. The operator 1 may wear the second pair of rings around other fingers so that various motions of the hand may be translated to specific commands. The second pair of rings can be worn on different fingers of the same hand controlling the pincher 502. One ring of the second pair of rings can be placed around the thumb of the operator 1 and one ring of the second pair of rings can be placed around the last finger of the operator 1. As a non-limiting example, the first pair of rings 504, 506 of the first pincher 502 can control a first hyperdexterous surgical tool 300 and the second pair of rings can control a second hyperdexterous surgical tool 300. As a non-limiting example, the first pair of rings 504, 506 of the first pincher 502 and the second pair of rings can control the same hyperdexterous surgical tool 300.

In some embodiments, the second pair of rings and/or a second pincher 502 can be worn on the other hand. The second pair of rings and/or a second pincher 502 can be worn on a different hand of the operator 1 than the hand controlling the first pincher 502. As a non-limiting example, the first pair of rings 504, 506 of the first pincher 502 can control a first hyperdexterous surgical tool 300 and the second pair of rings and/or the second pincher 502 can control a second hyperdexterous surgical tool 300. As a non-limiting example, the first pair of rings 504, 506 of the first pincher 502 and the second pair of rings and/or the second pincher 502 can control the same hyperdexterous surgical tool 300 (e.g., at different control point).

The movement of the pincher 502 described herein can cause the movement of any control point. The control point can control the end effector (e.g., a grasper motion). However, the input devices 500 need not only control the end effector 306 or tip of a hyperdexterous surgical tool 300. The input devices 500 can control any part of the hyperdexterous surgical tool 300 by assigning a control point any location along the hyperdexterous surgical tool 300 (e.g., via the display 600). The control point can be considered a hypothetical location from which the operator 1 is controlling the tool (e.g., a fulcrum). The control point can be created anywhere along the hyperdexterous surgical tool 300, the hyperdexterous surgical arm 200, or any component of the hyperdexterous surgical system 100.

In some embodiments, the input device 500 is held by the operator 1. FIG. 32B shows another embodiment of an input device 500. In the illustrated embodiment, the input device 500 can be a knob 503. The operator 1, such as a surgeon, can hold the knob 503 with the one or more fingers of a hand. The knob 503 can have one or more buttons 505. A control point of the hyperdexterous surgical tool 300 can be moved or actuated when the operator squeezes at least one of the one or more buttons 505.

In some embodiments, the input device 500 is fixed relative to the operator 1. One embodiment is shown in FIG. 2. The hyperdexterous surgical system 100 can include a platform 602. The input device 500 can be coupled to the platform 602. The input device 500 can be coupled to any fixture within the operating arena. The input device 500 can take the form of a controller 514. The controller 514 can be wired or wireless. The user interface sub-system 605 allows an operator 1, such as a surgeon, to control the wired controller 514 in close proximity to the display 600, as shown in FIG. 2. The wired controller 514 can be located below this display 600. The platform 602 may also include a horizontal resting bar 603.

For example, if the operator 1 during the course of the surgery decides to sit and control the hyperdexterous surgical tools 300, the controller 514 would allow him or her to do that. For certain surgical procedures, the operator 1 may find it more comfortable to move a fixed input device such as the wired controller 514 rather than an input device 500 attached to the operator's body such as pincher 502. For instance, the operator 1 may be able to control his or her movements better while resting against the horizontal resting bar 602 and/or sitting. The natural body position of the operator may be to rest a portion of his or her body against the horizontal resting bar 603 while controlling the wired controller 514. The operator 1 can control other input devices 500 (e.g., pincher 502) while resting against the horizontal resting bar 603.

The hyperdexterous surgical system 100 can be controlled from multiple locations in the surgical arena. In some embodiments, the operator 1 can sit or stand while holding or otherwise controlling one or more input devices 500 (e.g., pincher 502, wired controller 514). The operator can support a portion of his or her body on the resting bar 603. The various input devices 500 allow the operator 1 to move around and place him or herself in the most optimal position.

The input device 500 controls the movement of one or more control points. The control points are locations which have the capability to execute some motion. Control points can be located on the hyperdexterous surgical arm 200, hyperdexterous surgical tools 300, or any other location. The hyperdexterous surgical tools 300 can be controlled by the input devices 500 relative to one or more control points 2600. The control points 2600 are locations on the hyperdexterous surgical arm 200 and/or the hyperdexterous surgical tool 300 which have the ability to move. The input by the operator 1 effects the movement of the one or more sections that are connected to the control point 2600.

The operator 1 can associate a control point 2600 with the input device 500 being manipulated. Moving the input device 500 causes the hyperdexterous surgical arm 200 and/or the hyperdexterous surgical tool 300 to move about the control point. The movement of the input device 500 would cause movement of the selected control point 2600. This would cause movement of the hyperdexterous surgical tool 300 that is controlled by the hyperdexterous surgical arm 200. The display 600 may be used to assign an input device 500 to a specific control point 2600.

Figure 33A:
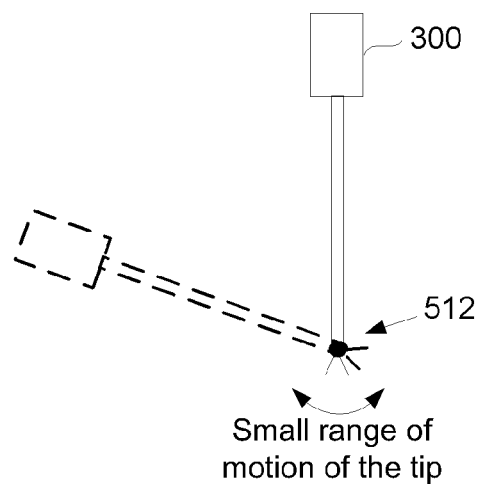
FIGS. 33A-33B schematically illustrate a virtual grip.
Figure 33B:
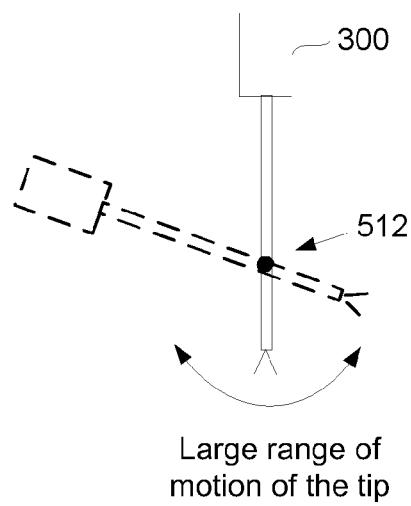

The hyperdexterous surgical tools 300 can be controlled by the input devices 500 relative to one or more virtual grips 512. The virtual grip 512 can increase the flexibility with which the hyperdexterous surgical tools 300 are positioned within the patient 2. FIGS. 33A and 33B show a hyperdexterous surgical tool 300. In FIG. 33A, the virtual grip 512 is placed at the end of the hyperdexterous surgical tool 300. If the hyperdexterous surgical tool 300 were to be constrained to move about the location of the virtual grip 512, then the tool tip and end effector 306 could only swing a small distance. In FIG. 33B, the virtual grip 512 is placed towards the middle of the hyperdexterous surgical tool 300. The tool tip and end effector 306 can swing a larger distance. The virtual grip 512 allows the operator 1 such as a surgeon to decide between fine motion and coarse motion. By moving the virtual grip 512 toward the tool tip, the operator can complete finer maneuvers. If multiple hyperdexterous surgical tools 300 are used, then each tool may have a different virtual grip 512. Further, different virtual grips 512 can be activated by different input devices 500, such that each virtual grip 512 is independently controlled. For example, the left hand with one input device 500 may control a hyperdexterous surgical tool 300 with a virtual grip near the end-effector, as shown in FIG. 33A. The right hand with another input device 500 may control the same hyperdexterous surgical tool 300 with the virtual grip 512 placed in the middle of the hyperdexterous surgical tool 300, as shown in FIG. 33B.

As described herein, the operator 1 may control a hyperdexterous surgical tool 300 by associating a virtual grip 512 to the tool tip. With his or her other hand, the operator 1 may associate a virtual grip 512 to the proximal end of the hyperdexterous surgical tool 300 (e.g., the same hyperdexterous surgical tool 300 or a different hyperdexterous surgical tool 300). The virtual grip at the proximal end would allow the operator 1 to control the hyperdexterous surgical tool 300 similar to how he or she controls a laparoscopic tool. The natural control of the hyperdexterous surgical tool 300 in this manner may be accomplished by associating independent frames of reference to each of the operator's hands, as described herein.

The position of the input device 500 in space may be tracked. In some embodiments, the position is tracked by coupling absolute encoders (not shown) to the input device 500. In some embodiments, a position sensor (optical tracker) is mounted at the base of the input device 500. In some embodiments, the input device 500 is tracked by a sensor that the operator 1 wears. In some embodiments, the input device 500 is tracked by a sensor on the platform 602. The position sensor can provide the position of the input device 500 relative to a ground reference point (not shown). The position sensor and/or the encoders can be utilized to track the position of the input device 500. One skilled in the art may utilize others suitable sensors, mechanism or methods of tracking components of the hyperdexterous surgical system 100. In some embodiments, more than one (e.g., a plurality, several) tracking technologies are used in conjunction. The redundant tracking technologies can account for occlusions and detect malfunctions. The redundant tracking technologies can increase resolution or bandwidth.

In some embodiments, the input devices 500 are sterile or capable of being sterilized. The operator 1 needs to maintain his hands in a sterile environment during the course of the procedure. During surgery, the operator 1 may manipulate one or more manual tools 350 and one or more input devices 500. The input devices 500 can be used in conjunction with touching the patient. For instance, the operator 1 can control the input devices 500 and touch the patient 2 simultaneously (e.g., with their hand or a manual tool). The input devices 500 must be sterile or capable of being sterilized to maintain the sterile operating environment.

In some embodiments, the input devices 500 can include one or more features that interact with the control system 400. For instance, the input devices 500 can control a camera 304 (see FIG. 35), such as a camera placed in the workspace inside the patient or in the free space above a patient. The camera 304 can be considered a hyperdexterous surgical tool 300 and controlled by an input device 500. The input devices 500 can alter the images shown on the display 600, 702. Images may be inverted, rotated, and left-right flipped on the display 600, 702 to reflect the viewpoint of the tracked objects, such as the operator 1, or controllable objects such as hyperdexterous surgical arms 200 and/or hyperdexterous surgical tools 300, as described below. In some embodiments, the input devices 500 include a button and/or a slider. The button and/or slider can be actuated by the operator 1 to change the camera 304 pan/tilt and/or zoom. In some embodiments, the operator 1 depresses a button on the input device 500 and uses motions of another part of the operator's body to change the camera parameter. For example, the operator 1 can depress the button and use motions of his eyes to change a camera parameter. In some embodiments, the operator 1 moves the slider (e.g., with a finger) to change the zoom of the camera 304. In some embodiments, the input devices 500 can accept information from the control system 400, described below. The control system can send information to the input devices 500, such as instructions to produce tactile feedback for the operator 1. The tactile feedback can be sent via a wireless or a wired connection. The input device 500 can integrate a sensor which imitates the tactile feedback of using a tool. The input device 500 can imitate the tactile feedback of the hyperdexterous surgical tool 300. The input device 500 can imitate the tactile feedback of the manual tool 350. The hyperdexterous surgical system 100 can link the actual tactile feedback of the manual tool 350 with an imitation tactile feedback conveyed by the input device 500. In some embodiments, the input device 500 can be docked at an interface (e.g., platform 602) which can provide tactile feedback.

Control System

The hyperdexterous surgical system 100 can include a control system 400 that translates user inputs (e.g., via input devices 500, display 600) to outputs (e.g., motion of control points, images). The control system 400 can pair certain user inputs to certain controllable objects. When executing the movements of the various hyperdexterous surgical tools 300, the control system 400 may maintain one or more constraints. The control system 400 can lock one or more hyperdexterous surgical tools 300 to a single tool (e.g., a hyperdexterous surgical tool 300 or a manual tool 350). Advantageously, the control system 400 allows the hyperdexterous surgical system 100 to enable the flexibility provided to the operator (e.g., surgeon) for performing surgical procedures. For example, as discussed in more detail below, the control system 400 allows the surgeon to control the hyperdexterous surgical tools 300 using various frames of reference (e.g., immersive camera mounted frame of reference, world-grounded frame of reference), and the ability to move between various frames of reference, which advantageously allows the surgeon to move seamlessly between operating the hyperdexterous surgical tools 300 with a camera-mounted frame of reference to perform a surgical task, to a world-grounded frame of reference that allows the surgeon to reposition him or herself in another position while retaining awareness of the position of the hyperdexterous surgical tools 300 relative to himself, and then moving back to a camera-mounted frame of reference to continue with a surgical task to begin a different surgical task. Additionally, the control system 400 advantageously allows the surgeon to switch control of hyperdexterous surgical tools 300 (e.g., between right and left), to allow repositioning of the surgeon to an optimal position, and to rotate the camera view accordingly. Further, the control system 400 can advantageously allow one or more hyperdexterous surgical tools 300 to be controlled so that it moves in synchrony with another tool (e.g., with another hyperdexterous surgical tool 300, or with a manual tool 350), which can allow the surgeon to virtually tether the tools and move them at the same time, such as when moving the tools to another surgical site.

FIG. 34 illustrates an embodiment of the control system 400. The control system 400 architecture may be thought of as containing three sections; a section 408 which receives inputs, a section 410 responsible for sending output, and a section 412 that computes the outputs based on various data including the inputs. The operator 1 can provide an input via the input device 500. The inputs can be provided by a wireless or wired input device 500. The location of the operator 1 can be an input (e.g., as tracked by a tracking device that communicates with the control system 400). Additional components can provide inputs including the display 600 and the clutch 112.

The control system 400 may receive inputs from location and orientation sensors of the hyperdexterous surgical arm 200, the hyperdexterous surgical tool 300 and/or the manual tool 350. The control system 400 computes outputs based in part on the various inputs. The outputs may manipulate the one or more hyperdexterous surgical tools 300 and/or the one or more hyperdexterous surgical arms 200. The outputs may be tactile signals sent to the input device 500 to be felt by the surgeon. The output may be images shown on the one or more displays 600, 702.

FIG. 35 shows an embodiment of the control system 400 with the computer 402. The control system 400 can be coupled with several controllable objects, such as one or more hyperdexterous surgical arms 200 and one or more hyperdexterous surgical tools 300.

The control system 400 can be coupled with several input devices 500. The arrows indicate the flow of information between the control system 400 and the input devices 500. The control system can send information to the input devices 500, for instance tactile feedback as shown by the arrow. The dotted arrow is meant to indicate a wireless communication. The double arrows indicate an input to the control system and an output from the control system. The tactile feedback can be sent via a wireless or a wired connection. The input devices 500 can be used to control the movement of one or more hyperdexterous surgical arms 200 and/or one or more hyperdexterous surgical tools 300.

Other than input devices 500, the control system maybe coupled to several output devices as well. The control system 400 can be coupled with several devices, such as the display 600 and the display 702. The display 600 can also be an input. The display 600 provides information to the operator 1 and accepts information from the operator 1. The display 600 can be a touch screen monitor 604. Other types of displays 600 may also be used such as an iPad or other mobile electronic device. In some embodiments, the display 600 is sterile or capable of being sterilized. The display 600 can be used in conjunction with manual tools 350. The display 600 can be used in conjunction with touching the patient. The operator 1 can control the display 600 and manual tools 350 simultaneously. The operator can control the display 600 and touch the patient 2 simultaneously.

The control system 400 can be coupled with several controllable objects, such as hyperdexterous surgical arms 200 and/or hyperdexterous surgical tools 300. The control system 400 can be coupled with several input devices 500. The double headed arrow indicates the flow of information between the computer 402 and the input devices 500. The clutch 112 can provide an input to the computer.

The manual tool 350 (e.g., a sensor 352 affixed to a manual tool 350) can provide an input to the computer. As described earlier manual tools 350 can also be used with the hyperdexterous surgical system 100. The sensors 352 on the manual tool 350 may provide an input to the computer 402. The manual tool 350 can be tracked by the sensors 352, such as position sensors. The sensors 352 can be affixed, for example, by a collar or a sleeve that fits over the manual tool 350. The collar or sleeve can include various sensors 352, which may be wireless or wired. In some embodiments, the sensors 352 may be integrally formed with the manual tool 350. The tracking of manual tools 350 is useful in many situations, such as when the manual tool 350 is not within the range of sight of the camera 304.

The display 600 may show the associations (e.g., pairings) between the input devices 500 and the controlled objects, such as the one or more hyperdexterous surgical arms 200 and/or the one or more hyperdexterous surgical tools 300. As a non-limiting example, the display 600 may show icons for the input devices 500 and the controlled objects, such as the one or more hyperdexterous surgical arms 200 and/or the one or more hyperdexterous surgical tools 300.

Figure 36:
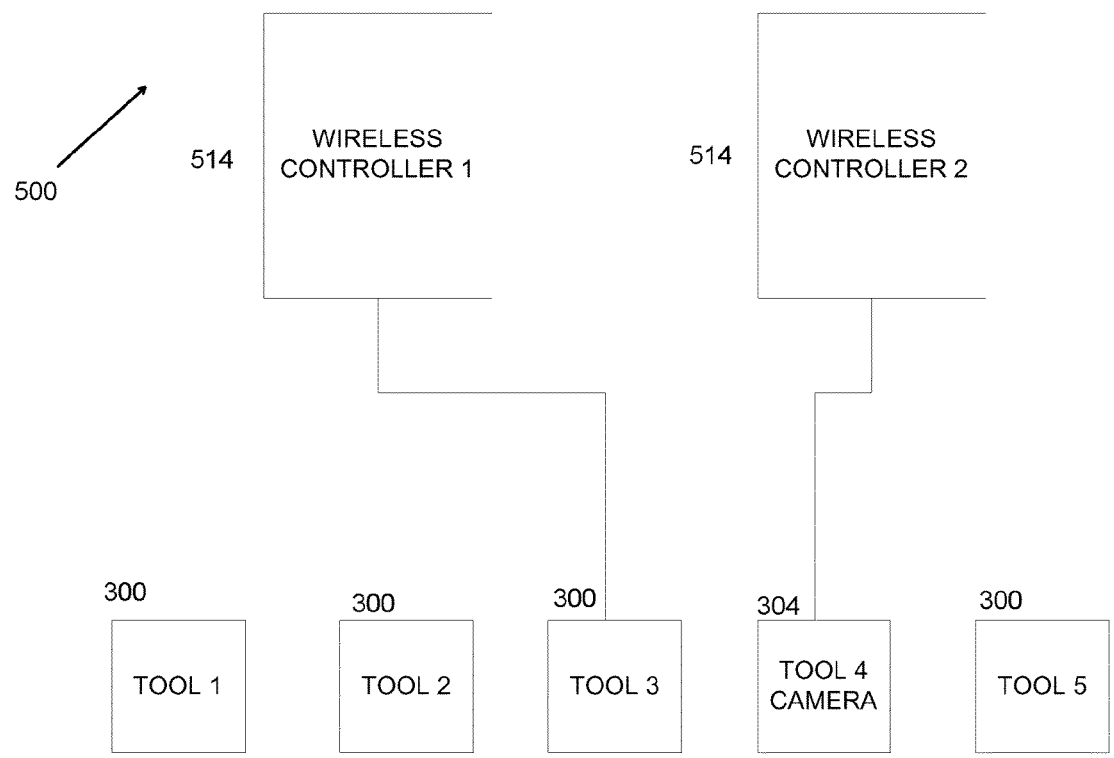
FIG. 36 schematically illustrates an embodiment of a screenshot of a display.

FIG. 36 shows one embodiment of a screen shot of a display 600. In this example, the operator 1 selects an input device 500. As shown in FIG. 36, two input devices 500 are available to be selected by the operator 1. These input devices 500 are two wireless controllers 514, but other input devices 500 can be depicted on the display 600 (e.g., wired controllers). As shown in FIG. 36, five controllable objects are available to be selected by the operator. These controllable objects are five hyperdexterous surgical tools 300 including one camera 304. The camera 304 can be considered a hyperdexterous surgical tool 300. Other controllable objects can be depicted on the display 600. The operator 1 can select one of the input device icons. The operator 1 can select one of the controllable object icons. In some embodiments, the operator 1 selects an input device icon and then selects a controllable object icon in sequence, which will cause the selected input device to be paired with and control the selected controllable object. In another embodiment, the operator 1 may run a finger between the input device icon and the controllable object icon on a touch screen 604 to pair them together. In yet another embodiment, the operator 1 may use a mouse or pointer to select two icons. The display 600 may indicate the association (e.g., pairing) between the input device 500 and the controlled object for example by indicating a line between icons.

Figure 37:
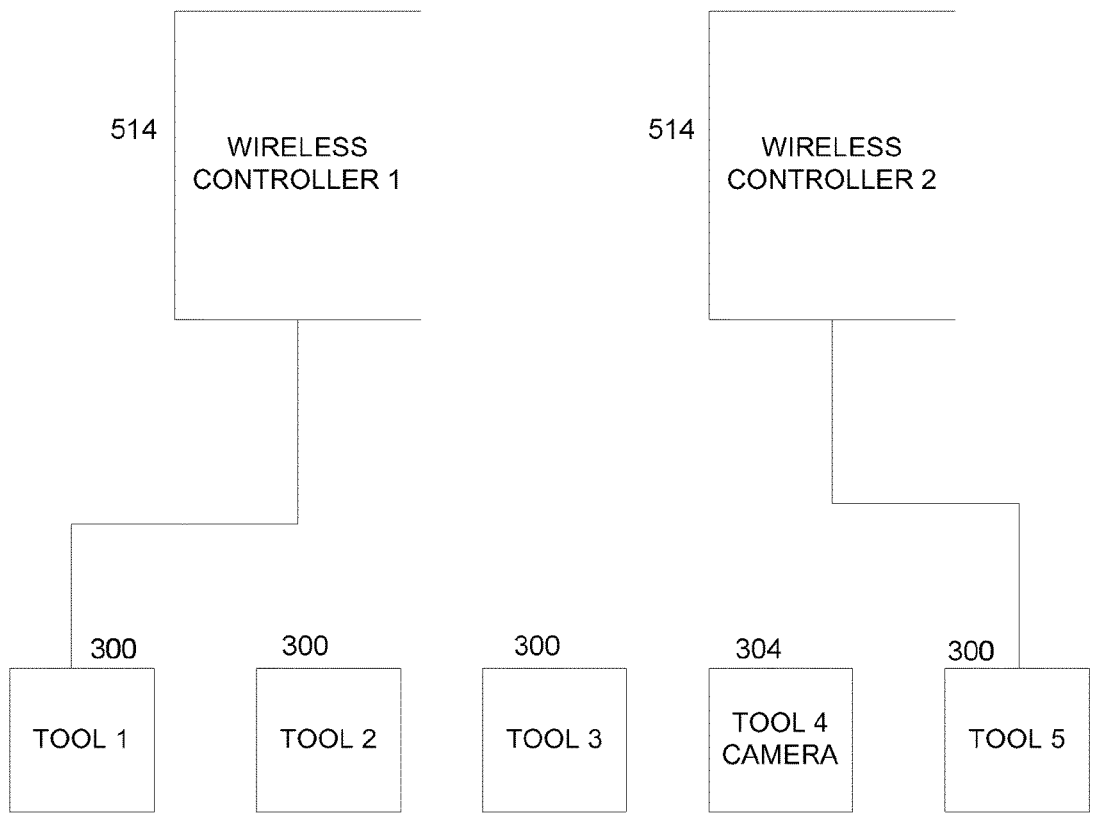
FIG. 37 schematically illustrates a screenshot of a display.

For example, one controller 514, labeled Wireless Controller 1, may control one controllable object, labeled Tool 3. One controller 514, labeled Wireless Controller 2, may control one controllable object, labeled Tool 4. Other configurations between the input devices and the controllable objects are possible by following the selection sequence described above. FIG. 37 is a screen shot of the display shown in FIG. 36. For example, one controller 514, labeled Wireless Controller 1, may control one controllable object, labeled Tool 1. One controller 514, labeled Wireless Controller 2, may control one controllable object, labeled Tool 5.

The control system 400 may associate the coordinate system of the input device 500 and coordinate systems of the controlled objects, such as the one or more hyperdexterous surgical arms 200 and/or the one or more hyperdexterous surgical tools 300. The display 600 may show the associations (e.g., pairings) between the input devices 500 and the controlled objects. The input device 500 and the controlled object may move in the same coordinate system. The input device 500 may move in a rectilinear coordinate system, which may move the controlled object also in a rectilinear coordinate system. For instance, a movement of an input device 500 a distance in the positive x-axis direction may move a hyperdexterous surgical tool 300 a different distance or the same distance in the positive x-axis direction. Both the controlled object and the input device move in a rectilinear coordinate system.

The input device 500 may move about an imaginary center, which may move the controlled object about a virtual grip 512. For instance, if the hyperdexterous surgical tool 300 moves in circular arcs about a fulcrum, moving the input device 500 in a circular motion about an imaginary center may be more natural. This circular motion may be more natural than a rectilinear motion of the input device 500. Both the controlled object and the input device move in a polar coordinate system.

The input device 500 and the controlled object may move in different coordinate systems. The input device 500 may be moved in a rectilinear coordinate system which may move the controlled object in a polar coordinate system. For some types of motions, it may be easier to calculate and/or display the motion of the controlled object in alternative coordinate systems. Combinations are possible.

The operator may establish certain constraints for the hyperdexterous surgical system 100. The control system 400 can be arranged such that the constraints are measured quantities such as position or derived parameters such as distance, velocity, force, and tension. The control system can be arranged such that the constraints can be different for each controlled object.

When executing the movements of the various hyperdexterous surgical tools 300, the control system 400 may maintain one or more constraints. Constraints may be a physical or a derived parameter such as distance, velocity, force, tension, and/or radius. The control system 400 may apply one or more constraints to the motion of one or more hyperdexterous surgical tools 300. Constraints may be different for each controlled object. For example, the hyperdexterous surgical tools 300 locked to a single tool may be subjected to different constrains. Each hyperdexterous surgical tool 300 may have an independent constraint.

In some embodiments, two hyperdexterous surgical tools 300 can be constrained to move together. The operator 1, such as the surgeon, can lock one or more of the hyperdexterous surgical tools 300 to a single tool. All of the locked hyperdexterous surgical tools 300 would follow the single tool. In other words, all of the locked hyperdexterous surgical tools 300 would move substantially in unison (e.g. at the same time) as the single tool is controlled by the operator 1 and moved from place to place. Conceptually, this lock step motion can be thought of as a virtual tether holding the relative positions of the hyperdexterous surgical tools 300 constant and moving the set of hyperdexterous surgical tools 300 in unison.

The concept of locking one or more hyperdexterous surgical tools 300 to a single tool applies equally to whether the single tool is a hyperdexterous surgical tool 300 or a manual tool 350. For one or more hyperdexterous surgical tools 300 to follow the manual tool 350, the manual tool 350 can be tracked in space for translation and rotation. This type of configuration where one or more hyperdexterous surgical tools 300 follows the manual tool 350 may be useful when the operator 1, such as a surgeon, wants to move large distances within the work space. The concept of locking may also advantageously avoid collisions between the hyperdexterous surgical tools 300, manual tools 350 and/or the anatomy of the patient 2.

It may not be necessary to lock all the hyperdexterous surgical tools 300 to a single tool. In some embodiments, the operator 1 can choose to lock some (but not all) of the hyperdexterous surgical tools 300 to a single tool and leave some hyperdexterous surgical tools 300 unlocked, and in place. For example the camera 304 may be in a good position but the other hyperdexterous surgical tools 300 such as graspers may need to be moved to a different location. The other hyperdexterous surgical tools 300 such as graspers can be locked, so as to follow the single hyperdexterous surgical tool 300, but the camera 304 can remain in place. The need for moving all or some of the hyperdexterous surgical tools 300 in unison may arise if the operator 1 needs to operate on another section of the body distant from the current section undergoing surgical intervention.

Figure 40:
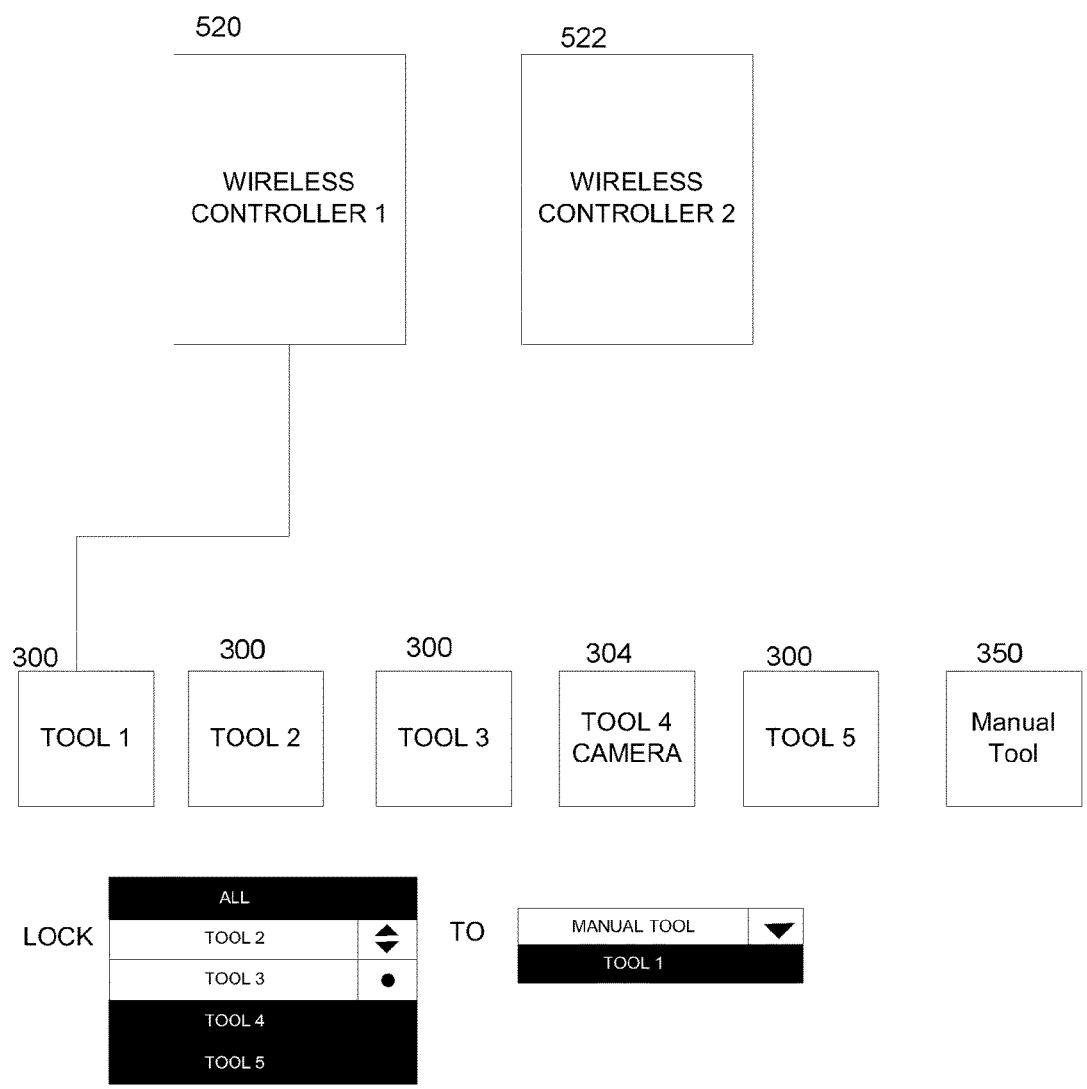
FIG. 40 schematically illustrates a screenshot of a display.

In some embodiments, the one or more hyperdexterous surgical tools may be locked to a single hyperdexterous surgical tool or a single manual tool through the use of the display 600. FIG. 40 shows a screen shot that may be displayed on the display 600. Other screen layouts are possible. The display 600 enables the operator 1 such as a surgeon to lock one or more of the hyperdexterous surgical tools 300. The top portion of the screen shot shows the input devices 500 and the controllable objects, such as hyperdexterous surgical tools 300. FIG. 40 shows five hyperdexterous surgical tools 300 including camera 304. The manual tool 350 is also shown. FIG. 40 shows two input devices 500, a wireless controller 520, and a wireless controller 522. Depending on the tools, including all hyperdexterous surgical tools 300 and all manual tools 350 in communication with the control system 400, the display 600 displays the appropriate icons. The wireless controller 520 is connected to the controllable object, Tool 1. The wireless controller 522 is not connected to a controllable object.

The bottom portion of the screen shot of FIG. 40 shows locking options. Any controllable object controlled by an input device may not appear on the list. For instance, since Tool 1 is being controlled by the wireless controller 520, the display 600 does not display Tool 1 in the set of tools that can be locked. The selected controllable objects, such as one or more hyperdexterous surgical tools 300, can be selected by the user to be locked. For instance, Tools 2 and 3 are selected to be locked, while Tools 4 and 5 are unselected. The display 600 can highlight the selected entries, as shown in FIG. 40. The hyperdexterous surgical tools 300 that have been selected to be locked are shown in white whereas the others are shown in black. On the bottom portion of the screen shot, the display 600 displays the options for the single tool. The single tool is followed by the one or more locked hyperdexterous surgical tools 300. For instance, the manual tool 350 is selected to be the single tool, while Tool 1 controlled by the wireless controller 522 is unselected. The display 600 can highlight the selected entries, as shown in FIG. 40. In this example, Tool 2 and Tool 3 are locked to the manual tool 350, but other configurations are possible.

In some embodiments, the movement of the single tool may be controlled by smaller hand gestures rather than larger movements associated with the set of tools. For instance, the single tool may be Tool 1, controlled by the wireless controller 522. The wireless controller 522 may be worn by the operator 1, as described above. For instance, one or more fingers of the operator's hand may have sensors affixed or otherwise attached. A specific movement of the hand or of the fingers may move the single tool. The one or more hyperdexterous surgical tools 300 that are locked will move according to the movement of the single tool, as described above.

The operator 1 such as a surgeon may engage or disengage the selected hyperdexterous surgical tools 300 from actively following the single tool. The operator can utilize the clutch 112, such as a foot pedal. For example, when the clutch 112 is depressed, the selected hyperdexterous surgical tools 300 will follow the single tool. When the clutch 112 is released, the selected hyperdexterous surgical tools 300 will stop moving and remain in place. This feature may advantageously allow the operator to reposition his or her arms much like computer users reposition a computer mouse by lifting the mouse and placing it in a more comfortable position.

The following three constraints provide examples of additional constraints that may be imposed. Constant tension of the gripped object is maintained. The ratio of motion of the hand to the motion of the hyperdexterous surgical tools is 1:10, meaning that when the hand moves 10 cm, the tools move 1 cm. The camera tool 304 is rotated about a fulcrum instead of translated linearly.

The control system 400 can apply a constraint to a hyperdexterous surgical tool 300. For instance, the control system 400 can adjust the position of one hyperdexterous surgical tool 300 in order to apply a constant tension to the tissue held by the set of hyperdexterous surgical tools 300. These constraints provide useful ways to control the hyperdexterous surgical tools 300. Constraints may be applied relative to the manual tool 350 as well. Other constraints can be applied in addition to, or in place of, those described above. The control system 400 can apply a constraint between the hyperdexterous surgical tool 300 and the camera 304. The control system 400 can establish position, speed or force constraints between one or more hyperdexterous surgical tool 300 and the camera 304.

Figures 38A, 38B:
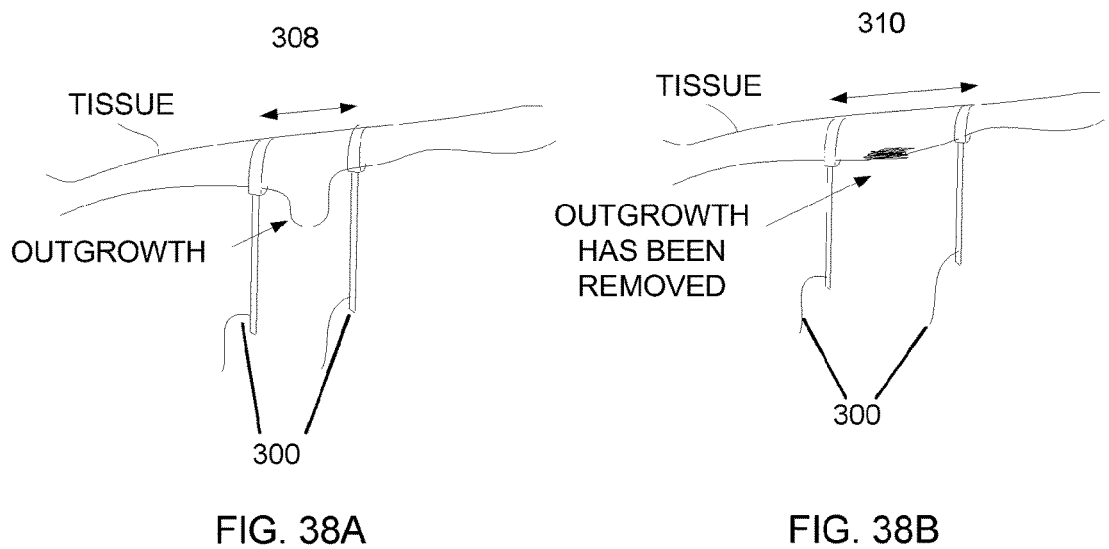
FIGS. 38A-38B schematically illustrate a method of holding the tissue in constant tension.

In FIGS. 38A-B, two hyperdexterous surgical tools 300, such as grippers, are shown on either side of a tissue outgrowth. The hyperdexterous surgical tools 300 are at a certain distance 308 as shown in FIG. 38. When the outgrowth is removed, the hyperdexterous surgical tools 300 may need to be repositioned. For instance, the tissue may need to be held at a higher tension since the outgrowth is no longer pulling the tissue. The hyperdexterous surgical tools 300 are now at a distance 310, which may be greater than distance 308. The control system 400 may control the hyperdexterous surgical tools 300 so that certain parameters of the surgery may be maintained. For instance, in this example, the control system 400 may control the hyperdexterous surgical tools 300 so that the tissue is in constant tension.

If multiple tools are used in the hyperdexterous surgical system 100, then any set of two or more tools may be controlled as a rigid body. For example, the set of hyperdexterous surgical tools 300 may be controlled such that the tissue is manipulated as a rigid body and is tracked by the camera 304. The rigid body effect may be achieved when the control system 400 calculates and applies appropriate tension through the hyperdexterous surgical tools 300 to the tissue. The calculations may be in real time and be dynamic. This may assist in maintaining the rigid body effect, for instance if the section of tissue is in motion due to controlling motions of the surgeon.

Frame of Reference, Visual Cues

The control system 400 advantageously allows the operator 1 to control the hyperdexterous surgical tools 300 and/or the manual tools 350 naturally. There are at least two interconnected pieces that allow natural and effective control: visual cues and moving in frames of reference that are natural to the human body and easily processed by the human brain. The brain can easily understand frames of references associated with a person's wrist. The control system 400 advantageously provides the operator 1 with visual cues related to the hyperdexterous surgical tools 300 and/or manual tools 350, which enable the operator to better understand the frames of reference associated with the movement of the hyperdexterous surgical tools 300 and/or manual tools 350.

Frame of References

As discussed above, the human brain can easily understand movement if the frames of references are coupled to the wrist. With reference to FIGS. 41A-41D, the brain understands that in order to reach the objects, the wrists must be moved toward the object. The brain understands which way to move the wrist based on the orientation of the wrist.

Figure 41A:
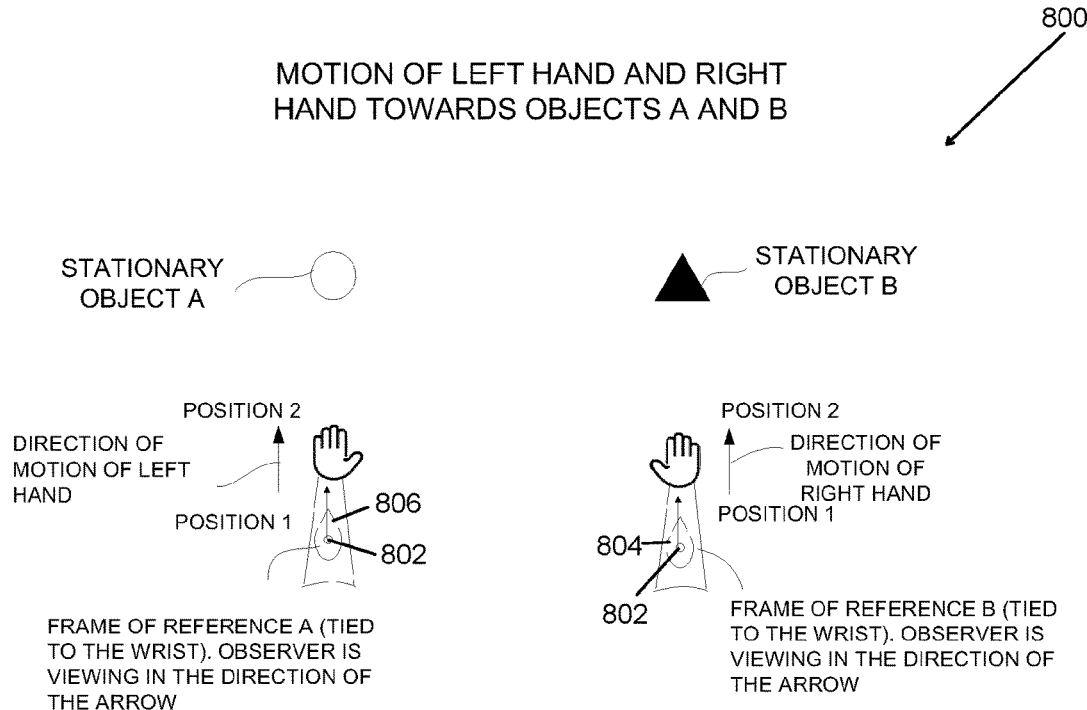
FIG. 41A schematically illustrates two frames of reference that are oriented the same way.
Figure 41B:
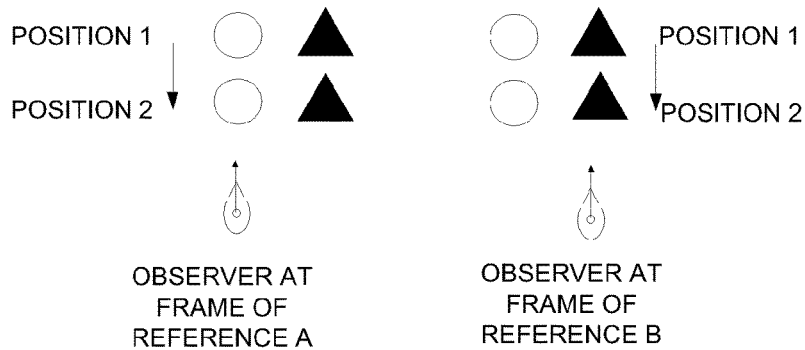
FIG. 41B schematically illustrates the motion as perceived by the observers placed at the locations specified in FIG. 41A.
Figure 41C:
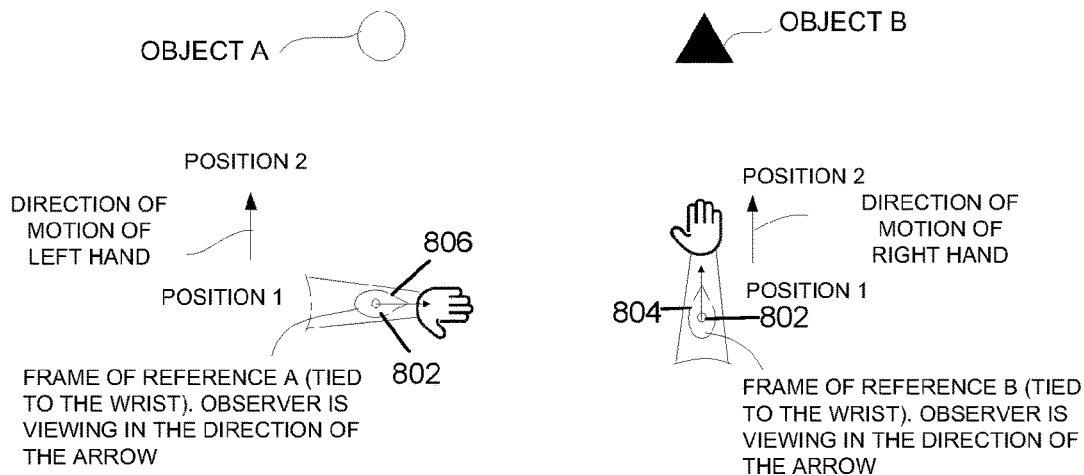
FIG. 41C schematically illustrates two frames of reference that are not oriented the same way.

In FIGS. 41A and 41C, a left hand and a right hand of an operator 1 such as a surgeon is shown. The direction of motion of the hands is shown on each figure. Each hand moves toward an object. The left hand moves from Position 1 to Position 2, toward Object A. The right hand moves from Position 1 to Position 2, toward Object B. A frame of reference is placed on each wrist. The orientation of the frame of reference is indicated by the pointed end of the icon representing the frame of reference. The imaginary observer 802 would be standing on the circle in the middle of the frame of reference icon. In other words, the imaginary observer 802 would be looking in the direction of the pointed end of the icon, in the direction of the arrow.

Figure 41D:
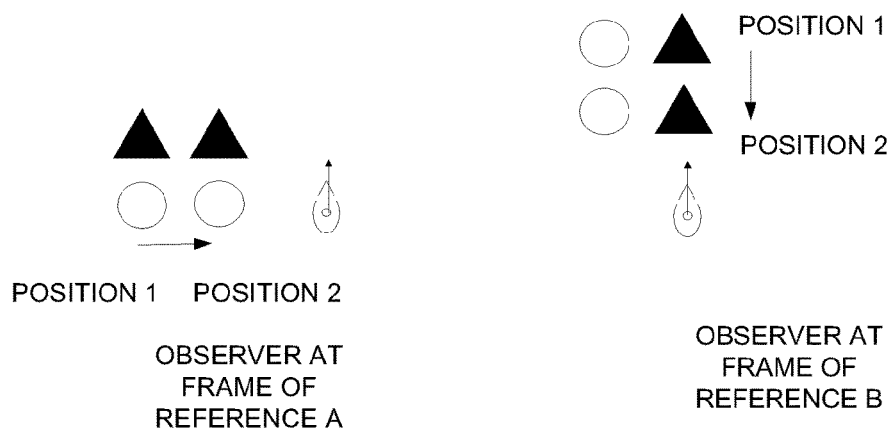
FIG. 41D schematically illustrates the motion as perceived by the observers placed at the locations specified in FIG. 41C.

FIGS. 41A and 41C indicate the motion and the frame of reference for each hand. FIGS. 41B and 41D indicate how the motion is perceived by the imaginary observer 802 placed as explained above. The left hand moves from Position 1 to Position 2, toward Object A. The right hand moves from Position 1 to Position 2, toward Object B. A frame of reference is placed on each wrist.

In FIG. 41A, both hands are oriented the same way, so both hands must move forward to reach the objects. In FIG. 41A, the frames of reference for each imaginary observer 802 (one on each wrist) are oriented the same way. In other words, the frames of references are aligned.

FIG. 41B illustrates how the objects will appear to these imaginary observers 802. Both imaginary observers 802 see substantially the same images. At Position 1, the Objects A and B, the circle and the triangle, are a distance away from the imaginary observers 802. At Position 2, the Objects A and B, the circle and the triangle, are closer to the imaginary observers 802. The imaginary observer 802 on the right wrist is closer to the Object B, the triangle. The imaginary observer 802 on the left wrist is closer to the Object A, the circle.

In FIG. 41C, the left hand is perpendicular to the right hand. The right hand must move forward to reach the objects. The left hand must move toward the left to reach the objects. In FIG. 41C, the frames of reference for each imaginary observer 802 (one on each wrist) are not oriented the same way. The frame of reference for the left hand is rotated 90° with respect to the frame of reference on the right hand. Although the FIG. 41C shows frames of reference that are rotated 90° to each other, any other orientation in a three-dimensional space is possible.

FIG. 41D illustrates how the objects will appear to these imaginary observers 802. Both imaginary observers 802 see a different image. To the imaginary observer on the right wrist, the Objects A and B are in front of the viewer. To the imaginary observer on the left wrist, the Objects A and B are to the left of the viewer. At Position 1, the Objects A and B, the circle and the triangle, are a distance away from the imaginary observers 802. At Position 2, the Objects A and B, the circle and the triangle, are closer to the imaginary observers 802.

In FIGS. 41A-41D, the operator is provided with visual cues. The operator can see the Objects A and B. The operator 1 can see his hands. When the operator 1 is manipulating the hyperdexterous surgical tools 300 and/or manual tools 350 within the patient's body, the operator 1 could benefit from receiving visual cues related to the hyperdexterous surgical tools 300 and/or manual tools 350. The visual cues can enable the operator to better understand the frames of reference associated with the movement of the hyperdexterous surgical tools 300. As mentioned herein, hyperdexterous surgical system 100 enables the operator 1 to control hyperdexterous surgical tools 300 and manual tools 350 simultaneously. For example, as a non-limiting example, the operator 1 can control a hyperdexterous surgical tool 300 such as a gripper with the left hand and the manual tool 350 such as a stapler with the right hand. The control system 400 can allow the operator 1 to manipulate each tool in an independent frame of reference 800. The control system 400 can include a control algorithm to translate the motions of the operator (e.g., motions controlling the input device 500) into movements in the correct frame of reference.

Figure 42A:
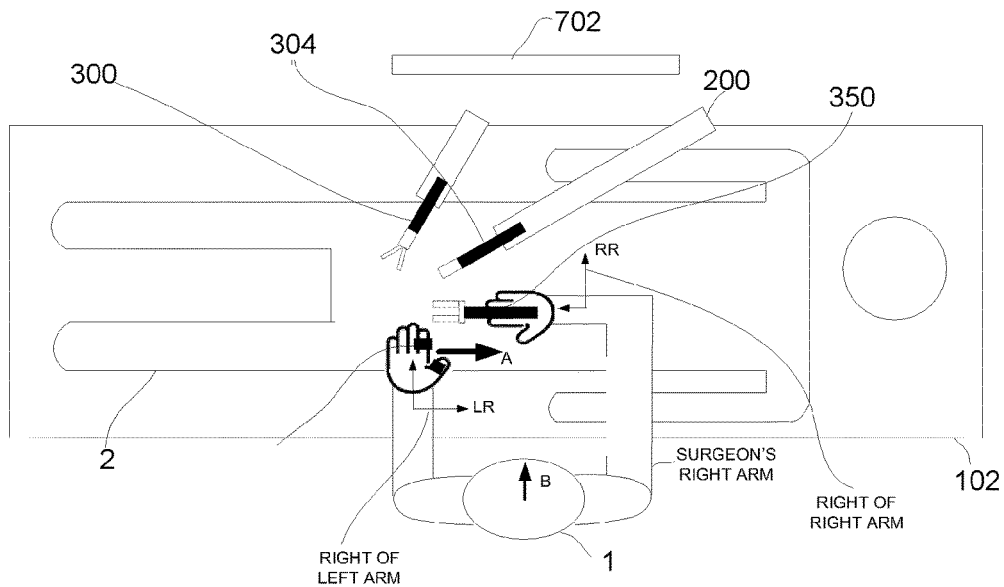
FIG. 42A schematically illustrates an operator controlling a hyperdexterous surgical tool and a manual tool.

Referring now to FIG. 42A, the operator 1 is manipulating the hyperdexterous surgical tool 300 and the manual tool 350 within the body of the patient. FIG. 42A shows the operator 1 controlling the hyperdexterous surgical tool 300 with his or her left hand and the manual tool 350 with his or her right hand. Both the hyperdexterous surgical tools 300 and/or manual tools 350 are within the body and obstructed from the operator's view.

The manual tool 350 may dictate the position of the operator 1 relative to the patient 2. The design of the manual tool 350 will dictate the position of the hand controlling the manual tool 350. The operator 1 may want to control the hyperdexterous surgical tool 300 from substantially the same position with his or her other hand.

The frame of reference associated with the operator's left hand controlling the hyperdexterous surgical tool 300 may be rotated with respect to the frame of reference associated with the operator's right hand controlling the manual tool. As shown in FIG. 42A, the frame of reference for the right hand is rotated 90° with respect to the frame of reference for the left hand (opposite configuration of that shown in FIG. 41A).

The frames of reference are placed on each wrist. Two orthogonal pairs of arrows are shown on each wrist to illustrate how the objects will appear to the imaginary observers 802. On the right wrist, the letters "RR" indicate that this direction is the right side of the operator's right wrist, or what appears to be the right side to the imaginary observer 802. The letters "LR" indicate the right side of the operator's left wrist, or what appears to be the right side to the imaginary observer 802. Both imaginary observers 802 see a different image. The camera 304 (with the lens inside the body) sees both the manual tool 350 and the hyperdexterous surgical tool 300 that are inside the body.

To manipulate the manual tool 350, the operator 1 may move the right hand and may use the right wrist in the frame of reference as shown. The right hand is illustrated at a 90° angle to the right arm, and at a 90° angle to the left hand. The operator can manipulated each tool in an independent frame of reference. The manual tool 350 can be manipulated with respect to a frame of reference associated with the right wrist and the hyperdexterous surgical tool 300 can be manipulated with respect to the left wrist.

FIG. 42A shows an input device 500 affixed to the left hand. The operator 1 can use the input device 500 to control a hyperdexterous surgical tool 300 such as the grasper. The camera 304 (with the lens inside the body) will show the motion of the grasper and/or end effector of the grasper on the display 702. In the illustrated embodiment, the operator 1 is standing beside the patient 2 facing the patient 2 and has his or her head facing the display 702 (e.g., facing straight ahead along Arrow B). The control system 400 can show on the display a natural perspective of the surgery. For instance, a rightward motion of the left hand may be shown as a rightward motion of the hyperdexterous surgical tool 300 as presented on the display 702. The control system 400 can use the position of the input devices 500, the position of the camera 304, the position of the operator 1, and/or the position of the hyperdexterous surgical tool 300 to orient the image on the display 600, 702. The control system 400 can calculate the motion of the end effector of the grasper. The control system 400 can orient the image of the camera 304 on the display 600, 702. For instance, the control system 400 can orient the image such that a rightward motion of the left wrist is seen as a rightward motion of the hyperdexterous surgical tool 300.

The control of the manual tool 350 with the operator's right hand may be in a frame of reference associated with the operator's right wrist. The control of the hyperdexterous surgical tool 300 with the operator's left hand may be in a frame of reference association with the operator's left wrist. This frame of reference of the left wrist may be an independent frame of reference from the frame of reference of the right wrist. Regardless the angle of the operator's right wrist and right hand, the human brain can recognize right, left, up and down relative to the right wrist and hand.

The two frames of reference may be completely independent, partially aligned, or the completely aligned. In some embodiments, the hyperdexterous surgical tool 300 may move in a frame of reference aligned with the surgical target. Both the manual tool 350 and the hyperdexterous surgical tool 300 may move with respect to the surgical target to allow consistent movement of the manual tool 350 and the hyperdexterous surgical tool 300. It is to be noted that in all these examples, the frame of reference of the manual tool 350 may or may not be aligned to the frame of reference of the hyperdexterous surgical tool 300. Each situation will have its unique advantages in how the hyperdexterous surgical tools 300 and the manual tools 350 are controlled.

When controlling multiple tools in independent frames of reference, different combination of tools may be utilized. The operator may control the hyperdexterous surgical tool 300 and the manual tool 350, or two or more hyperdexterous surgical tools 300, or two or more manual tools 350. The operator 1 may manipulate one or more hyperdexterous surgical tools 300 with each hand, as opposed to controlling the manual tool 350 and the hyperdexterous surgical tool 300 as described above.

The human brain is also capable of readily comprehending and coordinating the hyperdexterous surgical tool 300 with the manual tool 350, in order to use the two tools together. The brain is able to coordinate movement despite the different frames of reference. In FIG. 42A, the operator 1 is holding the manual tool 350, such as a stapler, with the right hand and the input device 500 with the left hand.

Visual Cues

The human brain is capable of determining how to move the manual tool 350 and the hyperdexterous surgical tool 300 with adequate information. This information should enable the user to naturally understand the movement of the hyperdexterous surgical tool 300. The control system 400 advantageously provides such visual cues to the operator 1 (e.g., surgeon), for example, by orienting images presented to the operator or varying the information provided in said images (e.g., illustrating at least a portion of the body of the patient 2 to help the operator 1 understand the orientation of the tools) to facilitate natural control of the hyperdexterous surgical tools 300. In this manner, the control system 400 can enable natural control of the hyperdexterous surgical tool 300 from any location of the operator 1.

Figure 42B:
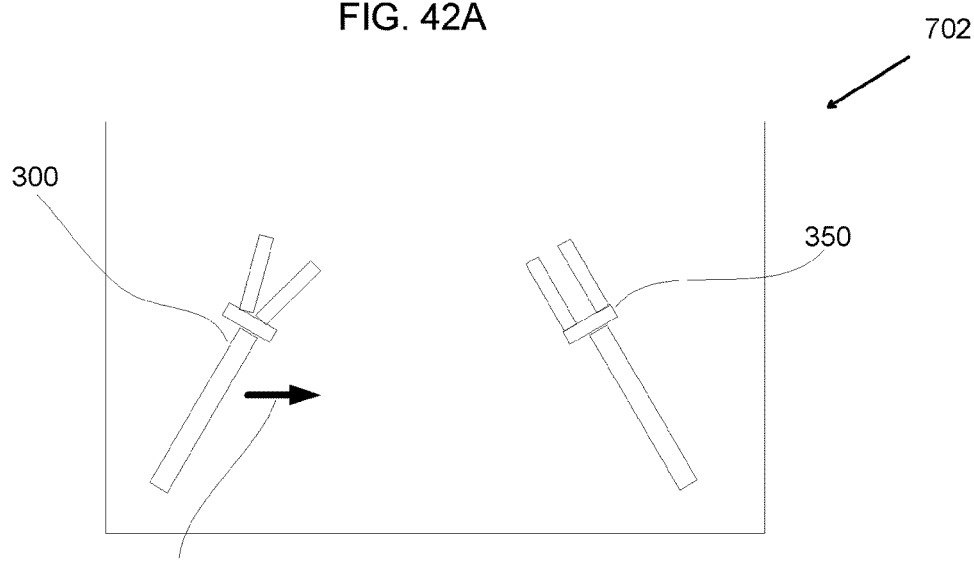
FIG. 42B schematically illustrates a screen shot of a display.

FIG. 42B shows the view of the display 702. The display 702 can provide images captured by camera 304, shown in FIG. 42A. A rightward motion of the left hand along the direction of Arrow A is shown in FIG. 42A. The relative orientation of the tools can augment the operator's 1 understanding of the workspace. The display 702 can represent the manual tools 350 and the hyperdexterous surgical tools 300 in same environment. However, an image other than the camera image, such as an image of the orientation of the patient relative to the tools 300, 350, may augment the operator's 1 understanding of the motion of the hyperdexterous surgical tool 300 and/or manual tool within the body of the patient.

The control system 400 may orient the camera image on the display 600, 702. The displays 600, 702 can show both the manual tool 350 and the hyperdexterous surgical tool 300. The control system 400 may orient the camera image relative to the frame of reference of the operator's wrist. The control system 400 may determine the direction of the motion relative to the operator's wrist and present the image of the movement in the same direction. For example, in FIG. 42A, the operator 1 moves his left hand along arrow A. The operator moves his left hand toward the right.

As shown in FIG. 42B, the control system 400 can orient the image of the camera 304 such that the image presented on the display 702 matches the direction of the movement. When presented on the display 702, the motion of the hyperdexterous surgical tool 300 is along the original direction, rightward. From the point of view of the camera, this motion may be leftward or angled. The control system 400 can display the motion of the of the hyperdexterous surgical tool 300 such that the operator 1 is able to understand the motion naturally. By looking at the display 702, the operator 1 can coordinate the rightward movement of the input device 500 with the rightward motion of the hyperdexterous surgical tool 300.

The orientation of the image on the display 600, 702 may assist with the use of hyperdexterous tools or manual tools that rotate about the fulcrum. The motion of the distal end of the manual tool 350 (the section furthest away from the hand) may move in the opposite direction relative to the hand. In other words, if the right hand is manipulating the stapler about a fulcrum, then a rightward motion of the handle of the stapler will translate to a leftward motion of the distal end of the stapler. By providing visual cues, the hyperdexterous surgical system 100 may enable natural use of hyperdexterous tools or manual tools that rotate about the fulcrum.

The control system 400 can enable natural control of the hyperdexterous surgical tool 300 from any location of the operator 1 via the images presented to the operator 1 as discussed herein. During the course of the procedure, the operator 1 may need to move about the operating area. The manual tool 350 may dictate the location of the operator 1. The control system 400 can present images based on the point of view of the operator 1, regardless of the operator's location.

The position of operator 1 may be tracked. The image can be updated to be consistent with the point of view of the operator 1. The image can be calculated based on the location of the operator 1, particularly in the zoomed out view. Tracking of the operator 1 may be accomplished by using one of various technologies such as but not limited to affixing sensors to the operator 1, or by using an optical localization system. The hyperdexterous surgical system can have a global tracker that tracks the operator 1.

The location of the operator 1 can be an input into the control system 400. The control system 400 computes and presents images from the point view of the operator 1. In order words, the display 600, 702 can show what anatomy or tools the operator 1 would be seeing from that location. As the operator 1 moves around, the image presented on the display 600, 702 would be based on the position of the operator 1. The computation and presentation of the images based on the operator's location may augment the operator's understanding of the anatomy and allow the operator to more easily interact with both manual tools 350 and the hyperdexterous surgical tools 300.

The coordinate conversion can be associated with the proximal end (e.g., laparoscopic tools) or the distal end (e.g., end effectors). The control system 400 may present images of the hyperdexterous surgical tools 300 and the manual tools 350 in independent coordinate systems. As mentioned previously, the coordinate system of the input device 500 can be different than the coordinate system of the hyperdexterous surgical tools 300. The image on the display 600, 702 can show the motion of the hyperdexterous surgical tools 300 in the coordinate system of the hyperdexterous surgical tools 300.

Figure 42C:
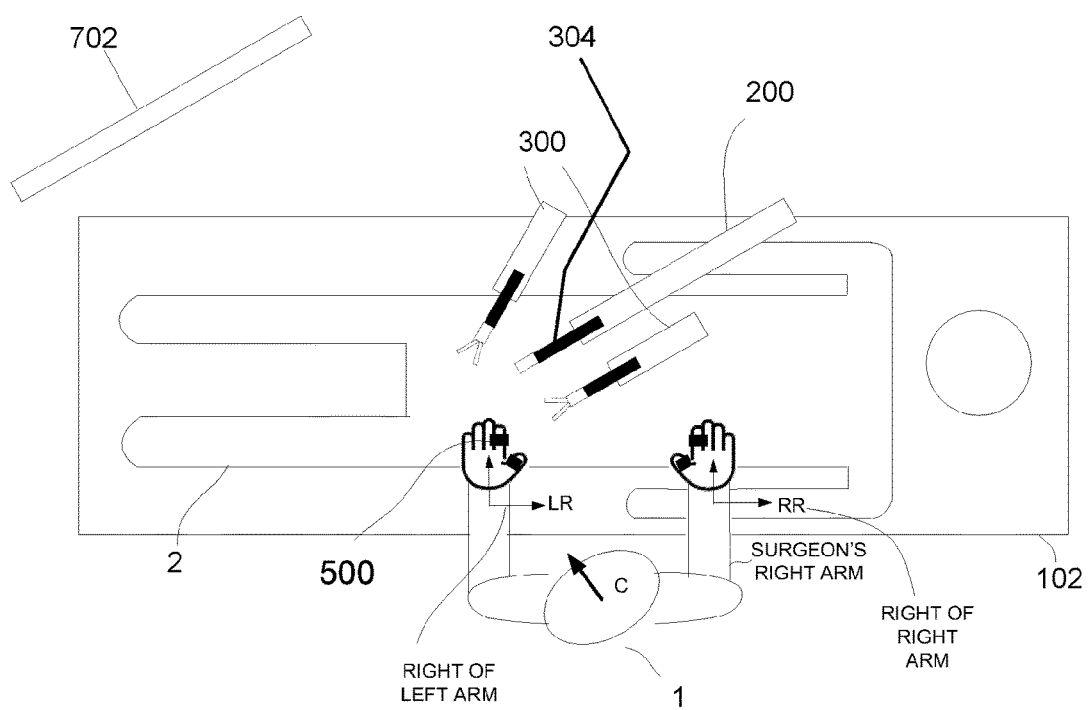
FIG. 42C schematically illustrates an operator controlling hyperdexterous surgical tools.

FIG. 42C shows another example of an arrangement of the tools, the display 702, and the operator 1. The display 702 is shown off to the left of the operator 1. The operator 1 is standing beside the patient 2 facing the patient 2 but has his or her head turned towards the display 702 (along Arrow C). The frame of references of each hyperdexterous surgical tool 300 is associated with each wrist of the operator 1. The control system 400 can enable natural control of the hyperdexterous surgical tool 300 from any location of the display 702. The display 702 can present visual cues to enable the operator to understand the motion of the hyperdexterous surgical tool 300 and the manual tools. Regardless of the orientation of the display 702, the control system can orient this image to augment the operator's understanding. The control system 400 can show on the display 702 a natural perspective of the surgery regardless of the positioning of the display 702. The association of the frames of reference with the wrists maintains the intuitiveness of control.

The displays 600, 702 can show the same image or different images. The display 600 can provide an input to the system, as described herein. The displays 600, 702 can show multiple images on a single screen.

The display 600, 702 may show different types of association between the motion of the input device 500 and the motion of the hyperdexterous surgical tool 300. There may be, in some embodiments, a 1:1 relationship between the hand motion, the tool motion, and the motion shown on the display. Other relationships are possible. The display 600, 702 may show inverse motion to the direction of the hand motion and the tool motion, such that the motion is shown in reverse. The display 600, 702 may show motion skewed at an angle to the direction of the hand motion and the tool motion. The display 600, 702 may show any orientation with respect to the frame of reference associated with the wrist.

The wrists are mentioned only as an example of an object which the frame of a reference may be associated with. The frame of reference can be affixed to any portion of the operator's body, the patient, objects in the work space, objects in the operating arena, the display, the hyperdexterous surgical tools, the camera the hyperdexterous surgical arms, or any other object. However, affixing the frame of reference to sections of the operator's body, including the forearm, wrist, hand, and head may facilitate control of the hyperdexterous surgical tools 300 in a natural manner.

As discussed herein, the hyperdexterous surgical system 100 advantageously allows the operator 1 to control the hyperdexterous surgical tools 300 from a variety of frames of references. For example, the operator 1 can control the hyperdexterous surgical tools 300 from a frame of reference of the camera 304 in the workspace, inside the body. The operator 1 can map the movements of his hand to the movement of the hyperdexterous surgical tool in the frame of reference of the camera 304. This view can be limiting for large motions or motions where it is more natural to move with respect to a frame of reference outside the body of the patient. Therefore, the hyperdexterous surgical system 100 allows the operator to dynamically change the frame of reference to another view. The operator 1 can switch to a world-grounded frame of reference (e.g., a view of the operating arena and the patient) for one or more hyperdexterous surgical tools 300. The world-grounded frame of reference may be helpful for large motions and/or when one or more hyperdexterous surgical tools 300 are locked to a single tool, as described herein. The world-grounded frame of reference may be helpful when moving one or more hyperdexterous surgical tools 300 to a new location relative to the patient. The world-grounded frame of reference may be helpful when the operator 1 repositions himself relative to the patient and/or switch which hands control the input device 500 based on his new position. The operator 1 can control the camera 304 and present images on the display 600, 702 of the world-grounded frame of reference. The hyperdexterous surgical system 100 allows the operator to dynamically change the frame of reference to back to the frame of reference of the camera 304.

In some embodiments, the frames of reference may be in motion. As a non-limiting example, a frame of reference may be attached to a manual tool 350 that may be in the process of being moved. The control system 400 may lock one or more hyperdexterous surgical tools 300 to the manual tool 350, such that the set of tools moves together. The concept of locking is described herein. The display 600, 702 may show a frame of reference associated with the moving tools and may provide assurance that the set of tools is moving as a group as intended.

A frame of reference may be established based on the position of the operator 1 when the clutch 112 is initially engaged. When the clutch 112 is engaged, the input device 500 can control one or more hyperdexterous surgical tools 300. When the clutch 112 is disengaged, the control system 400 can store this reference frame. When the clutch 112 is engaged again, the one or more hyperdexterous surgical tools 300 move with respect to the same reference frame established earlier.

In some embodiments when the clutch 112 is engaged again, a new reference frame is established based on the new position of the operator 1. The operator 1 may decide whether to use the frame of reference established in the prior engagement of the clutch 112 or to use a new frame of reference. The engagement of the clutch 112 may establish one or more frames of reference. Only one frame of reference may be established by the control system 400 if the operator 1 is only using one input device 500. However, if the operator 1 is using two input devices 500, then two frames of references may be established by the clutch 112. The frames of reference may be associated with each wrist and may be aligned, partially aligned or independent.

The right hand and the left hand of the operator 1 can manipulate objects in two different frames of reference. The objects can be dissimilar in size, shape or function. The hyperdexterous surgical system 100 allows simultaneous control of a manual tool 350 and a hyperdexterous surgical tool 300. The operator 1 is provided with enough cues regarding the constraints on the manual tool 350 and/or the hyperdexterous surgical tool 300 to enable this simultaneous control. The operator 1 is provided with enough cues regarding the frames of reference of the manual tool 350 and/or the hyperdexterous surgical tool 300 to enable this simultaneous control. The control system 400 of the hyperdexterous surgical system 100 advantageously allows the motion of the hyperdexterous surgical tools 300 and/or manual tools in various frames of reference. This ability may be very useful during the combined use of the manual tools 350 and the hyperdexterous surgical tools 300.

Sources of Visual Cues

One source of information is visual cues as seen by the operator 1, either through observing the operating arena or the displays 600, 702. Additional information can augment the operator's understanding of the motion of the hyperdexterous surgical tool 300 and the manual tool 350. The visual cues can be supplied by the control system and shown on the displays 600, 702.

One source of information is visual cues as seen by the operator 1 through observing the operating arena. From the operator's location, the operator can see the set-up of the operating arena. The operator 1 can see the orientation of his body, including his hands, relative to the patient. The operator 1 can see the location that the tools enter the body. In other words a surgeon may use objects around him or her such as the bed 102, the patient 2, his or her hands as cues to understand the position of the tools 300, 350 in relation to the anatomy. The surgeon can manipulate the hyperdexterous surgical tool 300 or the manual tool 350 consistent with that understanding.

One source of information is visual cues is images presented on the display 600, 702. The control system 400 can compute and present images relevant to the operator's understanding of the procedure. The images can enable the operator 1 to see the hyperdexterous surgical tools 300, the manual tools 350, and/or the patient's anatomy. The images can originate from one or more visualization components of the hyperdexterous surgical system 100. These components include one or more cameras 304, which can be controlled by the control system 400. The camera 304 can be considered a hyperdexterous surgical tool 300 and moved by a hyperdexterous robotic arm 200 to provide images to the operator 1. For instance, multiple cameras 304 may be deployed. Each camera 304 may acquire images of a different section of the anatomy. In some embodiments, millimeter-sized cameras 304 are placed onto each trocar tip. In some embodiments, the control system 400 and/or the visualization components perform real-time 3D reconstruction of the environment both internal and external to the patient 2. The control system 400 and/or the visualization components can integrate prior imaging of the patients, such as prior x-rays and CT scans. Information from sources can be blended to give more complete information to the operator 1. The visualization system 700 may provide the operator 1 the freedom to view the work space from various sources.

The images can be viewed on the one or more displays 600, 702. The display 600 may be configured to receive feedback from the operator 1, as described herein. The images can be viewed on the one or more immersive consoles 704. The hyperdexterous surgical system 100 allows the operator 1 to move around and place him or herself in the most optimal position in relation to the patient 2 for the procedure. During the procedure, the operator 1 (e.g., surgeon) may reposition himself or herself. The one or more displays 600, 702 allow the operator 1 to view the hyperdexterous surgical tools 300, the manual tools 350, and/or the patient's anatomy from multiple locations. The image on the display 600, 702 may be updated based on the location of the operator 1.

The image shown on the display 600, 702 may be dependent on the type of manipulations being performed. For example, if the operator 1 is doing delicate suturing, a zoomed in view of the anatomy and the tools may be shown on the display 600, 702. This view may be obtained directly from the camera 304. If the operator now wants to move to a different part of the body, gross motions of the tools are required, a zoomed out view may be shown on the display 600, 702. In other words, the zooming factor can adapt to the motion. The zooming function may be accomplished automatically by the control system 400 based at least in part on the type of motion being performed. The zooming function may also be initiated by the operator 1. The zoom levels may be changed using the input devices 500, such as by using gestures to zoom in or zoom out. Other ways of changing zoom levels are possible, such as attaching manual devices such as thumbwheels on the input device 500 where the operator can move the thumbwheel to change the zoom level. Other ways include providing buttons or slide bars on the display 702 or the display 600.

During zooming operations, the transition between images can be smooth and seamless. As the images zoom out, fewer anatomical details may be displayed. The control system may change the image feed, such as change from the camera 304 within the patient 1 to the feed from camera 304 mounted outside the patient's body. Other sources of data for the zoomed out view are discussed below.

In some embodiments, a virtual camera 706 (see FIG. 43) may be created thus enabling target visualization from various points of view. The virtual camera 706 creates an image from any point of view. The virtual camera 706 may be associated with the point of view of any of the multiple controllable objects present around the work space. The virtual camera 706 may be associated with the point of view of the operator 1 such as the surgeon. As the operator 1 moves around, the visualization system 700 adjusts to the current point of view of the operator. The virtual camera 706 can create an image using multiple sources, as described herein.

In some embodiments, the virtual camera 706 may be associated with the camera tool 304. The operator 1 such as a surgeon may choose to adjust the position of the camera 304 during surgery, therefore adjusting the virtual camera 706. Therefore, the display 600, 702 will be updated as the camera 304 moves.

Figure 43:
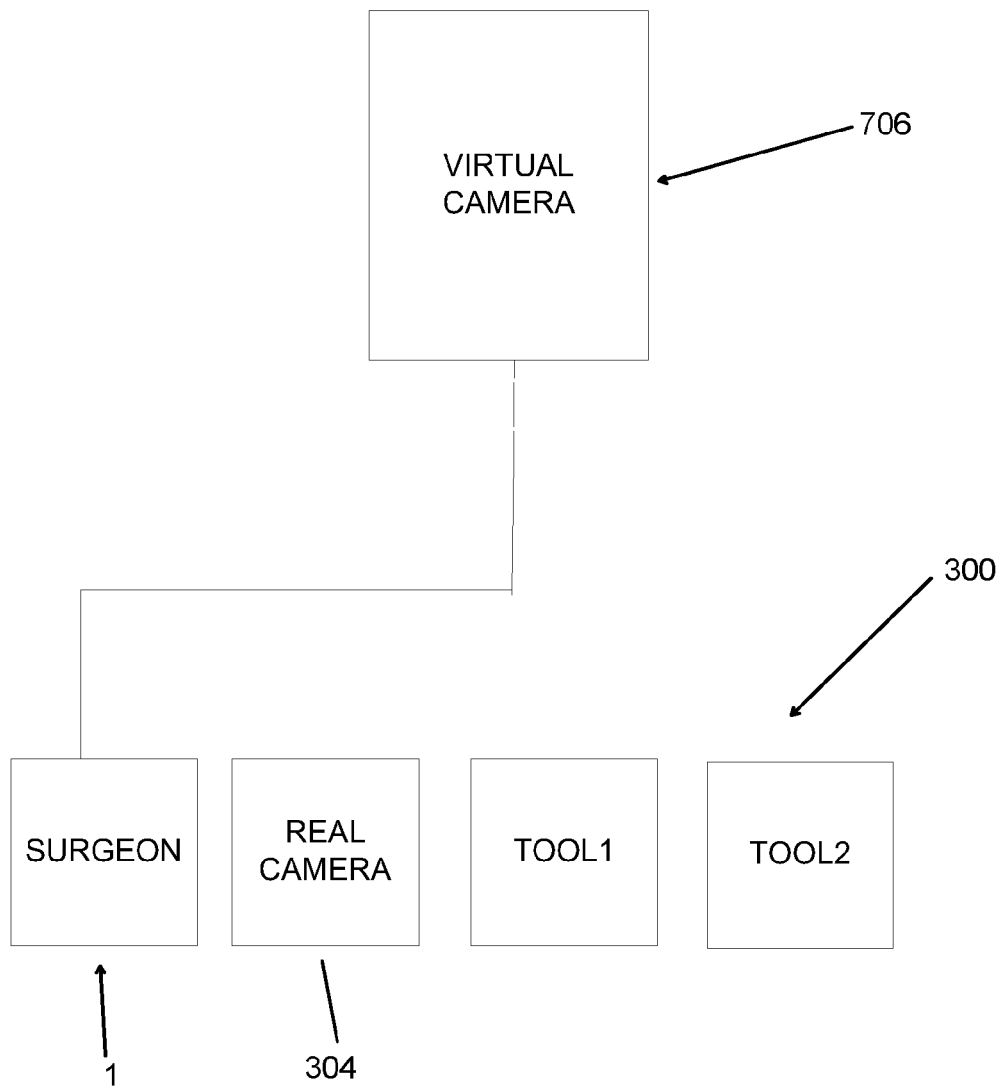
FIG. 43 schematically illustrates a screen shot of a display.

FIG. 43 shows an example of how a virtual camera 706 may be adjusted by the operator 1 such as a surgeon during surgery. The operator 1 can be tracked if he or she is wearing a tracking device. If the view of the camera 304 is inverted to that of the operator 1, the control system 400 can recognize the position of the operator 1 and invert the virtual camera 706 on the display 600, 702 to better reflect the point of view of the operator 1. As the operator 1 moves to be aligned with the camera 304, the control system 400 can recognize the position of the operator 1 and reflect the true image of the camera 304. Images may be inverted, rotated, and left-right flipped on the display 600, 702 to reflect the viewpoint of the tracked objects, such as the operator 1, or controllable objects such as hyperdexterous surgical arms 200 and/or hyperdexterous surgical tools 300. As another example, the display 600 may display sliders or buttons to change the position of the virtual camera 706 so that the operator 1 such as a surgeon may choose the most appropriate view.

Various camera parameters may be controlled and adjusted to enhance the image from the virtual camera 706. As a non-limiting example, the zoom function may be adjusted. For example, if large scale motions are desired, the image on the display 600, 702 may be zoomed out. As the operator 1 such as a surgeon maneuvers the tools for the large scale motion, the image on the display 600, 702 can zoom in and out to view the work space. This can be done automatically. The camera parameters such as angle and zoom may be adjusted using hand motions, for instance if the virtual camera 706 is controlled by an input device 500. The input device 500, such as sensors attached to the hand or wireless controllers, allow the advanced visualization system 700 to recognize a pattern of motion and perform functions such as change virtual angle and zoom.

The hyperdexterous surgical system 100 may have multiple displays 600, 702. Depending on the zoom levels, the control system 400 may display different images on each display 600, 702, each with different parameters such as different camera angle. This may allow an operator 1, such as a surgeon and/or a surgical assistant, to operate simultaneously on the patient and each refer to the display 600, 702 which presents the most natural point of view of the surgical work space relative to each person's location. This could be useful for example if an assistant is located close to the patient's legs and the primary surgeon is located at the patient's side. The assistant's display 702 would show the anatomy and tools from the point of view of the assistant, and the surgeon's display 702 would show the anatomy and tools from the point of view of the surgeon.

The parameters such as camera angle and the perspective of the images shown in each display 600, 702 may be dependent on one or more parameters including the position and orientation of the patient 2, the position and orientation of the display 600, 702, the position and orientation of the observer of the images such as the operator 1. This implies that the control system 400 has knowledge of the location and orientation of the various objects, such as the display 600, 702, the operator 1, and the patient 2. If such knowledge is not available, such as not knowing where the operator 1 is located, the control system 400 will calculate the images without that parameter.

As the operator 1 standing by the bedside looks at the patient 2 and subsequently looks up or towards the display 600, 702, he or she may find it useful to navigate the anatomy or tools in a zoomed out view. The zoomed out view may be created with data from various sources. These sources may include live data from cameras 304 attached in one or multiple locations around hyperdexterous surgical system 100 and/or attached to one or more hyperdexterous surgical tool 300. These sources may include pre-operative imaging data such as MRI or CT data or models of the anatomy. For example, the process of zooming out may start with displaying the images of the detailed internal anatomy as seen by a camera 304, which may be inside the patient's body placed through a port. As the zoom factor decreases (i.e. the camera is zoom out), the entire organ is displayed. As the zoom factor is decreased further, the point of view may move outside the body and may show the outside of the patient's body mixed in with a rendering of the internal organs. This concept is illustrated in FIG. 44.

Figure 44A:
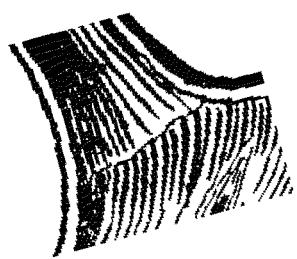
FIGS. 44A-44C schematically illustrate different images presented on a display.
Figure 44B:
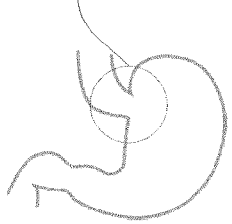
Figure 44C:
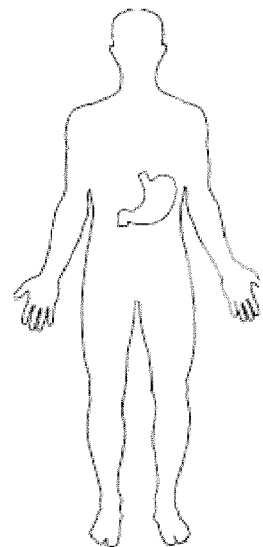

Starting with FIG. 44A, a zoomed in view of a section of the esophagus and the entry into the stomach (the gastroesophageal opening) is illustrated. This is a typical site for bariatric surgery where the stomach is bypassed. In FIG. 44B, the outline of the stomach and some parts of the esophagus is shown. The image shown in FIG. 44B is zoomed out with respect to FIG. 44A. In FIG. 44C, the stomach, esophagus is shown in relation to the whole body. The level of zoom can be adjusted to enable the surgeon to understand how best to manipulate the hyperdexterous surgical tools 300 and/or the manual tools 350. If the operator 1 only needs to visualize the end effectors, for instance for precise and small motion, then a "zoomed in" image such as in FIG. 44A may be useful. If the operator 1 wants to reposition the tools and use a different angle of approach to the anatomy, then an image such as FIG. 44C may be useful during the process of repositioning.

The hyperdexterous surgical system 100 enables a user to move from a zoomed in view inside the patient to a zoomed out view outside of the patient. The surgeon can move to new position when the image is in the zoomed out view. The operator 1 may find it easier to reposition himself relative to the patient in the zoomed out view. From this position, the operator 1 can zoom in to see the tools inside the body, as viewed from his new position. In some embodiments, the operator 1 can disengage the input device 500 before he repositions himself. The operator 1 can engage the input device 500 after he repositions himself. In some embodiments, the operator 1 can switch which hands control the input device 500 based on the new position.

The rendering of the internal organs may be a combination of various sources of data. These sources include actual, real-time images as seen by cameras or other visualization devices. These sources can include three-dimensional model data of the organs generated from the stereoscopic laparoscopic camera feed over the course of the surgery. These sources can include pre-operative data from MRI, CT or other imaging modality. The model may be corrected and enhanced as new data from a real-time source, such as the camera 304, becomes available. The corrected model could be then displayed.

The control system 400 may categorize the data into various classes such as, but not limited to, real time data (from the cameras 304), model data, pre-op data, stale data (specifically data from camera 304 that was taken prior to the current moment in time). Each type of data may be displayed differently in the blended image. For example, the stale data may be blended in with a shade of yellow indicating caution must be used in using that specific part of the data as it appears in the image. In another example, the model data may be blended in with a shade of red indicating extreme caution must be used in using that specific data as it appears in the image. This type of categorization and display may serve as warnings and reminders to the surgeon as he or she maneuvers the tools inside a patient's body while looking at images on the display 600, 702.

As the zoom factor and/or the point of view are adjusted, the control system 400 may change the relationship between the motion of the operator 1 (the controlling motion) and the motion of the hyperdexterous surgical tools 300 (the controlled motion). As an example, in the zoomed in view, the control system 400 may scale the motion of the hands in such a way that only small and precise motions are possible with large motions of the hand. As the images are zoomed out, the scaling between the controlling motion and the controlled motion may change, for instance such that, in some embodiments, there is a 1:1 relationship between the two. Other aspects may change according to the zoom factor such as the location of the virtual grip and the control points.

Figure 45:
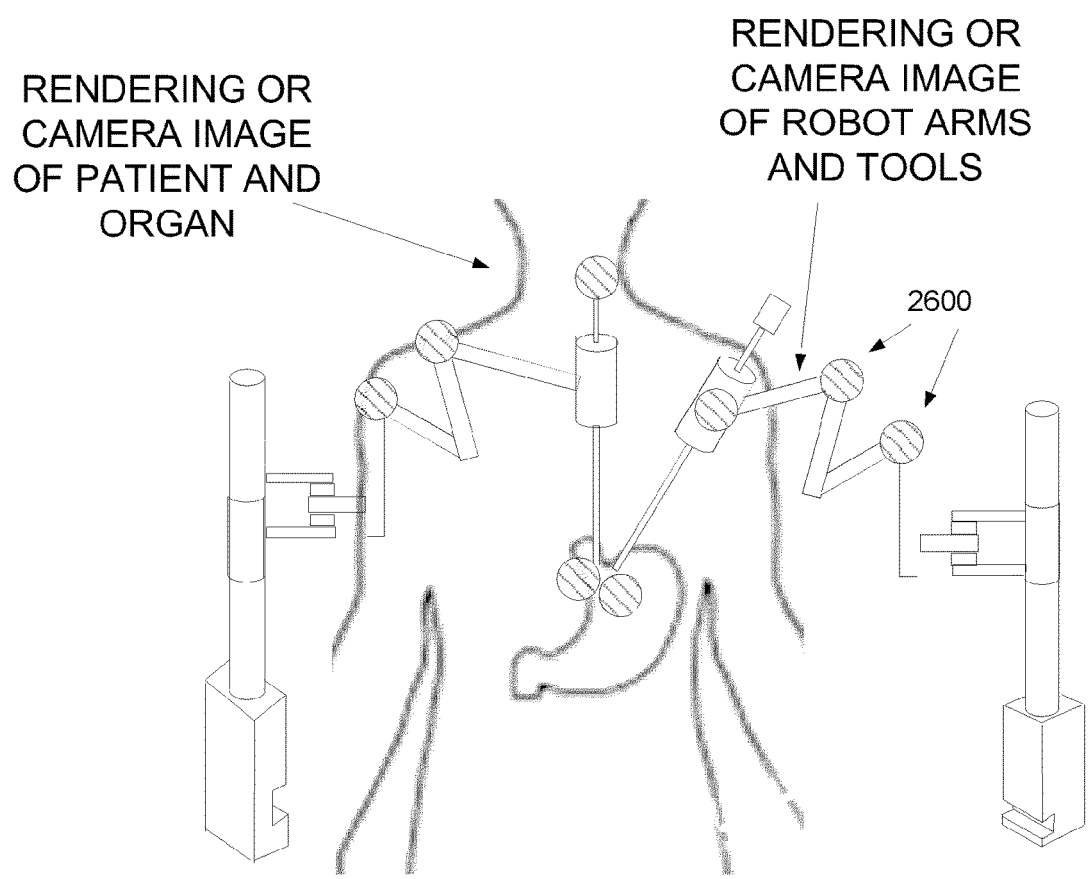
FIG. 45 schematically illustrates a screen shot of a display.

FIG. 45 shows an image as view on the display 702. The display 600 and/or display 702 can display features of the operating arena. The display 600 and/or display 702 can depict an image of one or more hyperdexterous surgical arms 200, one or more hyperdexterous surgical tool 300, one or more manual tool 350, the patient 2, the fixture (e.g., the bed), the operator 1, etc. The display 600 and/or display 702 can depict the control points of the hyperdexterous surgical system 100

The display 600 and/or display 702 may show the constraints of the hyperdexterous surgical system 100. For instance, the display 600, 702 may show the location of a fulcrum of a manual tool 350. The display 600, 702 can present the constraint to augment the operator's understanding. For instance, the display 600, 702 may show the location of a virtual grip 512 of a hyperdexterous surgical tool 300. The display 600, 702 can present the constraint to augment the operator's understanding.

The display 600 and/or display 702 may show the control points of the hyperdexterous surgical system 100. The control points 2600 are locations on the hyperdexterous surgical arm 200 and the hyperdexterous surgical tool 200 which have the ability to move. The control system 400 can cause movement about control points 2600 based upon an input of the operator 1 or a constraint. For instance, the input by the operator 1 effects the movement of the one or more sections that are connected to the control point 2600. Moving the control point 2600 causes the one or more sections of the hyperdexterous surgical arm 200 connected to the control point 2600 to move.

The control points 2600 can be moved via the input device 500. The movement of the input device 500 would cause movement of the selected control point 2600. This would cause movement of the hyperdexterous surgical tool 300 that is controlled by the hyperdexterous surgical arm 200. The display 600 may be used to assign an input device 500 to a specific control point 2600.

Control points 2600 may be indicated in various ways including but not limited to colors, cross hairs, other icons in the display. The image of the hyperdexterous surgical arm 200 on the display 600, 702 may be an actual camera image from one or many cameras 302 around the surgical site. The image of the hyperdexterous surgical arm 200 on the display 600, 702 may be a drawing.

An Embodiment of a Surgical Method

In some embodiments, one or more manual tools 350 are used in conjunction with one or more hyperdexterous surgical tools 300 in the same work space. An example of a manual tool 350 is a stapler 354, see FIG. 39. The stapler 354 may be used in conjunction with the hyperdexterous surgical tool 300. The workflow when using both types of tools in a colon resection surgical procedure is shown in FIG. 39, which shows a method 5. FIG. 39 illustrates one method of using a hyperdexterous surgical tool 300 and a manual tool 350. The method relates to holding the colon in a particular position and placing a staple line across the colon. The system includes a first grasper 312, a second grasper 314, a camera 304, and a stapler 354. The system includes two input devices 500, a first controller 516 and a second controller 518.

In step 10, the operator 1 may position the camera 304 by using any of the input devices 500. In some embodiments, the operator 1 connects an icon of the input device 500 with an icon of the controllable object such as the camera 304.

Then, in step 20, the operator 1 uses the first controller 516, which is controlled by one hand of the operator, to move a controllable object, such as the first grasper 312. The operator uses the first grasper 312 to position and hold a section of the colon. The operator uses the clutch 112 to disengage the controllable object, the first grasper 312. The first grasper 312 will remain in place. The operator 1 can set first controller 516 down.

Further, in step 30, the operator 1 can pick up the manual stapler 354 with one hand. The operator 1 can position the manual stapler 354 and move the stapler 354 to the targeted position, as seen by the positioned camera 304. In step 40, the operator 1 uses the second controller 518, which is controlled by the hand not holding the stapler 354. The second controller 518 moves a second controllable object, such as the second grasper 314. The operator 1 uses the second grasper 314 to position and hold a section of the colon. Then, in step 50, the operator 1 manipulates the stapler 354 and the second grasper 314 to position the colon in the most optimal position to receive the staples. Finally, in step 60, the operator 1 operates the manual stapler 354 and the staples are delivered to the targeted location. This method illustrates how one or more manual tools 350 and one or more the hyperdexterous surgical tools 300 may be used at the same time by the same operator 1 in the same work space. The operator 1 may be standing by the patient at all times (e.g., at one or more, for example a plurality of, bedside locations) during this procedure. In some embodiments, the operator 1 could perform the first two steps, steps 10 and 20, remotely, such as from the controller 514 remote from the patient.

With hyperdexterous surgical tools 300, it is often difficult to convey the feeling of touch. Surgeons sometimes use touch to get better information about the anatomy. However, many surgeons prefer to touch the patent in certain situations. In some embodiments, the manual tool 350 may be used to make contact with the tissue. This is done commonly with traditional surgery. The sensory input provided by using the manual tool 350 may guide the surgeon's manipulations of the hyperdexterous surgical tools 300. Proxy devices such as force sensors and load cells can convey a feeling of pressure or touch through complex mechanisms to the hyperdexterous surgical tools 300. The pressure conveyed by the hyperdexterous surgical tools 300 to the operator (via the one or more input devices 500, such as by communicating a signal from a transmitter of the control system 400 to a receiver of the input device 500) facilitates the understanding of the anatomy of the patient 2.

The manual tools 350 may be used in other methods, in conjunction with the hyperdexterous surgical tools 300. For instance, the hyperdexterous surgical arm 200 may hold the trocar 302, as shown in FIG. 2. The manual tool 350 or the hyperdexterous surgical tool 300 can be inserted through the trocar 302. This method of use may be beneficial for example when tissue needs to be held in place by the manual tool 350 while the surgeon manipulates the other tools. In another example, in obese patients the manipulation of tools becomes difficult due to the body habitus; in these cases the manual tool or the hyperdexterous surgical tool 300 can be held or supported by the hyperdexterous surgical arms 200 to relieve the physical stress on the operator 1.

In embodiments herein, the hyperdexterous surgical system is described as being coupled to a fixture. The hyperdexterous surgical system can be coupled to a bed, hospital bed, operating table, examination table, platform, floor, wall, cart, or dolly. Where the fixture is a cart or dolly, the fixture can be anchored to the floor. The fixture can be located within a medical office, a medical examiner's office, a hospital, a doctor's office, a clinical office, or any other location suitable for use of the hyperdexterous surgical system.

Although described in certain embodiments in connection with surgical procedures, the hyperdexterous surgical system can be used in any appropriate manner. The hyperdexterous surgical system can be used in a method that manipulates hyperdexterous surgical tools for percutaneous insertion. The hyperdexterous surgical system described herein can be operated in non-percutaneous procedures (e.g., procedures that do not involve making incisions and inserting the hyperdexterous surgical tools percutaneously). For example, the hyperdexterous surgical system can be used to take skin biopsies. The hyperdexterous surgical system can be used for any surgery. The hyperdexterous surgical system can be used in any appropriate medical procedure. The hyperdexterous surgical system can be used in conjunction with living patients (e.g., surgery) or cadavers (e.g., autopsies). The embodiments described herein can be used in any appropriate manner. The hyperdexterous surgical arm can be used in manufacturing or assembly of products (e.g., on an assembly line, in a clean room, etc.).

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A surgical system, comprising:
at least one electromechanical arm coupleable to a fixture;
at least one electromechanical tool supported by the at least one electromechanical arm to define an electromechanical arm and tool assembly;
a control system configured to communicate electronically with and control the operation of the electromechanical arm and tool assembly;
at least one portable handheld controller actuatable to communicate a control signal to the electromechanical arm and tool assembly via the control system to operate the electromechanical arm and tool assembly, wherein movements of the at least one portable handheld controller control movements of the electromechanical arm and tool assembly; and
a tracking system operable to track a position of the at least one portable handheld controller, wherein the tracking system comprises at least one position sensor integrated into the portable handheld controller,
wherein the at least one portable handheld controller is configured to be carried by a surgeon during a surgical procedure to a plurality of surgeon locations of an operating arena that are between an operating table and a remote control stand, thereby allowing the surgeon to be mobile between the plurality of surgeon locations during the surgical procedure and to operate the electromechanical arm and tool assembly using the at least one portable handheld controller from the plurality of surgeon locations of the operating arena, and wherein the position sensor is operable to track the position of the at least one portable handheld controller at any of the plurality of surgeon locations independent of the remote control stand.

2. The surgical system of claim 1, wherein one of the plurality of surgeon locations comprises beside the operating table of a patient.

3. The surgical system of claim 1, wherein one of the plurality of surgeon locations comprises the remote control stand.

4. The surgical system of claim 2, wherein the at least one portable handheld controller is operable from beside the operating table to thereby allow the surgeon to simultaneously operate a manual tool with one hand and the electromechanical arm and tool assembly with another hand via the at least one portable handheld controller.

5. The system of claim 4, wherein the electromechanical arm and tool assembly and the manual tool are operated independently of each other.

6. The system of claim 4, wherein the electromechanical arm and tool assembly and the manual tool are operated in frames of reference that are aligned or partially aligned.

7. The system of claim 4, wherein the electromechanical arm and tool assembly and the manual tool are operated in synchrony with each other.

8. The system of claim 4, wherein the electromechanical arm and tool assembly and the manual tool are operated in frames of reference that are independent of each other.

9. The surgical system of claim 1, further comprising a second electromechanical arm and tool assembly, wherein the electromechanical arm and tool assemblies are operable concurrently in the same surgical workspace.

10. The surgical system of claim 1, wherein the at least one portable handheld controller is wireless and communicates the control signal wirelessly.

11. The surgical system of claim 1, wherein the fixture is coupled to an operating table.

12. The system of claim 1, wherein the electromechanical arm comprises three degrees of freedom.

13. The system of claim 1, wherein the position sensor comprises an absolute encoder mounted to the portable handheld controller, and the absolute encoder is operable to track the position of the portable handheld controller relative to ground.

14. The system of claim 13, wherein tracking system further comprises a position sensor coupled to the surgeon, and the position sensor coupled to the surgeon is operable to track the position of the portable handheld controller relative to a ground reference point.

15. The system of claim 13, wherein the position sensor comprises an optical tracker mounted to the portable handheld controller, and the optical tracker is operable to track the position of the portable handheld controller relative to a ground reference point.

16. The system of claim 1, further comprising a visualization system configured to receive input signals from at least one source comprising a camera, the visualization system configured to display an image of a surgical workspace on at least one monitor within a line of sight of the surgeon.

17. The system of claim 1, wherein the at least one portable handheld controller is configured to selectively operate the electromechanical arm and tool assembly.

18. The system of claim 17, further comprising a clutch actuatable to selectively engage and disengage the at least one portable handheld controller with the electromechanical arm and tool assembly to thereby selectively operate the electromechanical arm and tool assembly.

19. The surgical system of claim 1, further comprising a user interface operable to selectively switch the portable handheld controller between operating different electromechanical arm and tool assemblies.

20. The surgical system of claim 19, wherein the user interface is a display.

* * * * *